(12) United States Patent
McGowan et al.

(10) Patent No.: US 11,319,283 B2
(45) Date of Patent: May 3, 2022

(54) SUBSTITUTED CYCLOBUTYLBENZENE COMPOUNDS AS INDOLEAMINE 2,3-DIOXYGENASE (IDO) INHIBITORS

(71) Applicants: MERCK SHARP & DOHME CORP., Rahway, NJ (US); Meredeth Ann McGowan, Boston, MA (US); Abdelghani Achab, Melrose, MA (US); Xavier Fradera, Boston, MA (US); Yongxin Han, Needham, MA (US); Derun Li, West Roxbury, MA (US); Jongwon Lim, Lexington, MA (US); Kun Liu, Needham, MA (US); Nunzio Sciammetta, Sudbury, MA (US); Catherine M. White, Newton Center, MA (US); Wensheng Yu, Edison, NJ (US); Hongjun Zhang, Boston, MA (US); Hua Zhou, Acton, MA (US)

(72) Inventors: Meredeth Ann McGowan, Boston, MA (US); Abdelghani Achab, Melrose, MA (US); Xavier Fradera, Boston, MA (US); Yongxin Han, Needham, MA (US); Derun Li, West Roxbury, MA (US); Jongwon Lim, Lexington, MA (US); Kun Liu, Needham, MA (US); Nunzio Sciammetta, Sudbury, MA (US); Catherine M. White, Newton Center, MA (US); Wensheng Yu, Edison, NJ (US); Hongjun Zhang, Boston, MA (US); Hua Zhou, Acton, MA (US)

(73) Assignee: MERCK SHARP & DOHME CORP., Rahway, NJ (US)

( * ) Notice: Subject to any disclaimer, the term of this patent is extended or adjusted under 35 U.S.C. 154(b) by 0 days.

(21) Appl. No.: 16/753,035

(22) PCT Filed: Oct. 4, 2018

(86) PCT No.: PCT/US2018/054273
§ 371 (c)(1),
(2) Date: Apr. 2, 2020

(87) PCT Pub. No.: WO2019/074747
PCT Pub. Date: Apr. 18, 2019

(65) Prior Publication Data
US 2020/0277252 A1    Sep. 3, 2020

Related U.S. Application Data

(60) Provisional application No. 62/569,874, filed on Oct. 9, 2017.

(51) Int. Cl.
C07D 205/04 (2006.01)
C07C 237/42 (2006.01)
C07D 213/75 (2006.01)
C07D 213/82 (2006.01)
C07D 231/14 (2006.01)
(Continued)

(52) U.S. Cl.
CPC .......... *C07C 237/42* (2013.01); *C07D 205/04* (2013.01); *C07D 213/75* (2013.01); *C07D 213/82* (2013.01); *C07D 231/14* (2013.01); *C07D 233/90* (2013.01); *C07D 237/20* (2013.01); *C07D 239/28* (2013.01); *C07D 241/24* (2013.01); *C07D 263/34* (2013.01); *C07D 277/56* (2013.01); *C07D 285/06* (2013.01); *C07D 307/14* (2013.01); *C07D 309/14* (2013.01); *C07D 487/04* (2013.01)

(58) Field of Classification Search
None
See application file for complete search history.

(56) References Cited

U.S. PATENT DOCUMENTS

| | | | |
|---|---|---|---|
| 9,073,895 | B2 | 7/2015 | Berry et al. |
| 2011/0245236 | A1 | 10/2011 | Ali et al. |
| 2014/0377292 | A1 | 12/2014 | Combs et al. |
| 2016/0137653 | A1 | 5/2016 | Beck et al. |

FOREIGN PATENT DOCUMENTS

| | | |
|---|---|---|
| WO | 2017139414 A1 | 8/2017 |
| WO | 2019099294 A1 | 5/2019 |
| WO | 2019099314 A1 | 5/2019 |

OTHER PUBLICATIONS

Database Registry Chemical Abstracts Service, Columbus, Ohio, Accession No. RN 1340704-38-2, Entered STN: Nov. 4, 2011.*

(Continued)

*Primary Examiner* — Samantha L Shterengarts
(74) *Attorney, Agent, or Firm* — Yong Zhao; Catherine D. Fitch

(57) ABSTRACT

Disclosed herein is a compound of formula (I), or a pharmaceutically acceptable salt thereof: (Formula (I)). Also disclosed herein are uses of a compound disclosed herein in the potential treatment or prevention of an IDO-associated disease or disorder. Also disclosed herein are compositions comprising a compound disclosed herein. Further disclosed herein are uses of a composition in the potential treatment or prevention of an IDO-associated disease or disorder.

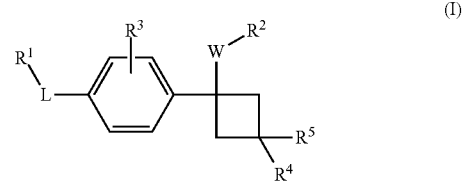

7 Claims, No Drawings

(51) Int. Cl.
  *C07D 233/90*  (2006.01)
  *C07D 237/20*  (2006.01)
  *C07D 239/28*  (2006.01)
  *C07D 241/24*  (2006.01)
  *C07D 263/34*  (2006.01)
  *C07D 277/56*  (2006.01)
  *C07D 285/06*  (2006.01)
  *C07D 307/14*  (2006.01)
  *C07D 309/14*  (2006.01)
  *C07D 487/04*  (2006.01)

(56) References Cited

OTHER PUBLICATIONS

Database Registry Chemical Abstracts Service, Columbus, Ohio, Accession No. RN 1019179-25-9, Entered STN: May 5, 2008.*
PUBCHEM-CID: 46384131 Create Date: Jul. 21, 2010 (Jul. 21, 2010) pp. 1-11; p. 3, Fig.
PUBCHEM-CID: 53110538 Create Date: Jun. 21, 2011 (Jun. 21, 2011) pp. 1-10. p. 3, Fig.
European Search Report, EP18866155.7-1110 / 3694502 (PCT/US201805427), dated May 12, 2021, 7 pages.
He, Wu et al., Identification of A Novel Small-Molecule Binding Site of the Fat Mass and Obesity Associated Protein (FTO), Journal of Medicinal Chemistry, 2015, 7341-7348, 58(18).
Rohrig, U.F. et al., Challenges in the Discovery of Indoleamine 2,3-Dioxygenase 1 (IDO1) Inhibitors, J. Med. Chem., 2015, 9421-9437, 58.

\* cited by examiner

SUBSTITUTED CYCLOBUTYLBENZENE COMPOUNDS AS INDOLEAMINE 2,3-DIOXYGENASE (IDO) INHIBITORS

CROSS REFERENCE TO RELATED APPLICATIONS

The present application is the 371 national phase application of International Application No. PCT/US2018/054273, filed Oct. 4, 2018, which claims the benefit of U.S. Provisional Application No. 62/569,874, filed Oct. 9, 2017, hereby incorporated by reference in their entirety.

BACKGROUND OF THE INVENTION

Tryptophan (Trp) is an essential amino acid required for the biosynthesis of proteins, niacin and the neurotransmitter 5-hydroxytryptamine (serotonin). The enzyme indoleamine 2,3-dioxygenase (IDO) catalyzes the first and rate limiting step in the degradation of L-tryptophan to N-formyl-kynurenine. In human cells, a depletion of Trp resulting from IDO activity is a prominent gamma interferon (EFN-γ)-inducible antimicrobial effector mechanism. IFN-γ stimulation induces activation of IDO, which leads to a depletion of Trp, thereby arresting the growth of Trp-dependent intracellular pathogens such as *Toxoplasma gondii* and *Chlamydia trachomatis*. IDO activity also has an antiproliferative effect on many tumor cells, and IDO induction has been observed in vivo during rejection of allogeneic tumors, indicating a possible role for this enzyme in the tumor rejection process (Daubener, et al, 1999, Adv. Exp. Med. Biol, 467: 517-24; Taylor, et al, 1991, FASEB J., 5: 2516-22).

It has been observed that HeLa cells co-cultured with peripheral blood lymphocytes (PBLs) acquire an immunoinhibitory phenotype through up-regulation of IDO activity. A reduction in PBL proliferation upon treatment with interleukin-2 (IL2) was believed to result from IDO released by the tumor cells in response to IFN-γ secretion by the PBLs. This effect was reversed by treatment with 1-methyl-tryptophan (IMT), a specific IDO inhibitor. It was proposed that IDO activity in tumor cells may serve to impair antitumor responses (Logan, et al, 2002, Immunology, 105: 478-87).

Several lines of evidence suggest that IDO is involved in induction of immune tolerance. Studies of mammalian pregnancy, tumor resistance, chronic infections and autoimmune diseases have shown that cells expressing IDO can suppress T-cell responses and promote tolerance. Accelerated Trp catabolism has been observed in diseases and disorders associated with cellular immune activation, such as infection, malignancy, autoimmune diseases and AIDS, as well as during pregnancy. For example, increased levels of IFNs and elevated levels of urinary Trp metabolites have been observed in autoimmune diseases; it has been postulated that systemic or local depletion of Trp occurring in autoimmune diseases may relate to the degeneration and wasting symptoms of these diseases. In support of this hypothesis, high levels of IDO were observed in cells isolated from the synovia of arthritic joints. IFNs are also elevated in human immunodeficiency virus (HIV) patients and increasing IFN levels are associated with a worsening prognosis. Thus, it was proposed that IDO is induced chronically by HIV infection, and is further increased by opportunistic infections, and that the chronic loss of Trp initiates mechanisms responsible for cachexia, dementia and diarrhea and possibly immunosuppression of AIDS patients (Brown, et al., 1991, Adv. Exp. Med. Biol, 294: 425-35). To this end, it has recently been shown that IDO inhibition can enhance the levels of virus-specific T cells and, concomitantly, reduce the number of virally-infected macrophages in a mouse model of HIV (Portula et al., 2005, Blood, 106: 2382-90).

IDO is believed to play a role in the immunosuppressive processes that prevent fetal rejection in utero. More than 40 years ago, it was observed that, during pregnancy, the genetically disparate mammalian conceptus survives in spite of what would be predicted by tissue transplantation immunology (Medawar, 1953, Symp. Soc. Exp. Biol. 7: 320-38). Anatomic separation of mother and fetus and antigenic immaturity of the fetus cannot fully explain fetal allograft survival. Recent attention has focused on immunologic tolerance of the mother. Because IDO is expressed by human syncytiotrophoblast cells and systemic tryptophan concentration falls during normal pregnancy, it was hypothesized that IDO expression at the maternal-fetal interface is necessary to prevent immunologic rejection of the fetal allografts. To test this hypothesis, pregnant mice (carrying syngeneic or allogeneic fetuses) were exposed to IMT, and a rapid, T cell-induced rejection of all allogeneic conception was observed. Thus, by catabolizing tryptophan, the mammalian conceptus appears to suppress T-cell activity and defends itself against rejection, and blocking tryptophan catabolism during murine pregnancy allows maternal T cells to provoke fetal allograft rejection (Moan, et al., 1998, Science, 281: 1191-3).

Further evidence for a tumoral immune resistance mechanism based on tryptophan degradation by IDO comes from the observation that most human tumors constitutively express IDO, and that expression of IDO by immunogenic mouse tumor cells prevents their rejection by preimmunized mice. This effect is accompanied by a lack of accumulation of specific T cells at the tumor site and can be partly reverted by systemic treatment of mice with an inhibitor of IDO, in the absence of noticeable toxicity. Thus, it was suggested that the efficacy of therapeutic vaccination of cancer patients might be improved by concomitant administration of an IDO inhibitor (Uyttenhove et al., 2003, Nature Med., 9: 1269-74). It has also been shown that the IDO inhibitor, 1-MT, can synergize with chemotherapeutic agents to reduce tumor growth in mice, suggesting that IDO inhibition may also enhance the anti-tumor activity of conventional cytotoxic therapies (Muller et al, 2005, Nature Med., 11: 312-9).

One mechanism contributing to immunologic unresponsiveness toward tumors may be presentation of tumor antigens by tolerogenic host APCs. A subset of human IDO-expressing antigen-presenting cells (APCs) that coexpressed CD 123 (IL3RA) and CCR6 and inhibited T-cell proliferation have also been described. Both mature and immature CD123-positive dendritic cells suppressed T-cell activity, and this IDO suppressive activity was blocked by 1MT (Munn, et al, 2002, Science, 297: 1867-70). It has also been demonstrated that mouse tumor-draining lymph nodes (TDLNs) contain a subset of plasmacytoid dendritic cells (pDCs) that constitutively express immunosuppressive levels of IDO. Despite comprising only 0.5% of lymph node cells, in vitro, these pDCs potently suppressed T cell responses to antigens presented by the pDCs themselves and also, in a dominant fashion, suppressed T cell responses to third-party antigens presented by nonsuppressive APCs. Within the population of pDCs, the majority of the functional IDO-mediated suppressor activity segregated with a novel subset of pDCs coexpressing the B-lineage marker CD19. Thus, it was hypothesized that IDO-mediated suppression by pDCs in TDLNs creates a local microenvironment that is potently suppressive of host antitumor T cell responses (Munn, et al., 2004, J. Clin. Invest, 114(2): 280-90).

IDO degrades the indole moiety of tryptophan, serotonin and melatonin, and initiates the production of neuroactive and immunoregulatory metabolites, collectively known as kynurenines. By locally depleting tryptophan and increasing proapoptotic kynurenines, IDO expressed by dendritic cells (DCs) can greatly affect T-cell proliferation and survival. IDO induction in DCs could be a common mechanism of deletional tolerance driven by regulatory T cells. Because such tolerogenic responses can be expected to operate in a variety of physiopathological conditions, tryptophan metabolism and kynurenine production might represent a crucial interface between the immune and nervous systems (Grohmann, et al, 2003, Trends Immunol, 24: 242-8). In states of persistent immune activation, availability of free serum Trp is diminished and, as a consequence of reduced serotonin production, serotonergic functions may also be affected (Wirleitner, et al., 2003, Curr. Med. Chem., 10: 1581-91).

In light of the potential role for IDO in immunosuppression, tumor resistance and/or rejection, chronic infections, HIV-infection, AIDS (including its manifestations such as cachexia, dementia and diarrhea), autoimmune diseases or disorders (such as rheumatoid arthritis), and immunologic tolerance and prevention of fetal rejection in utero, therapeutic agents aimed at suppression of tryptophan degradation by inhibiting IDO activity are desirable. Inhibitors of IDO can be used to activate T cells and therefore enhance T cell activation when the T cells are suppressed by pregnancy, malignancy or a virus such as HIV. Inhibition of IDO may also be an important treatment strategy for patients with neurological or neuropsychiatric diseases or disorders such as depression. Compounds disclosed herein are useful in the potential treatment or prevention of IDO-related diseases.

SUMMARY OF THE INVENTION

Disclosed herein are novel compounds of formula (I), which are inhibitors of the IDO enzymes. Also disclosed herein are uses of these compounds in the potential treatment or prevention of an IDO-associated disease or disorder. Also disclosed herein are compositions comprising one or more of the compounds. Further disclosed herein are uses of these compositions in the potential prevention or treatment of an IDO-associated disease or disorder.

DETAILED DESCRIPTION OF THE INVENTION

Disclosed herein is a compound of formula (I), or a pharmaceutically acceptable salt thereof:

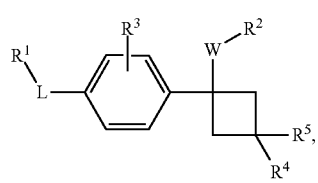

(I)

wherein:
L is selected from (1) a bond, (2) —NHC(O)— and (3) —C(O)NH—;

W is selected from (1) —C(O)NH— and (2) —NHC(O)—;
$R^1$ is selected from:
(1) $C_{1-6}$ alkyl,
(2) $C_{3-6}$ cycloalkyl,
(3) aryl, and
(4) heterocyclyl;
wherein the $C_{1-6}$ alkyl of (1) is optionally substituted with 1-3 substituents independently selected from (a) halogen, (b) $C_{3-6}$ cycloalkyl, and (c) —O—$C_{1-6}$ alkyl; and
wherein each of the $C_{3-6}$ cycloalkyl of (2), aryl of (3), and heterocyclyl of (4) is optionally substituted with 1-3 substituents independently selected from (a) halogen, (b) $C_{3-6}$ cycloalkyl, (c) —CN, (d) —O—$C_{1-6}$ alkyl, and (e) $C_{1-6}$ alkyl optionally substituted with 1-3 substituents independently selected from halogen and —NH$_2$;
$R^2$ is selected from:
(1) $C_{1-6}$ alkyl,
(2) $C_{3-6}$ cycloalkyl,
(3) aryl,
(4) —S(O)$_2$-aryl, and
(5) heterocyclyl;
wherein the $C_{1-6}$ alkyl of (1) is optionally substituted with 1-3 substituents independently selected from (a) halogen, (b) $C_{3-6}$ cycloalkyl, (c) —O—$C_{1-6}$ alkyl, and (d) heterocyclyl; and
wherein each of the $C_{3-6}$ cycloalkyl of (2), aryl of (3) and (4), and heterocyclyl of (5) is optionally substituted with 1-3 substituents independently selected from (a) halogen, (b) —CN, (c) —O—$C_{1-6}$ alkyl, and (d) $C_{1-6}$ alkyl optionally substituted with 1-3 halogens;
$R^3$ is selected from:
(1) H,
(2) halogen,
(3) $C_{1-6}$ alkyl, optionally substituted with —OH, and
(4) —C=N—$C_{1-6}$ alkyl; and
each of $R^4$ and $R^5$ is independently selected from:
(1) H,
(2) halogen,
(3) $C_{1-6}$ alkyl,
(4) —OH, and
(5) —O—$C_{1-6}$ alkyl.

In one embodiment of the compound of formula (I), or a pharmaceutically acceptable salt thereof:
L is selected from (1) —NHC(O)— and (2) —C(O)NH—; and
$R^3$ is selected from (1) H, (2) halogen, (3) $C_{1-4}$ alkyl, optionally substituted with —OH, and (4) —C=N—$C_{1-4}$ alkyl.

In one embodiment of the compound of formula (I), or a pharmaceutically acceptable salt thereof:
$R^3$ is selected from (1) H, (2) fluoro, (3) methyl, (4) ethyl, (5) —CH$_3$—OH, and (6) —C=N—C(CH$_3$)$_3$.

In one embodiment of the compound of formula (I), or a pharmaceutically acceptable salt thereof:
each of $R^4$ and $R^5$ is independently selected from (1) H, (2) halogen, (3) methyl, and (4) —OH.

In one embodiment of the compound of formula (I), or a pharmaceutically acceptable salt thereof:
$R^1$ is selected from:
(1) $C_{3-6}$ cycloalkyl, optionally substituted with 1-3 substituents independently selected from (a) halogen, (b) —O—$C_{1-6}$ alkyl, and (c) $C_{1-6}$ alkyl optionally substituted with 1-3 halogens,
(2) phenyl, optionally substituted with 1-3 substituents independently selected from (a) halogen, (b) —CN, (c) —O—$C_{1-6}$ alkyl, and (d) $C_{1-6}$ alkyl optionally substituted with 1-3 substituents independently selected from (a) halogen and (b) —NH$_2$,
(3) a bicyclic ring comprising a phenyl fused to a C$_{4-7}$cycloalkyl, wherein the bicyclic ring is optionally substituted with halogen or C$_{1-6}$ alkyl, and
(4) a heterocyclyl selected from (a) a saturated 4-7 membered monocyclic heterocyclyl, (b) a partially unsaturated 4-7 membered monocyclic heterocyclyl, (c) an aromatic 4-7 membered monocyclic heterocyclyl, and (d) a 6-9 membered fused bicyclic ring containing one or more heteroatoms selected from N, O, and S in either of the rings, wherein the heterocyclyl is optionally substituted with 1-3 substituents independently selected from (a) halogen and (b) C$_{1-6}$ alkyl, optionally substituted with 1-3 halogens.

In one embodiment of the compound of formula (I), or a pharmaceutically acceptable salt thereof:
R$^1$ is selected from:
(1) C$_{3-6}$ cycloalkyl, optionally substituted with 1-3 substituents independently selected from (a) halogen, (b) methyl, (c) ethyl, (d) —CHF$_2$, and (e) —CF$_3$,
(2) phenyl, optionally substituted with 1-3 substituents independently selected from (a) halogen, (b) —CN, (c) methyl, (d) ethyl, (e) —CHF$_2$, (f) —CF$_3$, and (g) —CH$_2$NH$_2$, (3) a bicyclic ring comprising a phenyl fused to a cyclobutyl, optionally substituted with halogen or C$_{1-6}$ alkyl and
(4) a heterocyclyl selected from azetidinyl, imidazole-[1,2-b]pyridazinyl, isoxazolyl, isothiazolyl, oxazolyl, pyrazolyl, pyridinyl, pyrimidinyl, tetrahydrofuranyl, tetrahydropyranyl, and 1,2,3-thiadiazolyl, wherein each heterocyclyl is optionally substituted with 1-3 substituents independently selected from (a) halogen, (b) methyl, and (c) ethyl.

In one embodiment of the compound of formula (I), or a pharmaceutically acceptable salt thereof:
R$^2$ is selected from:
(1) C$_{1-6}$ alkyl, optionally substituted with 1-3 substituents independently selected from (a) halogen, (b) —O—C$_{1-6}$ alkyl, and (c) C$_{3-6}$ cycloalkyl,
(2) C$_{3-6}$ cycloalkyl, optionally substituted with 1-3 substituents independently selected from (a) halogen, (b) —O—C$_{1-6}$ alkyl, and (c) C$_{1-6}$ alkyl optionally substituted with 1-3 substituents independently selected from (a) fluoro and (b) —NH$_2$,
(3) phenyl, optionally substituted with 1-3 substituents independently selected from (a) halogen, (b) —CN, and (c) C$_{1-6}$ alkyl,
(4) a bicyclic ring comprising a phenyl fused to a C$_{4-7}$cycloalkyl, optionally substituted with halogen or C$_{1-6}$ alkyl,
(5) —S(O)$_2$-aryl, and
(6) a heterocyclyl selected from (a) a saturated 4-7 membered monocyclic heterocyclyl, (b) a partially unsaturated 4-7 membered monocyclic heterocyclyl, and (c) an aromatic 4-7 membered monocyclic heterocyclyl, wherein each heterocyclyl is optionally substituted with 1-3 substituents independently selected from (a) halogen and (b) C$_{1-6}$ alkyl, optionally substituted with 1-3 halogens.

In one embodiment of the compound of formula (I), or a pharmaceutically acceptable salt thereof:
R$^2$ is selected from:
(1) C$_{1-4}$ alkyl, optionally substituted with 1-3 substituents independently selected from (a) halogen, (b) —O—C$_{1-4}$ alkyl, and (c) C$_{3-6}$ cycloalkyl,
(2) C$_{3-6}$ cycloalkyl, optionally substituted with 1-3 substituents independently selected from (a) halogen, (b) methyl, (c) ethyl, (d) —CH$_3$—NH$_2$, (e) CHF$_2$, (f) CF$_3$, and (g) —O-ethyl,
(3) phenyl, optionally substituted with 1-3 substituents independently selected from (a) halogen, (b) methyl, (c) ethyl, and (d) —CN,
(4) —S(O)$_2$-phenyl, and
(5) a heterocyclyl selected from azetidinyl, imidazolyl, oxazolyl, pyrazinyl, pyrazolyl, pyridinyl, pyrimidinyl, tetrahydrofuranyl, tetrahydropyranyl, and thiazolyl, wherein each heterocyclyl is optionally substituted with 1-3 substituents independently selected from (a) halogen, (b) methyl, (c) ethyl, and (c) —CH$_2$CF$_3$.

In one embodiment of the compound of formula (I), or a pharmaceutically acceptable salt thereof:
L is selected from (1) —NHC(O)— and (2) —C(O)NH—;
W is selected from (1) —C(O)NH— and (2) —NHC(O)—;
R$^1$ is selected from:
(1) C$_{1-6}$ alkyl, optionally substituted with 1-3 substituents independently selected from (a) halogen, (b) C$_{3-6}$ cycloalkyl and (c) —O—C$_{1-6}$ alkyl,
(2) C$_{3-6}$ cycloalkyl, optionally substituted with 1-3 substituents independently selected from (a) halogen, (b) —O—C$_{1-6}$ alkyl and (c) C$_{1-6}$ alkyl optionally substituted with 1-3 halogens,
(3) phenyl, optionally substituted with 1-3 substituents independently selected from (a) halogen, (b) —CN, (c) —O—C$_{1-6}$ alkyl and (d) C$_{1-6}$ alkyl optionally substituted with 1-3 substituents independently selected from (i) halogen and (ii) —NH$_2$,
(4) a bicyclic ring comprising a phenyl fused to a C$_{4-7}$cycloalkyl, wherein the bicyclic ring is optionally substituted with halogen or C$_{1-6}$ alkyl, and
(5) a heterocyclyl selected from (a) a saturated 4-7 membered monocyclic heterocyclyl, (b) a partially unsaturated 4-7 membered monocyclic heterocyclyl, (c) an aromatic 4-7 membered monocyclic heterocyclyl, and (d) a 6-9 membered fused bicyclic ring containing one or more heteroatoms selected from N, O, and S in either of the rings, wherein the heterocyclyl is optionally substituted with 1-3 substituents independently selected from (a) halogen and (b) C$_{1-6}$ alkyl, optionally substituted with 1-3 halogens;
R$^2$ is selected from:
(1) C$_{1-6}$ alkyl, optionally substituted with 1-3 substituents independently selected from (a) halogen, (b) —O—C$_{1-4}$alkyl, and (c) C$_{3-6}$ cycloalkyl,
(2) C$_{3-6}$ cycloalkyl, optionally substituted with 1-3 substituents independently selected from (a) halogen and (b) C$_{1-6}$ alkyl optionally substituted with 1-3 substituents independently selected from (i) halogen, (ii) —O—C$_{1-4}$alkyl, and (iii) —NH$_2$,
(3) phenyl, optionally substituted with 1-3 substituents independently selected from (a) halogen, (b) —CN, and (b) C$_{1-6}$ alkyl,
(4) a bicyclic ring comprising a phenyl fused to a C$_{4-7}$cycloalkyl, optionally substituted with halogen or C$_{1-6}$ alkyl,
(5) —S(O)$_2$-phenyl, and
(6) a heterocyclyl selected from (a) a saturated 4-7 membered monocyclic heterocyclyl, (b) a partially unsaturated 4-7 membered monocyclic heterocyclyl, and (c) an aromatic 4-7 membered monocyclic heterocyclyl, wherein the heterocyclyl is optionally substituted with 1-3 substituents independently selected from (a) halogen and (b) $C_{1-6}$ alkyl optionally substituted with 1-3 halogens;

$R^3$ is selected from (1) H, (2) halogen, (3) $C_{1-4}$ alkyl, optionally substituted with —OH, and (4) —C=N—$C_{1-4}$ alkyl; and each of $R^4$ and $R^5$ is independently selected from (1) H, (2) halogen, (3) —OH, and (4) methyl.

In one embodiment of the compound of formula (I), or a pharmaceutically acceptable salt thereof, the compound is of formula (Ia):

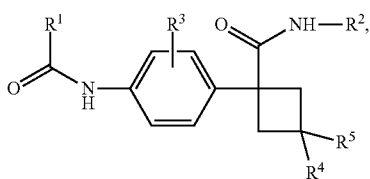

(Ia)

wherein $R^1$ is selected from:
(1) $C_{3-6}$ cycloalkyl, optionally substituted with 1-3 substituents halogens,
(2) phenyl, optionally substituted with 1-3 substituents independently selected from (a) halogen, (b) —CN, and (c) $C_{1-6}$ alkyl optionally substituted with 1-3 substituents independently selected from (a) halogen and (b) —NH$_2$,
(3) a bicyclic ring comprising a phenyl fused to a $C_{4-7}$cycloalkyl, wherein the bicyclic ring is optionally substituted with halogen or $C_{1-6}$ alkyl, and
(4) a heterocyclyl selected from (a) a saturated 4-7 membered monocyclic heterocyclyl, (b) a partially unsaturated 4-7 membered monocyclic heterocyclyl, (c) an aromatic 4-7 membered monocyclic heterocyclyl, and (d) a 6-9 membered fused bicyclic ring containing one or more heteroatoms selected from N, O, and S in either of the rings, wherein the heterocyclyl is optionally substituted with 1-3 substituents independently selected from (a) halogen and (b) $C_{1-6}$ alkyl, optionally substituted with 1-3 halogens;

$R^2$ is selected from:
(1) $C_{1-6}$ alkyl, optionally substituted with 1-3 substituents independently selected from (a) halogen and (b) $C_{3-6}$ cycloalkyl,
(2) $C_{3-6}$ cycloalkyl, optionally substituted with 1-3 substituents independently selected from (a) halogen and (b) $C_{1-6}$ alkyl optionally substituted with 1-3 substituents independently selected from (a) halogen, (b) —O—$C_{1-4}$ alkyl, and (c) —NH$_2$,
(3) phenyl, optionally substituted with 1-3 substituents independently selected from (a) halogen, (b) —CN, and (c) $C_{1-6}$ alkyl,
(4) a bicyclic ring comprising a phenyl fused to a $C_{4-7}$cycloalkyl, optionally substituted with halogen or $C_{1-6}$ alkyl,
(5) —S(O)$_2$-aryl, and
(6) a heterocyclyl selected from (a) a saturated 4-7 membered monocyclic heterocyclyl, (b) a partially unsaturated 4-7 membered monocyclic heterocyclyl, and (c) an aromatic 4-7 membered monocyclic heterocyclyl, wherein the heterocyclyl is optionally substituted with 1-3 substituents independently selected from (a) halogen and (b) $C_{1-6}$ alkyl, optionally substituted with 1-3 halogens;

$R^3$ is selected from (1) H, (2) fluoro, (3) methyl, (4) ethyl, (5) —CH$_2$—OH, and (6) —C=N—C(CH$_3$)$_3$; and each of $R^4$ and $R^5$ is independently selected from (1) H, (2) halogen, (3) —OH, and (4) methyl.

In one embodiment of the compound of formula (Ia), or a pharmaceutically acceptable salt thereof:

$R^1$ is selected from:
(1) $C_{3-6}$ cycloalkyl, optionally substituted with 1-3 halogens,
(2) phenyl, optionally substituted with 1-3 substituents independently selected from (a) halogen, (b) —CN, (c) methyl, (d) —CH$_2$NH$_2$,
(3) a bicyclic ring comprising a phenyl fused to a cyclobutyl, and
(4) a heterocyclyl selected from azetidinyl, imidazo[1,2-b]pyridazinyl, oxazolyl, pyridinyl, pyrimidinyl, tetrahydropyranyl, and 1,2,3-thiadiazolyl, wherein the heterocyclyl is optionally substituted with 1-3 halogens;

$R^2$ is selected from:
(1) $C_{1-4}$ alkyl, optionally substituted with 1-3 substituents independently selected from (a) halogen, (b) —O—$C_{1-4}$ alkyl, and $C_{3-6}$ cycloalkyl,
(2) $C_{3-6}$ cycloalkyl, optionally substituted with 1-3 substituents independently selected from (a) halogen, (b) methyl, (c) ethyl, (d) —O-ethyl, (e) —CHF$_2$, and (f) —CF$_3$,
(3) phenyl, optionally substituted with 1-3 substituents independently selected from (a) halogen and (b) —CN,
(4) a bicyclic ring comprising a phenyl fused to a cyclobutyl, optionally substituted with 1-3 halogens,
(5) —S(O)$_2$-phenyl, and
(6) a heterocyclyl selected from azetidinyl, imidazolyl, oxazolyl, pyrazinyl, pyrazolyl, pyridinyl, pyrimidinyl, tetrahydrofuranyl, tetrahydropyranyl and thiazolyl, wherein the heterocyclyl is optionally substituted with 1-3 substituents independently selected from (a) halogen, (b) methyl, (c) ethyl, and (d) —CH$_2$CF$_3$;

$R^3$ is selected from (1) H, (2) fluoro, (3) methyl, (4) —CH$_2$—OH, and (5) —C=N—C(CH$_3$)$_3$; and each of $R^4$ and $R^5$ is independently selected from (1) H, (2) fluoro, and (3) —OH.

In one embodiment of the compound of formula (I), or a pharmaceutically acceptable salt thereof, the compound is of formula (Ib):

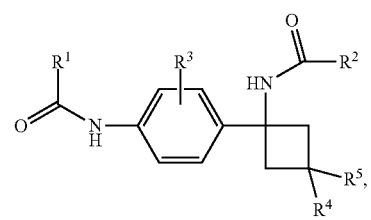

(Ib)

wherein:
$R^1$ is selected from:
(1) $C_{3-6}$ cycloalkyl, optionally substituted with 1-3 substituents independently selected from (a) halogen, (b) —O—$C_{1-6}$ alkyl and (c) $C_{1-6}$ alkyl optionally substituted with 1-3 halogens,
(2) phenyl, optionally substituted with 1-3 substituents independently selected from (a) halogen, (b) —CN, (c) —O—$C_{1-6}$ alkyl and (d) $C_{1-6}$ alkyl optionally substituted with 1-3 halogens, (3) a bicyclic ring comprising a phenyl fused to a $C_{4-7}$cycloalkyl, wherein the bicyclic ring is optionally substituted with halogen or $C_{1-6}$ alkyl, and (4) a heterocyclyl selected from (a) a saturated 4-7 membered monocyclic heterocyclyl, (b) a partially unsaturated 4-7 membered monocyclic heterocyclyl, (c) an aromatic 4-7 membered monocyclic heterocyclyl, and (d) a 6-9 membered fused bicyclic ring containing one or more heteroatoms selected from N, O, and S in either of the rings, wherein the heterocyclyl is optionally substituted with 1-3 substituents independently selected from (a) halogen, (b) —CN and (c) $C_{1-6}$ alkyl;

$R^2$ is selected from:
  (1) $C_{1-6}$ alkyl, optionally substituted with 1-3 substituents independently selected from (a) halogen and (b) $C_{3-6}$ cycloalkyl,
  (2) $C_{3-6}$ cycloalkyl, optionally substituted with 1-3 substituents independently selected from (a) halogen and (b) $C_{1-6}$ alkyl optionally substituted with —NH$_2$,
  (3) phenyl, optionally substituted with 1-3 substituents independently selected from (a) halogen and (b) $C_{1-6}$ alkyl,
  (4) a bicyclic ring comprising a phenyl fused to a $C_{4-7}$cycloalkyl, optionally substituted with halogen or $C_{1-6}$ alkyl,
  (5) —S(O)$_2$-aryl, and
  (6) a heterocyclyl selected from (a) a saturated 4-7 membered monocyclic heterocyclyl, (b) a partially unsaturated 4-7 membered monocyclic heterocyclyl, and (c) an aromatic 4-7 membered monocyclic heterocyclyl, wherein the heterocyclyl is optionally substituted with 1-3 substituents independently selected from (a) halogen and (b) $C_{1-6}$ alkyl;

$R^3$ is selected from (1) H, (2) fluoro, (3) methyl, (4) ethyl, (5) —CH$_3$—OH, and (6) —C≡N—C(CH$_3$)$_3$; and
each of $R^4$ and $R^5$ is independently selected from (1) H, (2) halogen, (3) —OH, and (4) methyl.

In one embodiment of the compound of formula (Ib), or a pharmaceutically acceptable salt thereof:

$R^1$ is selected from:
  (1) $C_{3-6}$ cycloalkyl, optionally substituted with 1-3 halogens,
  (2) phenyl, optionally substituted with 1-3 substituents independently selected from (a) halogen, (b) —CN, (c) methyl, (d) —CH$_2$NH$_2$,
  (3) a bicyclic ring comprising a phenyl fused to a cyclobutyl, and
  (4) a heterocyclyl selected from azetidinyl, imidazo[1,2-b]pyridazinyl, oxazolyl, pyridinyl, pyrimidinyl, tetrahydropyranyl, and 1,2,3-thiadiazolyl, wherein the heterocyclyl is optionally substituted with 1-3 halogens;

$R^2$ is selected from:
  (1) $C_{1-4}$ alkyl, optionally substituted with 1-3 substituents independently selected from (a) halogen, (b) —O—$C_{1-4}$ alkyl, and $C_{3-6}$ cycloalkyl,
  (2) $C_{3-6}$ cycloalkyl, optionally substituted with 1-3 substituents independently selected from (a) halogen, (b) methyl, (c) ethyl, (d) —O-ethyl, (e) —CHF$_2$, and (f) —CF$_3$,
  (3) phenyl, optionally substituted with 1-3 substituents independently selected from (a) halogen and (b) —CN,
  (4) a bicyclic ring comprising a phenyl fused to a cyclobutyl, optionally substituted with 1-3 halogens,
  (5) —S(O)$_2$-phenyl, and
  (6) a heterocyclyl selected from azetidinyl, imidazolyl, oxazolyl, pyrazinyl, pyrazolyl, pyridinyl, pyrimidinyl, tetrahydrofuranyl, tetrahydropyranyl and thiazolyl, wherein the heterocyclyl is optionally substituted with 1-3 substituents independently selected from (a) halogen, (b) methyl, (c) ethyl, and (d) —CH$_2$CF$_3$;

$R^3$ is selected from (1) H, (2) fluoro, (3) methyl, (4) —CH$_3$—OH, and (5) —C≡N—C(CH$_3$)$_3$; and each of $R^4$ and $R^5$ is independently selected from (1) H, (2) fluoro, and (3) —OH.

In one embodiment of the compound of formula (I), or a pharmaceutically acceptable salt thereof:

L is selected from —NHC(O)— and —C(O)NH—;
W is selected from —C(O)NH— and —NHC(O)—;

$R^1$ is selected from:
  (1) $C_{1-6}$alkyl,
  (2) $C_{3-6}$ cycloalkyl,
  (3) aryl and
  (4) heterocyclyl;
  wherein the $C_{1-6}$ alkyl of (1) is optionally substituted with 1-3 substituents independently selected from (a) halogen, (b) $C_{3-6}$ cycloalkyl and (c) —O—$C_{1-6}$ alkyl; and
  wherein each of the $C_{3-6}$ cycloalkyl of (2), aryl of (3) and heterocyclyl of (4) is optionally substituted with 1-3 substituents independently selected from (a) halogen, (b) $C_{3-6}$ cycloalkyl, (c) —CN, (d) —O—$C_{1-6}$ alkyl and (e) $C_{1-6}$ alkyl optionally substituted with 1-3 substituents independently selected from halogen and —NH$_2$;

$R^2$ is selected from:
  (1) $C_{1-6}$alkyl,
  (2) $C_{3-6}$ cycloalkyl,
  (3) aryl,
  (4) —S(O)$_2$-aryl and
  (5) heterocyclyl;
  wherein the $C_{1-6}$ alkyl of (1) is optionally substituted with 1-3 substituents independently selected from (a) halogen, (b) $C_{3-6}$ cycloalkyl, (c) —O—$C_{1-6}$ alkyl and (d) heterocyclyl; and
  wherein each of the $C_{3-6}$ cycloalkyl of (2), aryl of (3) and (4) and heterocyclyl of (5) is optionally substituted with 1-3 substituents independently selected from (a) halogen, (b) —CN, (c) —O—$C_{1-6}$ alkyl and (d) $C_{1-6}$ alkyl optionally substituted with 1-3 halogens;

$R^3$ is selected from H, halogen, $C_{1-6}$ alkyl and —C≡N—$C_{1-6}$ alkyl; and
each of $R^4$ and $R^5$ is independently selected from H, halogen, $C_{1-6}$ alkyl, —OH and —O—$C_{1-6}$ alkyl.

In one embodiment of the compound of formula (Ia), or a pharmaceutically acceptable salt thereof:

$R^1$ is selected from:
  (1) $C_{1-6}$ alkyl; optionally substituted with 1-3 substituents independently selected from (a) halogen, (b) $C_{3-6}$ cycloalkyl and (c) —O—$C_{1-6}$ alkyl;
  (2) $C_{3-6}$ cycloalkyl, optionally substituted with 1-3 substituents independently selected from (a) halogen, (b) —O—$C_{1-6}$ alkyl and (c) $C_{1-6}$ alkyl optionally substituted with 1-3 halogens;
  (3) phenyl, optionally substituted with 1-3 substituents independently selected from (a) halogen, (b) —CN, (c) —O—$C_{1-6}$ alkyl and (d) $C_{1-6}$ alkyl optionally substituted with 1-3 halogens;
  (4) a bicyclic ring comprising a phenyl fused to a $C_{4-7}$cycloalkyl, wherein the bicyclic ring is optionally substituted with halogen or $C_{1-6}$ alkyl; and
  (5) a heterocyclyl selected from a saturated, a partially unsaturated and an aromatic 4-7 membered monocyclic heterocyclyl and a fused bicyclic ring containing one or more heteroatoms selected from N, O, and S in either of the rings; wherein the heterocyclyl is optionally substituted with 1-3 substituents independently selected from (a) halogen, (b) —CN and (c) $C_{1-6}$ alkyl;

$R^2$ is selected from:
- (1) $C_{1-6}$ alkyl; optionally substituted with 1-3 substituents independently selected from (a) halogen and (b) $C_{3-6}$ cycloalkyl;
- (2) $C_{3-6}$ cycloalkyl, optionally substituted with 1-3 substituents independently selected from (a) halogen and (b) $C_{1-6}$ alkyl optionally substituted with —$NH_2$;
- (3) phenyl, optionally substituted with 1-3 substituents independently selected from (a) halogen and (b) $C_{1-6}$ alkyl;
- (4) a bicyclic ring comprising a phenyl fused to a $C_{4-7}$cycloalkyl, optionally substituted with halogen or $C_{1-6}$ alkyl; and
- (5) a heterocyclyl selected from a saturated, a partially unsaturated and an aromatic 4-7 membered monocyclic heterocyclyl; wherein the heterocyclyl is optionally substituted with 1-3 substituents independently selected from (a) halogen, (b) —CN and (c) $C_{1-6}$ alkyl;

$R^3$ is selected from H and halogen; and each of $R^4$ and $R^5$ is independently selected from H, halogen, —OH and methyl.

In one embodiment of the compound of formula (Ib), or a pharmaceutically acceptable salt thereof:

$R^1$ is selected from:
- (1) $C_{1-6}$ alkyl; optionally substituted with 1-3 substituents independently selected from (a) halogen, (b) $C_{3-6}$ cycloalkyl and (c) —O—$C_{1-6}$ alkyl;
- (2) $C_{3-6}$ cycloalkyl, optionally substituted with 1-3 substituents independently selected from (a) halogen, (b) —O—$C_{1-6}$ alkyl and (c) $C_{1-6}$ alkyl optionally substituted with 1-3 halogens;
- (3) phenyl, optionally substituted with 1-3 substituents independently selected from (a) halogen, (b) —CN, (c) —O—$C_{1-6}$ alkyl and (d) $C_{1-6}$ alkyl optionally substituted with 1-3 halogens;
- (4) a bicyclic ring comprising a phenyl fused to a $C_{4-7}$cycloalkyl, wherein the bicyclic ring is optionally substituted with halogen or $C_{1-6}$ alkyl; and
- (5) a heterocyclyl selected from a saturated, a partially unsaturated and an aromatic 4-7 membered monocyclic heterocyclyl and a fused bicyclic ring containing one or more heteroatoms selected from N, O, and S in either of the rings; wherein the heterocyclyl is optionally substituted with 1-3 substituents independently selected from (a) halogen, (b) —CN and (c) $C_{1-6}$ alkyl;

$R^2$ is selected from:
- (1) $C_{1-6}$ alkyl; optionally substituted with 1-3 substituents independently selected from (a) halogen and (b) $C_{3-6}$ cycloalkyl;
- (2) $C_{3-6}$ cycloalkyl, optionally substituted with 1-3 substituents independently selected from (a) halogen and (b) $C_{1-6}$ alkyl optionally substituted with —$NH_2$;
- (3) phenyl, optionally substituted with 1-3 substituents independently selected from (a) halogen and (b) $C_{1-6}$ alkyl;
- (4) a bicyclic ring comprising a phenyl fused to a $C_{4-7}$cycloalkyl, optionally substituted with halogen or $C_{1-6}$ alkyl; and
- (5) a heterocyclyl selected from a saturated, a partially unsaturated and an aromatic 4-7 membered monocyclic heterocyclyl; wherein the heterocyclyl is optionally substituted with 1-3 substituents independently selected from (a) halogen, (b) —CN and (c) $C_{1-6}$ alkyl;

$R^3$ is selected from H and halogen; and each of $R^4$ and $R^5$ is independently selected from H, halogen, —OH and methyl.

In one embodiment, a compound disclosed herein is selected from the group consisting of the compounds exemplified in Examples 1 to 88; or a pharmaceutically acceptable salt, solvate or hydrate thereof.

Also disclosed herein is a pharmaceutical composition comprising a compound disclosed herein and at least one pharmaceutically acceptable carrier.

Also disclosed herein is a method of inhibiting activity of indoleamine 2,3-dioxygenase (IDO) comprising contacting IDO with a compound disclosed herein, or a pharmaceutically acceptable salt, solvate or hydrate thereof.

Also disclosed herein is a method of inhibiting immunosuppression in a patient comprising administering to said patient an effective amount of a compound disclosed herein, or a pharmaceutically acceptable salt, solvate or hydrate thereof.

Also disclosed herein is a method of treating cancer, viral infection, depression, a neurodegenerative disorder, trauma, age-related cataracts, organ transplant rejection, or an autoimmune disease in a patient comprising administering to said patient an effective amount of a compound disclosed herein, or a pharmaceutically acceptable salt, solvate or hydrate thereof.

Also disclosed herein is a method of treating melanoma in a patient comprising administering to said patient an effective amount of a compound disclosed herein, or a pharmaceutically acceptable salt, solvate or hydrate thereof.

Further disclosed herein is a compound disclosed herein, or a pharmaceutically acceptable salt thereof, for use in therapy. In one embodiment, disclosed herein is the use of a compound disclosed herein, or a pharmaceutically acceptable salt, solvate or hydrate thereof, for the preparation of a medicament for use in therapy.

"Alkyl" refers to both branched- and straight-chain saturated aliphatic hydrocarbon groups of 1 to 18 carbon atoms, or more specifically, 1 to 12 carbon atoms. Examples of such groups include, but are not limited to, methyl (Me), ethyl (Et), n-propyl (Pr), n-butyl (Bu), n-pentyl, n-hexyl, and the isomers thereof such as isopropyl (i-Pr), isobutyl (i-Bu), sec-butyl (s-Bu), tert-butyl (t-Bu), isopentyl, and isohexyl. Alkyl groups may be optionally substituted with one or more substituents as defined herein. "$C_{1-6}$alkyl" refers to an alkyl group as defined herein having 1 to 6 carbon atoms.

"Aryl" refers to an aromatic monocyclic or multicyclic ring moiety comprising 6 to 14 ring carbon atoms, or more specifically, 6 to 10 ring carbon atoms. Monocyclic aryl rings include, but are not limited to, phenyl. Multicyclic rings include, but are not limited to, naphthyl and bicyclic rings wherein phenyl is fused to a $C_{4-7}$cycloalkyl or $C_{4-7}$cycloalkenyl ring. Aryl groups may be optionally substituted with one or more substituents as defined herein. Bonding can be through any of the carbon atoms of any ring.

In one embodiment, the aryl is phenyl. In another embodiment, the aryl is a bicyclic ring wherein phenyl is fused to a 4-7 membered cycloalkyl ring. In another embodiment, the aryl is a bicyclic ring wherein phenyl is fused to a 4-membered cycloalkyl ring. In another embodiment, the aryl is a bicyclic ring wherein phenyl is fused to a 4-membered cycloalkenyl ring. In another embodiment, the aryl is bicyclo[4.2.0]octa-1(6),2,4-trienyl.

"Cycloalkyl" refers to a monocyclic saturated carbocyclic ring having the specified number of carbon atoms. For example, $C_{3-6}$cycloalkyl refers to a cycloalkyl group as defined herein having 3 to 6 carbon atoms. Examples of cycloalkyl include, but are not limited to, cyclopropyl, cyclobutyl, cyclopentyl, cyclohexyl and cycloheptanyl. Cycloalkyl groups may be optionally substituted with one or more substituents as defined herein. In one embodiment, the cycloalkyl is a 5-membered bridged bicyclic ring.

"Halo" or "halogen" refers to fluoro, chloro, bromo or iodo, unless otherwise noted.

"Heterocycle" or "heterocyclyl" refers to a saturated, partially unsaturated or aromatic ring moiety having at least one ring heteroatom and at least one ring carbon atom. In one embodiment, the heteroatom is oxygen, sulfur, or nitrogen. A heterocycle containing more than one heteroatom may contain different heteroatoms. Heterocyclyl moieties include both monocyclic and multicyclic (e.g., bicyclic) ring moieties. Bicyclic ring moieties include fused, spirocycle and bridged bicyclic rings and may comprise one or more heteroatoms in either of the rings. The ring attached to the remainder of the molecule may or may not contain a heteroatom. Either ring of a bicyclic heterocycle may be saturated, partially unsaturated or aromatic. The heterocycle may be attached to the rest of the molecule via a ring carbon atom, a ring oxygen atom or a ring nitrogen atom. Non-limiting examples of heterocycles are described below.

In one embodiment, the heterocyclyl is selected from azetidinyl, dioxanyl, imidazolyl, imidazo[1,2-b]pyridazinyl, oxazolyl, pyrazinyl, pyrazolyl, pyridinyl, pyrimidinyl, tetrahydrofuranyl, tetrahydropyranyl, 1,2,3-thiadiazolyl, and thiazolyl.

In one embodiment, the heterocyclyl is selected from azetidinyl, imidazo[1,2-b]pyridazinyl, oxazolyl, pyridinyl, pyrimidinyl, tetrahydropyranyl, and 1,2,3-thiadiazolyl.

In one embodiment, the heterocyclyl is selected from azetidinyl, dioxanyl, imidazolyl, oxazolyl, pyrazinyl, pyrazolyl, pyridinyl, pyrimidinyl, tetrahydrofuranyl, tetrahydropyranyl and thiazolyl.

Heterocyclic groups may be optionally substituted with one or more substituents as defined herein.

"Optionally substituted" refers to "unsubstituted or substituted," and therefore, the generic structural formulas described herein encompass compounds containing the specified optional substituent(s) as well as compounds that do not contain the optional substituent(s). Each substituent is independently defined each time it occurs within the generic structural formula definitions.

Polymorphism

A compound disclosed herein, including a salt, solvate or hydrate thereof, may exist in crystalline form, non-crystalline form, or a mixture thereof. A compound or a salt or solvate thereof may also exhibit polymorphism, i.e. the capacity of occurring in different crystalline forms. These different crystalline forms are typically known as "polymorphs". Polymorphs have the same chemical composition but differ in packing, geometrical arrangement, and other descriptive properties of crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, all of which may be used for identification. One of ordinary skill in the art will appreciate that different polymorphs may be produced, for example, by changing or adjusting the conditions used in crystallizing/recrystallizing a compound disclosed herein.

Optical Isomers—Diastereomers—Geometric Isomers—Tautomers

Included herein are various isomers of the compounds disclosed herein. The term "isomers" refers to compounds that have the same composition and molecular weight but differ in physical and/or chemical properties. The structural difference may be in constitution (geometric isomers) or in the ability to rotate the plane of polarized light (stereoisomers).

With regard to stereoisomers, a compound disclosed herein may have one or more asymmetric carbon atom and may occur as mixtures (such as a racemic mixture) or as individual enantiomers or diastereomers. All such isomeric forms are included herein, including mixtures thereof. If a compound disclosed herein contains a double bond, the substituent may be in the E or Z configuration. If a compound disclosed herein contains a disubstituted cycloalkyl, the cycloalkyl substituent may have a cis- or trans-configuration. All tautomeric forms are also intended to be included.

Any asymmetric atom (e.g., carbon) of a compound disclosed herein, can be present in racemic mixture or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis- (Z)- or trans-(E)-form.

A compound disclosed herein, can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of the final compounds of the examples or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds can also be resolved by chiral chromatography, e.g., high pressure liquid chromatography (HPLC) using a chiral adsorbent.

Some of the compounds described herein may exist with different points of attachment of hydrogen, referred to as tautomers. For example, compounds including carbonyl —$CH_2C(O)$— groups (keto forms) may undergo tautomerism to form hydroxyl —CH=C(OH)— groups (enol forms). Both keto and enol forms, individually as well as mixtures thereof, are included within the scope of the present invention.

Isotopic Variations

Compounds disclosed herein, include unlabeled forms, as well as isotopically labeled forms. Isotopically labeled compounds have structures depicted by the formulas given herein except that one or more atoms are replaced by an atom having a selected atomic mass or mass number. Examples of isotopes that can be incorporated into compounds disclosed herein include isotopes of hydrogen, carbon, nitrogen, oxygen, phosphorous, sulfur, fluorine, iodine and chlorine, such as $^2H$ (i.e., Deuterium or "D"), $^3H$, $^{11}C$, $^{13}C$, $^{14}C$, $^{13}N$, $^{15}N$, $^{15}O$, $^{17}O$, $^{18}O$, $^{32}P$, $^{35}S$, $^{18}F$, $^{123}I$, $^{125}I$ and $^{36}Cl$. The invention includes various isotopically labeled compounds as defined herein, for example those into which radioactive isotopes, such as $^{3}H$ and $^{14}C$, or those into which non-radioactive isotopes, such as $^{2}H$ and $^{13}C$ are present. Such isotopically labeled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, substitution with positron emitting isotopes, such as $^{11}C$, $^{18}F$, $^{15}O$ and $^{13}N$ may be particularly desirable for PET or SPECT studies.

Isotopically-labeled compounds disclosed herein, can generally be prepared by conventional techniques known to those skilled in the art. Furthermore, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index.

Pharmaceutically Acceptable Salts

The term "pharmaceutically acceptable salt" refers to a salt prepared from a pharmaceutically acceptable non-toxic base or acid, including inorganic or organic base and inorganic or organic acid. Salts derived from inorganic bases include aluminum, ammonium, calcium, copper, ferric, ferrous, lithium, magnesium, manganic salts, manganous, potassium, sodium, zinc, and the like. Particular embodiments include ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When a compound disclosed herein is basic, a salt may be prepared from a pharmaceutically acceptable non-toxic acid, including an inorganic and organic acid. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, trifluoroacetic acid (TFA) and the like. Particular embodiments include the citric, hydrobromic, hydrochloric, maleic, phosphoric, sulfuric, fumaric, tartaric and trifluoroacetic acids.

Methods of Use

Compounds disclosed herein can inhibit activity of the enzyme indoleamine-2,3-dioxygenase (IDO). For example, the compounds disclosed herein can potentially be used to inhibit activity of IDO in cell or in an individual in need of modulation of the enzyme by administering an effective amount of a compound. Further disclosed herein are methods of inhibiting the degradation of tryptophan in a system containing cells expressing IDO such as a tissue, living organism, or cell culture. In some embodiments, the present invention provides methods of altering (e.g., increasing) extracellular tryptophan levels in a mammal by administering an effective amount of a compound or composition provided herein. Methods of measuring tryptophan levels and tryptophan degradation are routine in the art.

Also disclosed herein are methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, viral infection, viral replication, etc.

Also disclosed herein are methods of treating diseases associated with activity or expression, including abnormal activity and/or overexpression, of IDO in an individual (e.g., patient) by administering to the individual in need of such treatment an effective amount or dose of a compound disclosed herein or a pharmaceutical composition thereof. Example diseases can include any disease, disorder or condition that may be directly or indirectly linked to expression or activity of the IDO enzyme, such as over expression or abnormal activity. An IDO-associated disease can also include any disease, disorder or condition that may be prevented, ameliorated, or cured by modulating enzyme activity. Examples of IDO-associated diseases include cancer, viral infection such as HIV and HCV, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, allergic inflammation, inflammatory bowel disease, psoriasis and systemic lupus erythematosusor. Example cancers potentially treatable by the methods herein include cancer of the colon, pancreas, breast, prostate, lung, brain, ovary, cervix, testes, renal, head and neck, lymphoma, leukemia, melanoma, and the like. The compounds of the invention may also be useful in the treatment of obesity and ischemia. As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound disclosed herein includes the administration of a compound of the present invention to an individual or patient, such as a human, as well as, for example, introducing a compound of the invention into a sample containing a cellular or purified preparation containing the IDO enzyme.

A subject administered with a compound disclosed herein, or a pharmaceutically acceptable salt, solvate or hydrate thereof, is generally a mammal, such as a human being, male or female. A subject also refers to cows, sheep, goats, horses, dogs, cats, rabbits, rats, mice, fish, and birds. In one embodiment, the subject is a human.

As used herein, the terms "treatment" and "treating" refer to all processes wherein there may be a slowing, interrupting, arresting, controlling, or stopping of the progression of a disease or disorder that may be associated with IDO enzyme activity. The terms do not necessarily indicate a total elimination of all disease or disorder symptoms. The terms also include the potential prophylactic therapy of the mentioned conditions, particularly in a subject that is predisposed to such disease or disorder.

The terms "administration of" and or "administering a" compound should be understood to include providing a compound described herein, or a pharmaceutically acceptable salt, solvate or hydrate thereof, and compositions of the foregoing to a subject.

The amount of a compound administered to a subject is an amount sufficient to inhibit IDO enzyme activity in the subject. In an embodiment, the amount of a compound can be an "effective amount", wherein the subject compound is administered in an amount that will elicit a biological or medical response of a tissue, system, animal or human that is being sought by a researcher, veterinarian, medical doctor or other clinician. An effective amount does not necessarily include considerations of toxicity and safety related to the administration of a compound. It is recognized that one skilled in the art may affect physiological disorders associated with an IDO enzyme activity by treating a subject presently afflicted with the disorders, or by prophylactically treating a subject likely to be afflicted with the disorders, with an effective amount of a compound disclosed herein, or a pharmaceutically acceptable salt, solvate or hydrate thereof.

An effective amount of a compound will vary with the particular compound chosen (e.g. considering the potency, efficacy, and/or half-life of the compound); the route of administration chosen; the condition being treated; the severity of the condition being treated; the age, size, weight, and physical condition of the subject being treated; the medical history of the subject being treated; the duration of the treatment; the nature of a concurrent therapy; the desired therapeutic effect; and like factors and can be routinely determined by the skilled artisan.

The compounds disclosed herein may be administered by any suitable route including oral and parenteral administration. Parenteral administration is typically by injection or infusion and includes intravenous, intramuscular, and subcutaneous injection or infusion.

The compounds disclosed herein may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound disclosed herein depend on the pharmacokinetic properties of that compound, such as absorption, distribution and half-life which can be determined by a skilled artisan. In addition, suitable dosing regimens, including the duration such regimens are administered, for a compound disclosed herein depend on the disease or condition being treated, the severity of the disease or condition, the age and physical condition of the subject being treated, the medical history of the subject being treated, the nature of concurrent therapy, the desired therapeutic effect, and like factors within the knowledge and expertise of the skilled artisan. It will be further understood by such skilled artisans that suitable dosing regimens may require adjustment given an individual subject's response to the dosing regimen or over time as the individual subject needs change. Typical daily dosages may vary depending upon the particular route of administration chosen. Typical daily dosages for oral administration, to a human weighing approximately 70 kg would range from about 0.1 mg to about 2 grams, or more specifically, 0.1 mg to 500 mg, or even more specifically, 0.2 mg to 100 mg, of a compound disclosed herein.

One embodiment of the present invention provides for a method of treating a disease or disorder associated with IDO enzyme activity comprising administration of an effective amount of a compound disclosed herein to a subject in need of treatment thereof. In one embodiment, the disease or disorder associated with an IDO enzyme is a cell proliferation disorder.

In one embodiment, disclosed herein is the use of a compound disclosed herein in a therapy. The compound may be useful in a method of inhibiting IDO enzyme activity in a subject, such as a mammal in need of such inhibition, comprising administering an effective amount of the compound to the subject.

In one embodiment, disclosed herein is a pharmaceutical composition comprising a compound disclosed herein, or a pharmaceutically acceptable salt, solvate or hydrate thereof, for use in potential treatment of a disorder or disease related to IDO enzyme activity.

Compositions

The term "composition" as used herein is intended to encompass a dosage form comprising a specified compound in a specified amount, as well as any dosage form which results, directly or indirectly, from combination of a specified compound in a specified amount. Such term is intended to encompass a dosage form comprising a compound disclosed herein, or a pharmaceutically acceptable salt, solvate or hydrate thereof, and one or more pharmaceutically acceptable carriers or excipients. Accordingly, the compositions of the present invention encompass any composition made by admixing a compound of the present invention and one or more pharmaceutically acceptable carrier or excipients. By "pharmaceutically acceptable" it is meant the carriers or excipients are compatible with the compound disclosed herein and with other ingredients of the composition.

In one embodiment, disclosed herein is a composition comprising a compound disclosed herein, or a pharmaceutically acceptable salt, solvate or hydrate thereof, and one or more pharmaceutically acceptable carriers or excipients. The composition may be prepared and packaged in bulk form wherein an effective amount of a compound of the invention can be extracted and then given to a subject, such as with powders or syrups. Alternatively, the composition may be prepared and packaged in unit dosage form wherein each physically discrete unit contains an effective amount of a compound disclosed herein. When prepared in unit dosage form, the composition of the invention typically contains from about 0.1 mg to 2 grams, or more specifically, 0.1 mg to 500 mg, or even more specifically, 0.2 mg to 100 mg, of a compound disclosed herein, or a pharmaceutically acceptable salt, solvate or hydrate thereof.

A compound disclosed herein and a pharmaceutically acceptable carrier or excipient(s) will typically be formulated into a dosage form adapted for administration to a subject by a desired route of administration. For example, dosage forms include those adapted for (1) oral administration, such as tablets, capsules, caplets, pills, troches, powders, syrups, elixirs, suspensions, solutions, emulsions, sachets, and cachets; and (2) parenteral administration, such as sterile solutions, suspensions, and powders for reconstitution. Suitable pharmaceutically acceptable carriers or excipients will vary depending upon the particular dosage form chosen. In addition, suitable pharmaceutically acceptable carriers or excipients may be chosen for a particular function that they may serve in the composition. For example, certain pharmaceutically acceptable carriers or excipients may be chosen for their ability to facilitate the production of uniform dosage forms. Certain pharmaceutically acceptable carriers or excipients may be chosen for their ability to facilitate the production of stable dosage forms. Certain pharmaceutically acceptable carriers or excipients may be chosen for their ability to facilitate the carrying or transporting of a compound disclosed herein, once administered to the subject, from one organ or portion of the body to another organ or another portion of the body. Certain pharmaceutically acceptable carriers or excipients may be chosen for their ability to enhance patient compliance.

Suitable pharmaceutically acceptable excipients include the following types of excipients: diluents, lubricants, binders, disintegrants, fillers, glidants, granulating agents, coating agents, wetting agents, solvents, co-solvents, suspending agents, emulsifiers, sweeteners, flavoring agents, flavor masking agents, coloring agents, anti-caking agents, hemectants, chelating agents, plasticizers, viscosity increasing agents, antioxidants, preservatives, stabilizers, surfactants, and buffering agents.

A skilled artisan possesses the knowledge and skill in the art to select suitable pharmaceutically acceptable carriers and excipients in appropriate amounts for the use in the invention. In addition, there are a number of resources available to the skilled artisan, which describe pharmaceutically acceptable carriers and excipients and may be useful in selecting suitable pharmaceutically acceptable carriers and excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The compositions of the invention are prepared using techniques and methods known to those skilled in the art. Some methods commonly used in the art are described in Remington's Pharmaceutical Sciences (Mack Publishing Company).

In one embodiment, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives, (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch) gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as, for example, by coating or embedding particulate material in polymers, wax, or the like.

The compounds disclosed herein may also be coupled with soluble polymers as targetable drug carriers. Such polymers can include polyvinylpyrrolidone, pyrancopolymer, polyhydroxypropylmethacrylamidephenol, polyhydroxyethylaspartamidephenol, or polyethyleneoxidepolylysine substituted with palmitoyl residues. Furthermore, the compounds of the invention may be coupled to a class of biodegradable polymers useful in achieving controlled release of a drug, for example polylactic acid, polepsilon caprolactone, polyhydroxy butyric acid, polyorthoesters, polyacetals, polydihydropyrans, polycyanacrylates and cross-linked or amphipathic block copolymers of hydrogels.

In one embodiment, the invention is directed to a liquid oral dosage form. Oral liquids such as solution, syrups and elixirs can be prepared in dosage unit form so that a given quantity contains a predetermined amount of a compound disclosed herein. Syrups can be prepared by dissolving the compound of the invention in a suitably flavored aqueous solution; while elixirs are prepared through the use of a non-toxic alcoholic vehicle. Suspensions can be formulated by dispersing a compound disclosed herein in a non-toxic vehicle. Solubilizers and emulsifiers such as ethoxylated isostearyl alcohols and polyoxy ethylene sorbitol ethers, preservatives, flavor additives such as peppermint oil or other natural sweeteners or saccharin or other artificial sweeteners and the like can also be added.

In one embodiment, the invention is directed to compositions for parenteral administration. Compositions adapted for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Combinations

A compound disclosed herein may be used in combination with one or more other active agents, including but not limited to, other anti-cancer agents, that are used in the prevention, treatment, control, amelioration, or reduction of risk of a particular disease or condition (e.g., cell proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, contemporaneously or sequentially with a compound of the present invention.

When a compound disclosed herein is used contemporaneously with one or more other active agents, a composition containing such other active agents in addition to the compound disclosed herein is contemplated. Accordingly, the compositions of the present invention include those that also contain one or more other active ingredients, in addition to a compound disclosed herein. A compound disclosed herein may be administered either simultaneously with, or before or after, one or more other therapeutic agent(s). A compound disclosed herein may be administered separately, by the same or different route of administration, or together in the same pharmaceutical composition as the other agent(s).

Products provided as a combined preparation include a composition comprising a compound disclosed herein and one or more other active agent(s) together in the same pharmaceutical composition, or a compound disclosed herein, and one or more other therapeutic agent(s) in separate form, e.g. in the form of a kit.

The weight ratio of a compound disclosed herein to a second active agent may be varied and will depend upon the effective dose of each agent. Generally, an effective dose of each will be used. Thus, for example, when a compound disclosed herein is combined with another agent, the weight ratio of the compound disclosed herein to the other agent will generally range from about 1000:1 to about 1:1000, such as about 200:1 to about 1:200. Combinations of a compound disclosed herein and other active agents will generally also be within the aforementioned range, but in each case, an effective dose of each active agent should be used. In such combinations, the compound disclosed herein and other active agents may be administered separately or in conjunction. In addition, the administration of one element may be prior to, concurrent to, or subsequent to the administration of other agent(s).

In one embodiment, the invention provides a composition comprising a compound disclosed herein, and at least one other therapeutic agent as a combined preparation for simultaneous, separate or sequential use in therapy. In one embodiment, the therapy is the treatment of a disease or disorder associated with IDO enzyme activity.

In one embodiment, the invention provides a kit comprising two or more separate pharmaceutical compositions, at least one of which contains a compound disclosed herein. In one embodiment, the kit comprises means for separately retaining said compositions, such as a container, divided bottle, or divided foil packet. An example of such a kit is a blister pack, as typically used for the packaging of tablets, capsules and the like.

A kit disclosed herein may be used for administering different dosage forms, for example, oral and parenteral, for administering the separate compositions at different dosage intervals, or for titrating the separate compositions against one another. To assist with compliance, a kit of the invention typically comprises directions for administration.

Disclosed herein is a use of a compound disclosed herein, for treating a disease or disorder associated with IDO enzyme activity, wherein the medicament is prepared for administration with another active agent. The invention also provides the use of another active agent for treating a disease or disorder associated with an IDO enzyme, wherein the medicament is administered with a compound disclosed herein.

The invention also provides the use of a compound disclosed herein for treating a disease or disorder associated with IDO enzyme activity, wherein the patient has previously (e.g. within 24 hours) been treated with another active agent. The invention also provides the use of another therapeutic agent for treating a disease or disorder associated with IDO enzyme activity, wherein the patient has previously (e.g. within 24 hours) been treated with a compound disclosed herein. The second agent may be applied a week, several weeks, a month, or several months after the administration of a compound disclosed herein.

In one embodiment, the other active agent is selected from the group consisting of vascular endothelial growth factor (VEGF) receptor inhibitors, topoisomerase II inhibitors, smoothen inhibitors, alkylating agents, anti-tumor antibiotics, anti-metabolites, retinoids, immunomodulatory agents including but not limited to anti-cancer vaccines, CTLA-4, LAG-3 and PD-1 antagonists.

Examples of vascular endothelial growth factor (VEGF) receptor inhibitors include, but are not limited to, bevacizumab (sold under the trademark AVASTIN by Genentech/Roche), axitinib, (N-methyl-2-[[3-[([pound])-2-pyridin-2-ylethenyl]-1H-indazol-6-yl]sulfanyl]benzamide, also known as AG013736, and described in PCT Publication No. WO 01/002369), Brivanib Alaninate ((S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, also known as BMS-582664), motesanib (N-(2,3-dihydro-3,3-dimethyl-1H-indoi-6-yl)-2-[(4-pyridinyimethyj)amino]-3-pyfidinecarboxamide. and described in PCT Publication No. WO 02/068470), pasireotide (also known as SO 230, and described in PCT Publication No. WO 02/010192), and sorafenib (sold under the tradename NEXAVAR).

Examples of topoisomerase II inhibitors, include but are not limited to, etoposide (also known as VP-16 and Etoposide phosphate, sold under the tradenames TOPOSAR, VEPESID and ETOPOPHOS), and teniposide (also known as VM-26, sold under the tradename VUMON).

Examples of alkylating agents, include, but are not limited to, 5-azacytidine (sold under the trade name VIDAZA), decitabine (sold under the trade name of DECOGEN), temozolomide (sold under the trade names TEMODAR and TEMODAL by Schering-Plough/Merck), dactinomycin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMM), sold under the tradename HEXALEN), carmustine (sold under the tradename BCNU), bendamustine (sold under the tradename TREANDA), busulfan (sold under the tradenames BUSULFEX and MYLERAN), carboplatin (sold under the tradename PARAPLATIN), lomustine (also known as CCNU, sold under the tradename CeeNU), cisplatin (also known as CDDP, sold under the tradenames PLATINOL and PLATINOL-AQ), chlorambucil (sold under the tradename LEUKERAN), cyclophosphamide (sold under the tradenames CYTOXAN and NEOSAR), dacarbazine (also known as DTIC, DIC and imidazole carboxamide, sold under the tradename DTIC-DOME), altretamine (also known as hexamethylmelamine (HMM) sold under the tradename HEXALEN), ifosfamide (sold under the tradename IFEX), procarbazine (sold under the tradename MATULANE), mechlorethamine (also known as nitrogen mustard, mustine and mechloroethamine hydrochloride, sold under the tradename MUSTARGEN), streptozocin (sold under the tradename ZANOSAR), thiotepa (also known as thiophosphoamide, TESPA and TSPA, and sold under the tradename THIOPLEX).

Examples of anti-tumor antibiotics include, but are not limited to, doxorubicin (sold under the tradenames ADRIAMYCIN and RUBEX), bleomycin (sold under the tradename LENOXANE), daunorubicin (also known as dauorubicin hydrochloride, daunomycin, and rubidomycin hydrochloride, sold under the tradename CERUBIDINE), daunorubicin liposomal (daunorubicin citrate liposome, sold under the tradename DAUNOXOME), mitoxantrone (also known as DHAD, sold under the tradename NOVANTRONE), epirubicin (sold under the tradename ELLENCE), idarubicin (sold under the tradenames IDAMYCIN, IDAMYCIN PFS), and mitomycin C (sold under the tradename MUTAMYCIN).

Examples of anti-metabolites include, but are not limited to, claribine (2-chlorodeoxyadenosine, sold under the tradename LEUSTATIN), 5-fluorouracil (sold under the tradename ADRUCIL), 6-thioguanine (sold under the tradename PURINETHOL), pemetrexed (sold under the tradename ALIMTA), cytarabine (also known as arabinosylcytosine (Ara-C), sold under the tradename CYTOSAR-U), cytarabine liposomal (also known as Liposomal Ara-C, sold under the tradename DEPOCYT), decitabine (sold under the tradename DACOGEN), hydroxyurea (sold under the tradenames HYDREA, DROXIA and MYLOCEL), fludarabine (sold under the tradename FLUDARA), floxuridine (sold under the tradename FUDR), cladribine (also known as 2-chlorodeoxyadenosine (2-CdA) sold under the tradename LEUSTATIN), methotrexate (also known as amethopterin, methotrexate sodium (MTX), sold under the tradenames RHEUMATREX and TREXALL), and pentostatin (sold under the tradename NIPENT).

Examples of retinoids include, but are not limited to, alitretinoin (sold under the tradename PANRETIN), tretinoin (all-trans retinoic acid, also known as ATRA, sold under the tradename VESANOID), Isotretinoin (13-c/s-retinoic acid, sold under the tradenames ACCUTANE, AMNESTEEM, CLARAVIS, CLARUS, DECUTAN, ISOTANE, IZOTECH, ORATANE, ISOTRET, and SOTRET), and bexarotene (sold under the tradename TARGRETIN).

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. In any of the treatment method, medicaments and uses of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the treatment method, medicaments and uses of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments. Examples of PD-1 and PD-L1 antagonists include, but are not limited to, pembrolizumab (sold under the tradename KEYTRUDA), nivolumab (sold under the tradename OPDIVO), AND atezolizumab (sold under the trade name TECENTRIQ).

Examples of mAbs that bind to human PD-1, and useful in the treatment method, medicaments and uses of the present invention, are described in U.S. Pat. Nos. 7,488,802, 7,521,051, 8,008,449, 8,354,509, 8,168,757, WO2004/004771, WO2004/072286, WO2004/056875, and US2011/0271358.

Examples of mAbs that bind to human PD-L1, and useful in the treatment method, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MEDI4736, MSB0010718C and an antibody which comprises the heavy chain and light chain variable regions of SEQ ID NO:24 and SEQ ID NO:21, respectively, of WO2013/019906.

Other PD-1 antagonists useful in any of the treatment method, medicaments and uses of the present invention include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

Examples of other cytotoxic agents include, but are not limited to, arsenic trioxide (sold under the tradename TRISENOX), asparaginase (also known as L-asparaginase, and Erwinia L-asparaginase, sold under the tradenames ELSPAR and KIDROLASE).

EXPERIMENTAL

The following synthetic schemes and examples are intended to be illustrative only and not limiting in any way. Abbreviations used are those conventional in the art or the following.

ACN acetonitrile
aq. Aqueous
Boc tert-butyloxycarbonyl
Boc$_2$O di-tert-butyl dicarbonate
Calc'd calculated
Celite diatomaceous earth used as a filtration medium
CO carbon monoxide
Cu(I)I copper(I) iodide
CV column volume
° C. degree celsius
CPhos Pd G4 [(2-dicyclohexylphosphino-2',6'-bis(N,N-dimethylamino)-1,1'-biphenyl)-2-(2'-methylamino-1,1'-biphenyl)] palladium(II) methanesulfonate
CV column volume(s)
DAST (dimethylamino)sulfur trifluoride
DCM dichloromethane
DIEA N,N-diisopropylethylamine
DIPEA N,N-diisopropylethylamine
DMA dimethylamine
DMF N,N-dimethylformamide
DMSO dimethylsulfoxide
DPPA diphenylphosphoryl azide
DPPF 1,1'-bis(diphenylphosphino)ferrocene
EDC N-(3-dimethylaminopropyl)-N'-ethylcarbodiimide hydrochloride
EI electron ionization
EMEM Eagle's minimal essential medium
Et ethyl
Et$_2$O diethyl ether
Et$_3$N triethylamine
EtOAc ethyl acetate EtOH ethanol
g gram
h hour(s)
HATU 1-[bis(dimethylamino)methylene]-1H-1,2,3-triazolo[4,5-b]pyridinium 3-oxid-hexafluorophosphate
HCl hydrochloric acid
HPLC high pressure liquid chromatography
JackiePhos Pd G3 [(2-{Bis[3,5-bis(trifluoromethyl)phenyl]phosphine}-3,6-dimethoxy-2',4',6'-triisopropyl-1,1'-biphenyl)-2-(2'-amino-1,1'-biphenyl)]palladium(II) methanesulfonate
JohnPhos (2-biphenyl)di-tert-butylphosphine
$K_3PO_4$ potassium phosphate tribasic
kg kilogram
KO'Bu potassium tert-butoxide
L liter
LC liquid chromatography
LCMS liquid chromatography and mass spectrometry
LiHMDS lithium bis(trimethylsilyl)amide
LiOH lithium hydroxide
M molar
Me methyl
MeOH methanol
mg miligram
mmol milimole
MS mass spectrometry
MTBE methyl tert-butyl ether
min minutes
mL milliliter(s)
m/z mass to charge ratio
nm nanometer
nM nanomolar
N normal
$N_2$ nitrogen
$Na_2SO_4$ sodium sulfate
NaH sodium hydride
$NaHCO_3$ sodium bicarbonate
NaHMDS sodium bis(trimethylsilyl)amide
$NaN_3$ sodium azide
NaOH sodium Hydroxide
NBS N-bromosuccinimide
$NH_4Cl$ ammonium chloride $Pd_2(dba)_3$ tris(dibenzylideneacetone)dipalladium(0)
$Pd(dppf)_2Cl_2$ [1,1'-Bis(diphenylphosphino)ferrocene]dichloropalladium(II)
$PdCl_2(dtbpf)$ [1,1'-Bis(di-tert-butylphosphino)ferrocene]dichloropalladium(II)
PE petroleum ether
PG protecting group
$PMBNH_2$ p-methoxybenzylamine
PMP P-methoxyphenyl
$POCl_3$ phosphorus oxychloride
PS polystyrene
RPMI Roswell Park Memorial Institute
RT or rt room temperature
sat. saturated
$T_3P$ propylphosphonic anhydride solution
t-BuOH tert-butanol
TEA triethyl amine
TFA trifluoroacetic acid
THF tetrahydrofuran
TLC thin layer chromatography
uL microliter(s)
XPhos Pd G2 chloro(2-dicyclohexylphosphino-2',4',6'-triisopropyl-1,1'-biphenyl)[2-(2'-amino-1,1'-biphenyl)]palladium(II)

General Synthetic Schemes

The compounds of formula (I) may be prepared by methods known in the art of organic synthesis as set forth in part by the following synthetic schemes and synthetic procedures and conditions for the illustrative intermediates and examples.

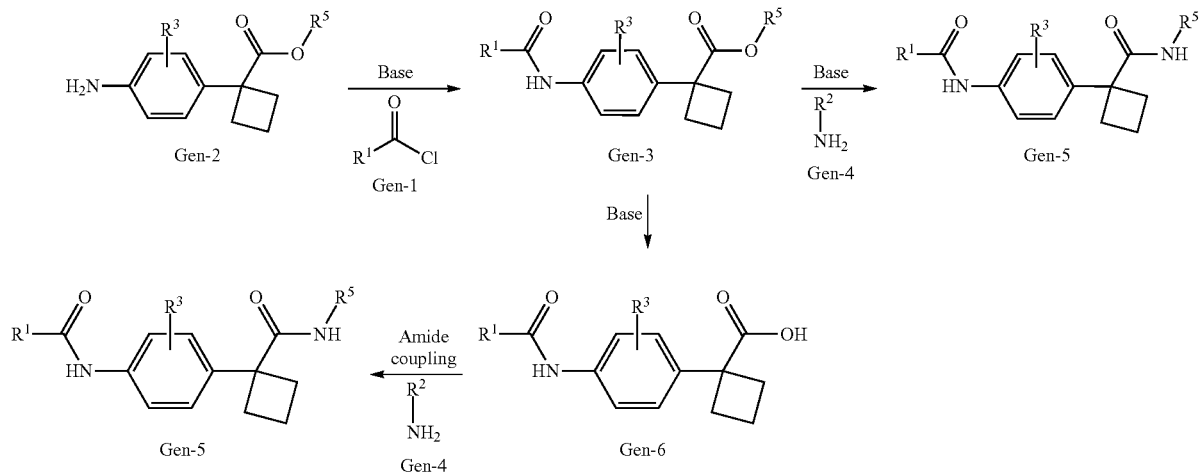

Scheme 1

$R^5$ = Me, Et

In scheme 1, commercially available amine Gen-2, where $R^5$=Me, Et (for example, ethyl 1-(4-aminophenyl)cyclobutane-1-carboxylate), is elaborated to Gen-3 by treatment with Gen-1 and a base (for example, TEA). Treatment of Gen-3 with Gen-4 and a base (for example, potassium tert-butoxide) affords Gen-5. Conversely, Gen-3 can be treated with a base (for example, NaOH) to afford Gen-6. Gen-6 can undergo amide coupling (for example, with HATU/DIEA) with Gen-4 to afford Gen-5.

Scheme 2

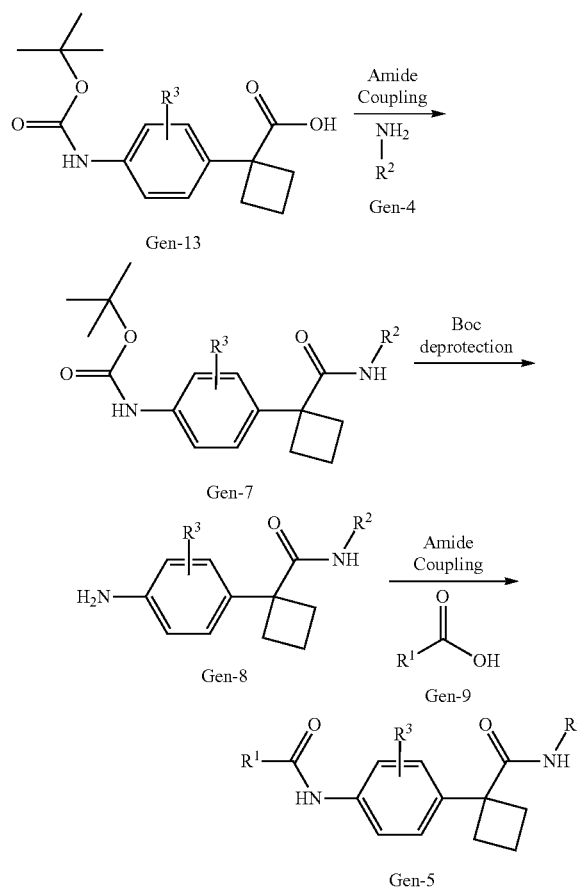

In scheme 2, commercially available carboxylic acid Gen-13 (for example, 1-(4-(((tert-butoxycarbonyl)amino)phenyl)cyclobutane-1-carboxylic acid) is elaborated to Gen-7 through amide coupling (for example, with HATU/DIEA) with Gen-4. Boc deprotection (for example, with 4.0 M HCl) of Gen-7 affords Gen-8. Gen-8 and Gen-9 undergo amide coupling (for example, with HATU/DIEA) to afford Gen-5.

X = Br, Cl
$R^5$ = Me, Et

In scheme 3, commercially available Gen-15, where X=Br, Cl and $R^5$=Me, Et (for example, methyl 1-(4-bromophenyl)-3-hydroxycyclobutane-1-carboxylate), is cross coupled (for example, with JackiePhos Pd G3) with commercially available Gen-16 (for example, 3-chlorobenzamide) to afford Gen-17. Fluorination of Gen-17 (for example, with DAST) affords Gen-18. Treatment of Gen-18 with a base (for example, NaOH) affords Gen-19. Amide coupling (for example, HATU/DIEA) of Gen-19 with Gen-4 affords Gen-20.

Scheme 3

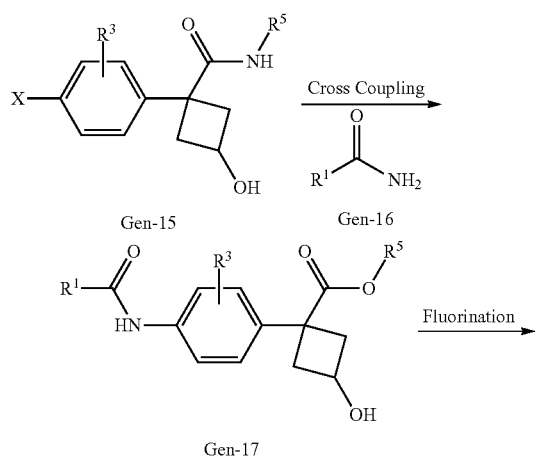

Scheme 4

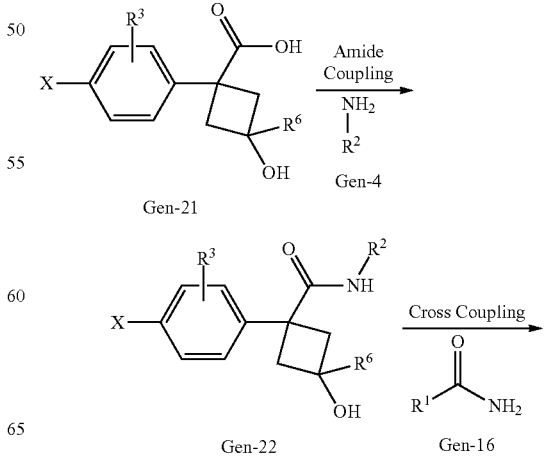

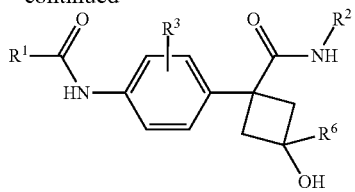

Gen-82

X = Br, Cl; R⁶ = H, Me

In scheme 4, commercially available carboxylic acid Gen-21, where X=Br, Cl and $R^6$=H, Me (for example, (1s,3s)-1-(4-bromophenyl)-3-hydroxycyclobutane-1-carboxylic acid), is elaborated to Gen-22 through amide coupling (for example, with HATU/DIEA) with Gen-4. Cross coupling (for example, with JackiePhos Pd G3) of Gen-22 with Gen-16 affords Gen-82.

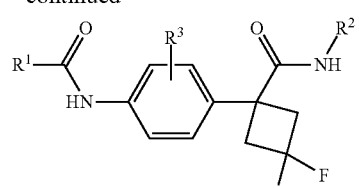

Gen-29

X = Cl, Br
$R^5$ = Me, Et

In scheme 5, commercially available Gen-81, where X=Br, Cl and $R^5$=Me, Et (for example, methyl 1-(4-chlorophenyl)cyclobutane-1-carboxylate), is fluorinated (for example, with DAST) to afford Gen-25. Amine formation affords Gen-26. Treatment of Gen-26 with a base (for example, with TEA) and Gen-1 affords Gen-27. Treatment of Gen-27 with a base (for example, with NaOH) affords Gen-28. Amide coupling (for example, with HATU/DIEA) of Gen-28 with Gen-4 affords Gen-29.

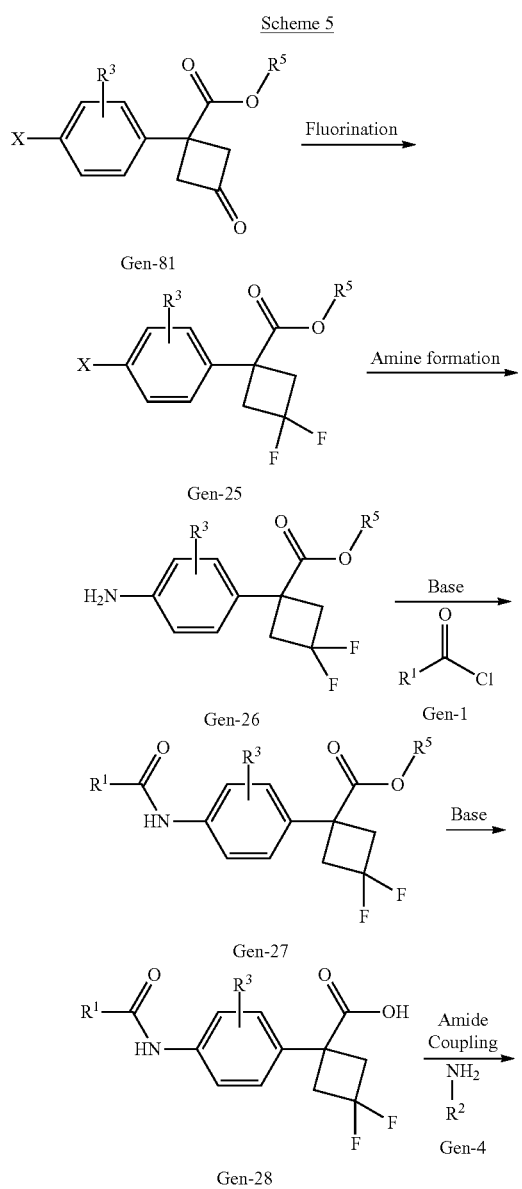

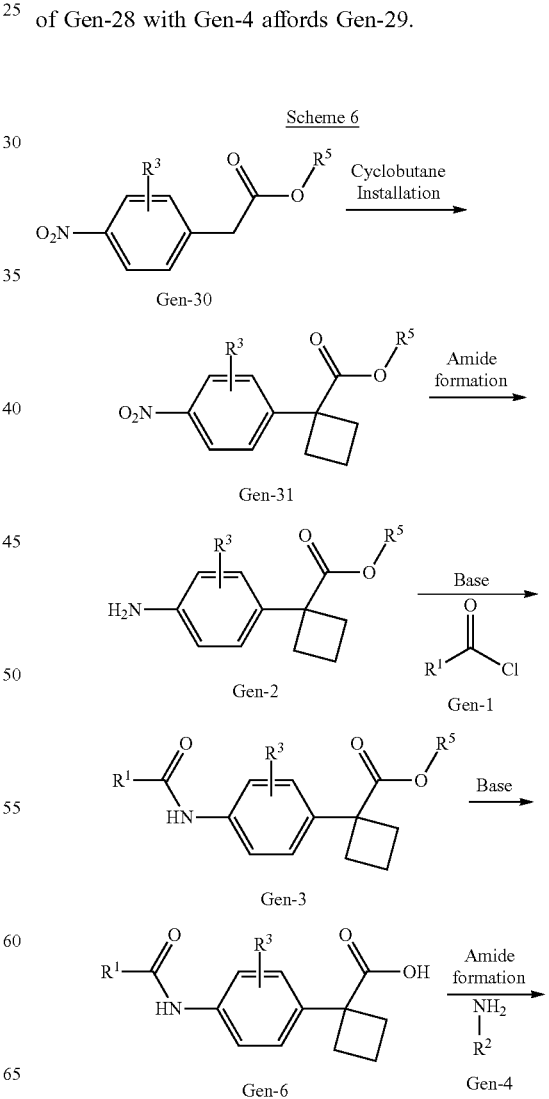

31
-continued

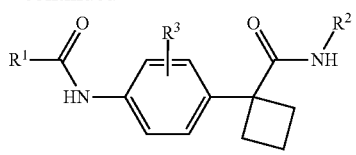

Gen-5

R⁵ = Me, Et

In scheme 6, commercially available Gen-30, where R⁵=Me, Et (for example, methyl 2-(4-nitrophenyl)acetate), is elaborated to Gen-31 through cyclobutane installation. Gen-31 is converted to the corresponding amine (for example, with SnCl₂) Gen-2. Gen-2 is elaborated to Gen-3 through treatment with Gen-1 and a base (for example, TEA). Gen-3 is treated with a base (for example, NaOH) to afford Gen-6. Gen-6 undergoes amide formation (for example, with HATU/DIEA) with Gen-4 to afford Gen-5.

32
-continued

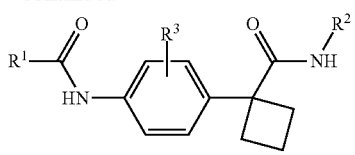

Gen-5

In scheme 7, commercially available Gen-48 (for example, 2-(4-nitrophenyl)acetonitrile) is elaborated to Gen-57 through cyclobutane installation. Treatment of Gen-57 with a base (for example, KOH) affords Gen-34. Gen-34 is converted to acid chloride Gen-58 (through treatment with oxalyl chloride, for example). Gen-58 is converted to Gen-59 by treatment with a base (for example, TEA) and Gen-4. Nitro reduction (for example, with Pd/C) of Gen-59 affords Gen-60. Gen-60 and Gen-1 are treated with a base (for example, TEA) to afford Gen-5.

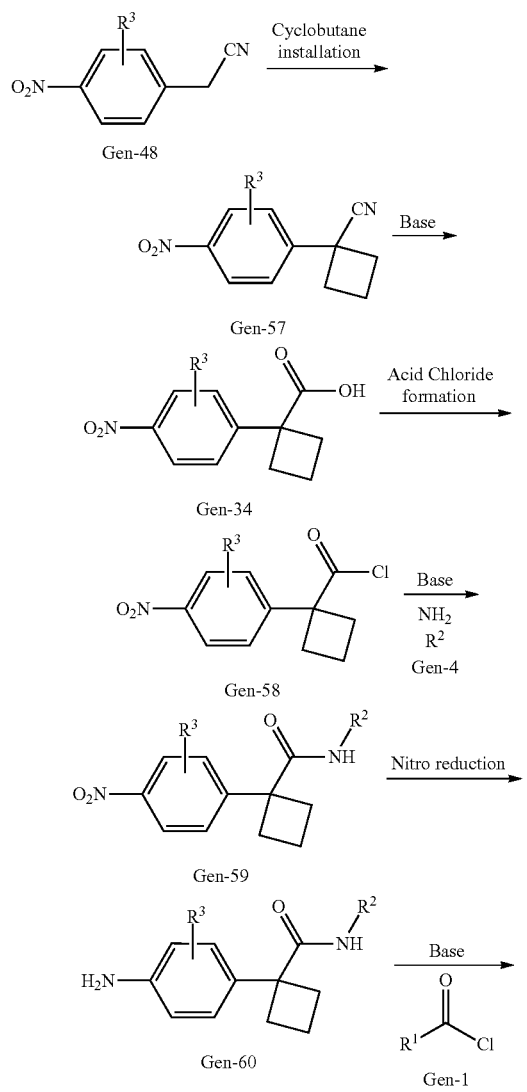

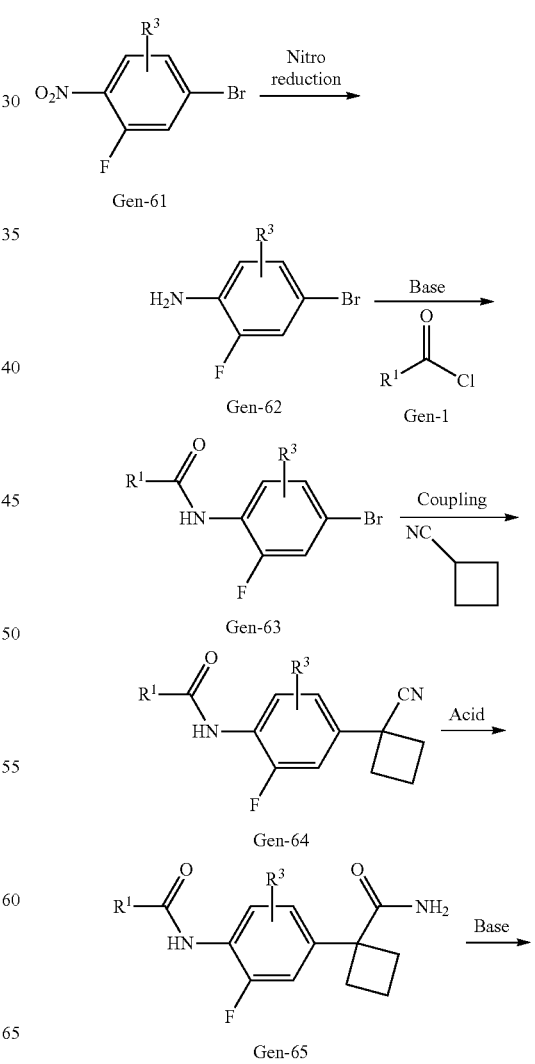

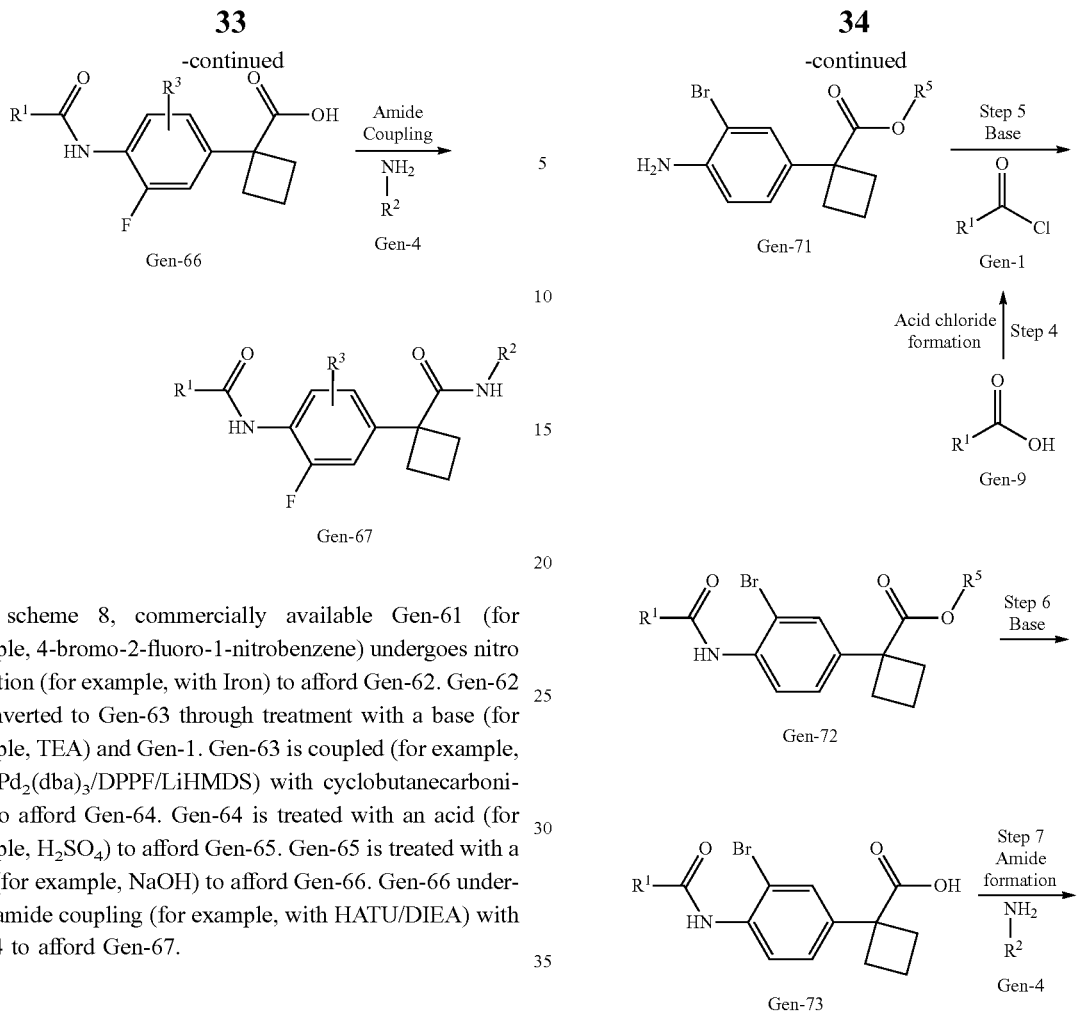

In scheme 8, commercially available Gen-61 (for example, 4-bromo-2-fluoro-1-nitrobenzene) undergoes nitro reduction (for example, with Iron) to afford Gen-62. Gen-62 is converted to Gen-63 through treatment with a base (for example, TEA) and Gen-1. Gen-63 is coupled (for example, with Pd$_2$(dba)$_3$/DPPF/LiHMDS) with cyclobutanecarbonitrile to afford Gen-64. Gen-64 is treated with an acid (for example, H$_2$SO$_4$) to afford Gen-65. Gen-65 is treated with a base (for example, NaOH) to afford Gen-66. Gen-66 undergoes amide coupling (for example, with HATU/DIEA) with Gen-4 to afford Gen-67.

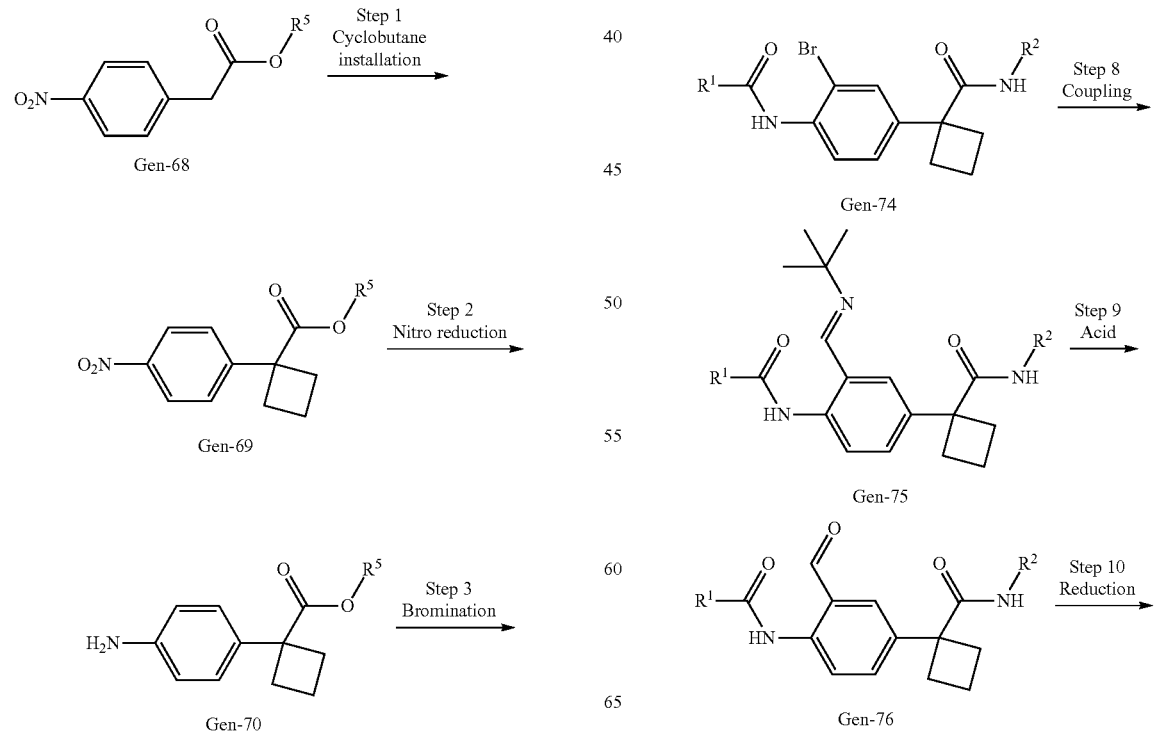

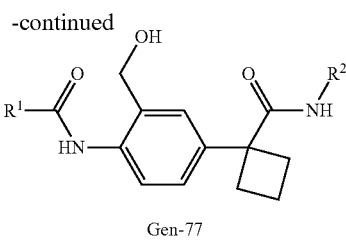

Gen-77

$R^5$ = Me, Et

In scheme 9, commercially available Gen-68, where $R^5$=Me, Et (for example, ethyl 2-(4-nitrophenyl)acetate), is elaborated to Gen-69 through cyclobutane installation. Nitro reduction (for example, with Iron) of Gen-69 affords Gen-70. Gen-70 is brominated (for example, with NBS) to afford Gen-71. Gen-9 is converted to Gen-1 (through treatment with, for example, oxalyl chloride). Gen-1 and Gen-71 are treated with a base (for example, TEA) to afford Gen-72. Gen-72 is treated with a base (for example, LiOH) to afford Gen-73. Gen-73 and Gen-4 undergo amide coupling (for example, with HATU/DIEA) to afford Gen-74. Gen-74 is elaborated to Gen-75 under coupling conditions (for example, with Pd(OAc)$_2$ and JohnPhos). Gen-75 is treated with an acid (for example, HCl) to afford Gen-76. Reduction of Gen-76 (with, for example NaBH$_4$) affords Gen-77.

In scheme 10, Gen-34 and Gen-4 undergo amide formation (for example, with 1. Oxalyl chloride; 2. TEA) to afford Gen-83. Nitro reduction (for example, with Pd/C) of Gen-83 affords Gen-60. Gen-60 and Gen-9 undergo amide formation (for example, with 1. Oxalyl chloride; 2. TEA) to afford Gen-5.

Scheme 10

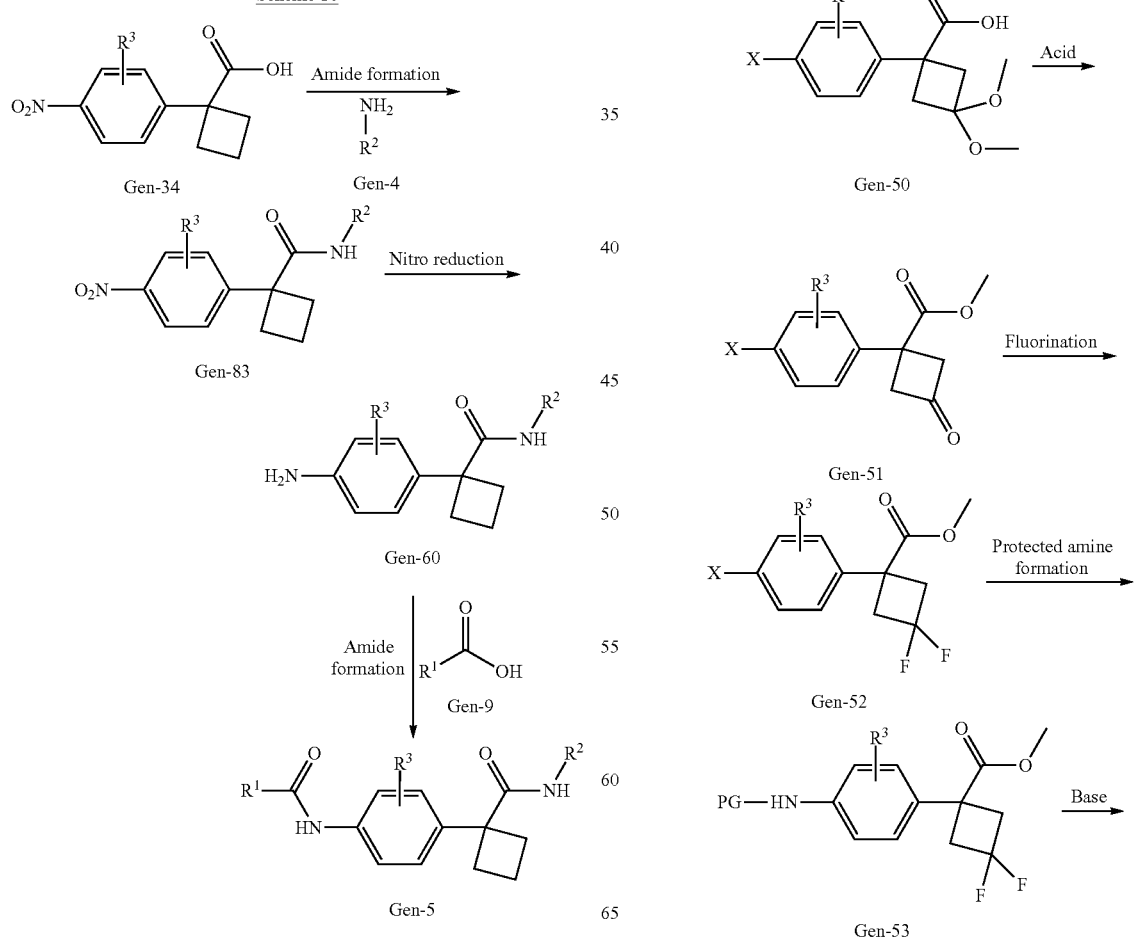

Scheme 11

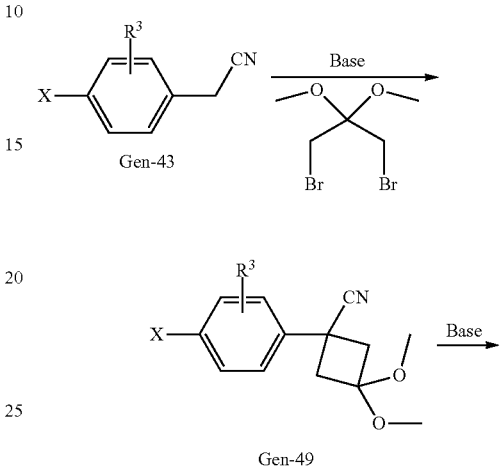

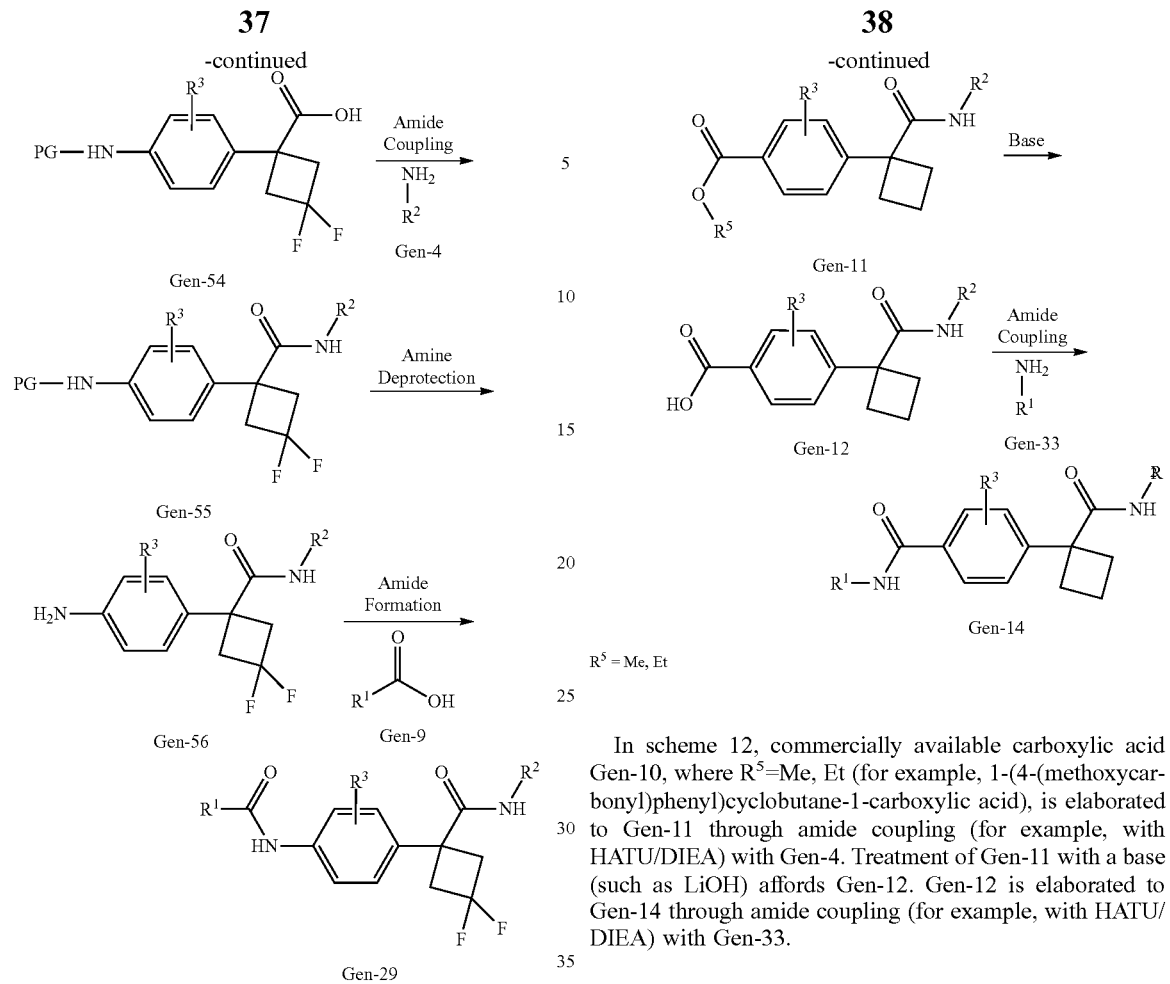

In scheme 11, commercially available Gen-43, where X=Br, Cl (for example, 2-(4-bromophenyl)acetonitrile), is treated with a base (for example, NaH) and 1,3-dibromo-2,2-dimethoxypropane to afford Gen-49. Gen-49 is treated with a base (for example, NaOH) to afford Gen-50. Gen-50 is treated with an acid (for example, $H_2SO_4$) to afford Gen-51. Gen-51 is fluorinated (for example, with DAST) to afford Gen-52. Gen-52 is converted to a protected amine (for example, PMP protected amine) to afford Gen-53. Gen-53 is treated with a base (for example, LiOH) to afford Gen-54. Gen-54 undergoes amide coupling (for example, with HATU/DIEA) with Gen-4 to afford Gen-55. Gen-55 is deprotected (with, for example Pd/C) to afford Gen-56. Gen-56 undergoes amide formation (for example, with $POCl_3$) with Gen-9 to afford Gen-29.

Scheme 12

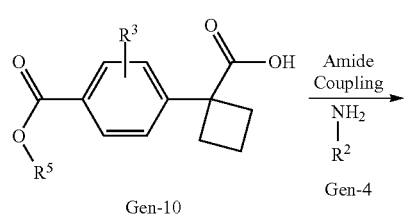

Gen-10

In scheme 12, commercially available carboxylic acid Gen-10, where $R^5$=Me, Et (for example, 1-(4-(methoxycarbonyl)phenyl)cyclobutane-1-carboxylic acid), is elaborated to Gen-11 through amide coupling (for example, with HATU/DIEA) with Gen-4. Treatment of Gen-11 with a base (such as LiOH) affords Gen-12. Gen-12 is elaborated to Gen-14 through amide coupling (for example, with HATU/DIEA) with Gen-33.

Scheme 13

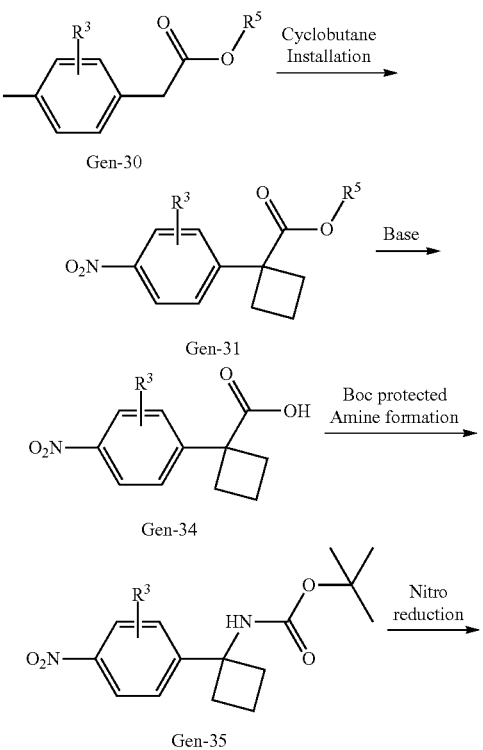

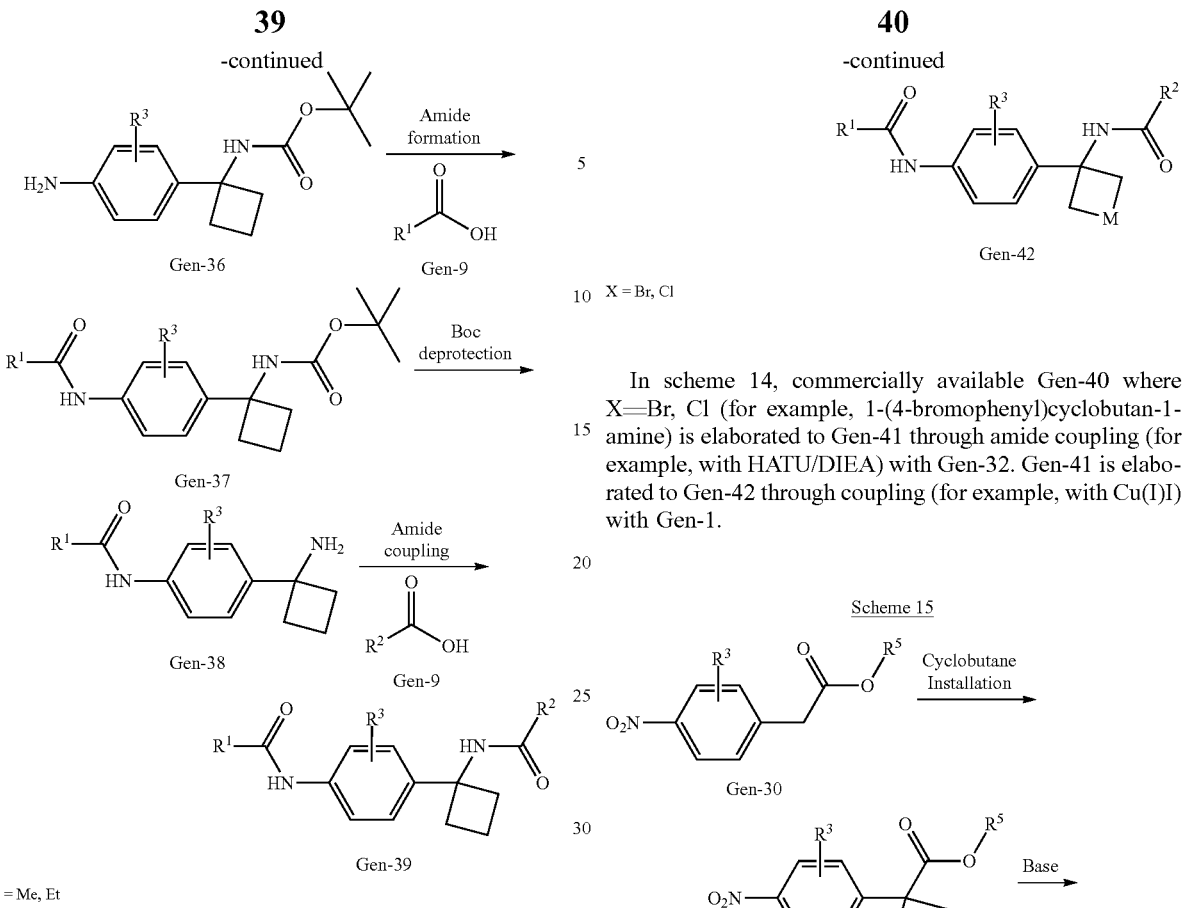

In scheme 13, commercially available Gen-30, where $R^5$=Me, Et (for example, ethyl 2-(4-nitrophenyl)acetate), is converted to Gen-31 through the installation of cyclobutane (for example, with NaH and 1,3-diiodopropane). Treatment of Gen-31 with a base (for example, LiOH) affords Gen-34. Gen-34 is converted (for example, via DPPA/TEA) to a boc protected amine Gen-35. Nitro reduction of Gen-35 (for example, with Iron) affords Gen-36. Gen-36 is converted to amide Gen-37 (for example, via $T_3P$/pyridine) with addition of Gen-9. Gen-37 is converted to Gen-38 through boc deprotection (for example, with HCl). Gen-38 is elaborated to Gen-39 through amide coupling (for example, HATU/DIEA) with Gen-9.

In scheme 14, commercially available Gen-40 where X=Br, Cl (for example, 1-(4-bromophenyl)cyclobutan-1-amine) is elaborated to Gen-41 through amide coupling (for example, with HATU/DIEA) with Gen-32. Gen-41 is elaborated to Gen-42 through coupling (for example, with Cu(I)I) with Gen-1.

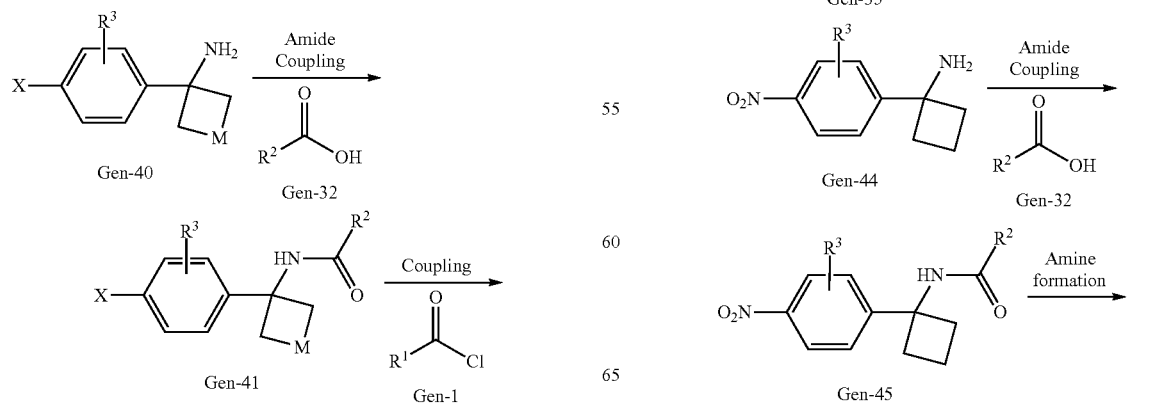

-continued

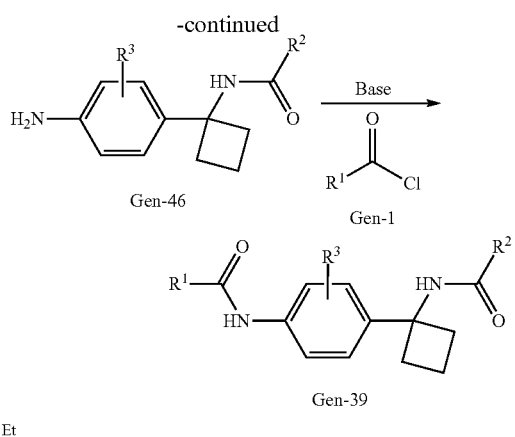

$R^5$ = Me, Et

In scheme 15, commercially available Gen-30, where $R^5$=Me, Et (for example, ethyl 2-(4-nitrophenyl)acetate), is converted to Gen-31 through the installation of cyclobutane (for example, with NaH and 1,3-diiodopropane). Treatment of Gen-31 with a base (for example, LiOH) affords Gen-34. Gen-34 is converted (for example, via DPPA/TEA) to a boc protected amine Gen-35. Gen-35 undergoes boc deprotection (for example, with HCl) to afford Gen-44. Gen-44 is elaborated to Gen-45 through amide coupling (for example, with HATU/DIEA) with Gen-32. Gen-45 is converted to the corresponding amine (for example, with treatment with Iron/$NH_4Cl$), Gen-46. Gen-46 is treated with a base (for example, TEA) and Gen-1 to afford Gen-39.

Scheme 16

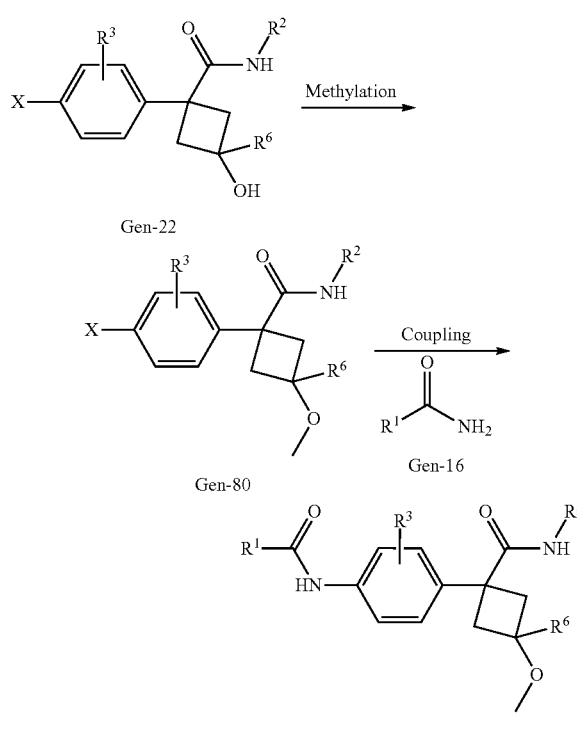

X = Br, Cl
$R^6$ = H, Me

In scheme 16, Gen-22 (see scheme 4) is methylated to afford Gen-80. Gen-80 undergoes cross coupling (for example, with JackiePhos Pd G3) with Gen-16 to afford Gen-84.

Standard purification procedures referenced in the following examples are provided below.

Purification A: TFA (Acidic) Conditions/Chromatography and Mass Spectrometry

Isolation of a compound from the reaction mixture was carried out under reverse-phase purification using an Agilent 1200 HPLC-MSD system consisting of a 6130B single quadrupole mass-selective detector (MSD), G1315B diode array detector (DAD), G2258A autosampler, two G1361A preparative pumps, one G1379A quaternary pump with degasser, one G1312A binary pump, and three G1364B fraction collectors from Agilent Technologies (Agilent Technologies, Palo Alto, Calif.). System control and data analysis were performed using Agilent's ChemStation software, revision B.04.03. A Waters SunFire C18 OBD Prep Column, 100 Å, 5 µm, 19 mm×150 mm column was used as the stationary phase (Waters Corporation, Milford, Mass., USA). Gradient elution was carried out using water (solvent A) and acetonitrile (solvent B) as a mobile phase. A 10% trifluoroacetic acid solution was added into the mobile phase as a modifier using a static mixer prior to the column, pumped at 1% of the total mobile phase flowrate. Electrospray (ESI) Mass-triggered fraction collected was employed using positive ion polarity scanning to monitor for the target mass.

HPLC Gradient:

| Time (min) | % Acetonitrile | Mobile Phase Flowrate (mL/Min) | Modifier Flowrate (mL/min) |
|---|---|---|---|
| 0.0 | 2 | 25 | 0.25 |
| 3.0 | 2 | 35 | 0.35 |
| 33.0 | 95 | 35 | 0.35 |
| 33.1 | 100 | 40 | 0.4 |
| 36.1 | 100 | 50 | 0.5 |
| 36.8/end | 2 | 25 | 0.2 |

Purification B: TFA (Acidic) Condition/Chromatography and Mass Spectrometry

Isolation of a compound from the reaction mixture was carried out under reverse-phase purification using a Gilson system consisting of UV-156 detector, GX281 liquid handler, 322 pumps. An Agela ASB 150*25 mm*5 m column was used as the stationary phase. Gradient elution was carried out using water (solvent A) and acetonitrile (solvent B) as a mobile phase. A 0.1% trifluoroacetic acid solution was added into the mobile phase (solvent A) as a modifier.

HPLC Gradient:

| Time (min) | % Acetonitrile | Mobile Phase Flowrate (mL/Min) |
|---|---|---|
| 0.0 | 37 | 25 |
| 1.0 | 37 | 25 |
| 10.0 | 52 | 25 |
| 10.2 | 100 | 25 |
| 12.5 | 100 | 25 |
| 12.7/end | 5 | 25 |

Purification C: TFA (Acidic) Condition/Chromatography and Mass Spectrometry

Isolation of a compound from the reaction mixture was carried out under reverse-phase purification using a Gilson system consisting of UV-156 detector, GX281 liquid handler, 322 pumps. An Agela ASB 150*25 mm*5 m column was used as the stationary phase. Gradient elution was carried out using water (solvent A) and acetonitrile (solvent B) as a mobile phase. A 0.2% trifluoroacetic acid solution was teed into the mobile phase (solvent A) as a modifier.

HPLC Gradient:

| Time (min) | % Acetonitrile | Mobile Phase Flowrate (mL/Min) |
|---|---|---|
| 0.0 | 37 | 25 |
| 1.0 | 37 | 25 |
| 10.0 | 52 | 25 |
| 10.2 | 100 | 25 |
| 12.5 | 100 | 25 |
| 12.7/end | 5 | 25 |

Purification D: Formic Acid (Acidic) Condition/Chromatography and Mass Spectrometry Isolation of a compound from the reaction mixture was carried out under reverse-phase purification using a Gilson system consisting of UV-156 detector, GX281 liquid handler, 322 pumps. An Agela ASB 150*25 mm*5 µm column was used as the stationary phase. Gradient elution was carried out using water (solvent A) and acetonitrile (solvent B) as a mobile phase. A 0.2% formic acid solution was teed into the mobile phase (solvent A) as a modifier.

HPLC Gradient:

| Time (min) | % Acetonitrile | Mobile Phase Flowrate (mL/Min) |
|---|---|---|
| 0.0 | 37 | 25 |
| 1.0 | 37 | 25 |
| 10.0 | 52 | 25 |
| 10.2 | 100 | 25 |
| 12.5 | 100 | 25 |
| 12.7/end | 5 | 25 |

EXAMPLES

Example 1: N-(4-(1-Butyramidocyclobutyl)phenyl)-3-chlorobenzamide

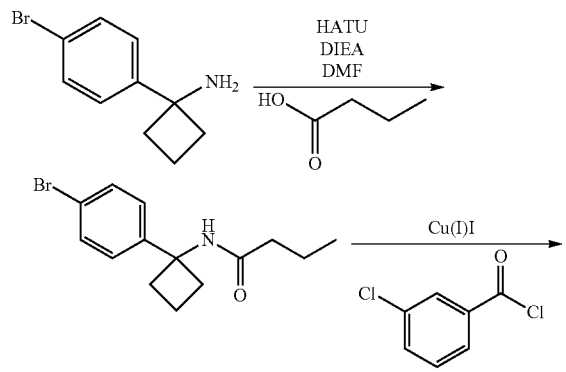

-continued

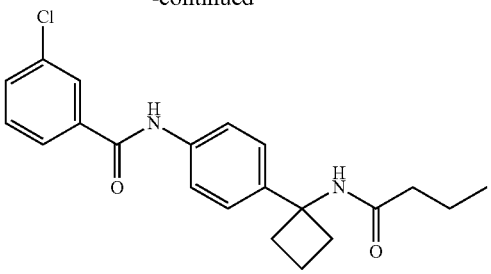

Example 1

Step 1: Preparation of N-(1-(4-bromophenyl)cyclobutyl)butyramide

To a vial containing butyric acid (52 µl, 0.57 mmol) and HATU (280 mg, 0.74 mmol) was added DMF (2100 µl). The reaction mixture was allowed to stir at RT for 5 min, before a solution of 1-(4-bromophenyl)cyclobutanamine (150 mg, 0.64 mmol) in DMF (710 µl) was added, followed by DIPEA (350 µl, 2.0 mmol). The reaction mixture was stirred at RT for 5 days, then partitioned between EtOAc and saturated NaHCO$_3$. The organic layer was dried over anhydrous magnesium sulfate, filtered, and concentrated under reduced pressure to afford N-(1-(4-bromophenyl)cyclobutyl)butyramide. MS ESI calc'd. [M+H]$^+$ 296, found 296.

Step 2: Preparation of N-(4-(1-butyramidocyclobutyl)phenyl)-3-chlorobenzamide

To a vial equipped with a stir bar was added N-(1-(4-bromophenyl)cyclobutyl)butyramide (30 mg, 0.10 mmol), cesium carbonate (99 mg, 0.30 mmol), 3-chlorobenzamide (15 mg, 0.099 mmol), (1S,2S)—N1,N2-dimethylcyclohexane-1,2-diamine (2.9 mg, 0.020 mmol), and dioxane (510 µl). The reaction mixture was purged with nitrogen, before copper(I) iodide (1.9 mg, 10 µmol) was added. The reaction mixture was purged with nitrogen for 3 min. The vial was sealed and heated to 110° C. for 25 h. The crude reaction mixture was cooled to RT, dissolved in methanol and filtered over Celite. The filtrate was concentrated under reduced pressure. The resulting residue was purified by column chromatography on silica (0-100% EtOAc/hexanes) to afford N-(4-(1-butyramidocyclobutyl)phenyl)-3-chlorobenzamide. The material was then dissolved in DMSO (1 ml), filtered, and purified under Purification A conditions to afford the title compound. MS ESI calc'd. [M+H]$^+$ 370, found 393 (M+Na$^+$). $^1$H NMR (400 MHz, DMSO-d$_6$) δ 10.34 (s, 1H), 8.44 (s, 1H), 8.04 (s, 1H), 7.95 (d, J=7.7 Hz, 1H), 7.70 (d, J=8.4 Hz, 2H), 7.61 (t, J=7.9 Hz, 1H), 7.39 (d, J=8.5 Hz, 2H), 2.46 (t, J=7.5 Hz, 3H), 2.09 (t, J=7.2 Hz, 2H), 2.05-1.96 (m, 1H), 1.90-1.77 (m, 1H), 1.56-1.47 (m, 2H), 0.87 (t, J=7.4 Hz, 3H).

Example 2: 3-Chloro-N-(4-(1-(4-cyanobenzamido)cyclobutyl)phenyl)benzamide

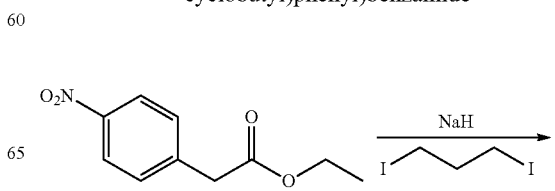

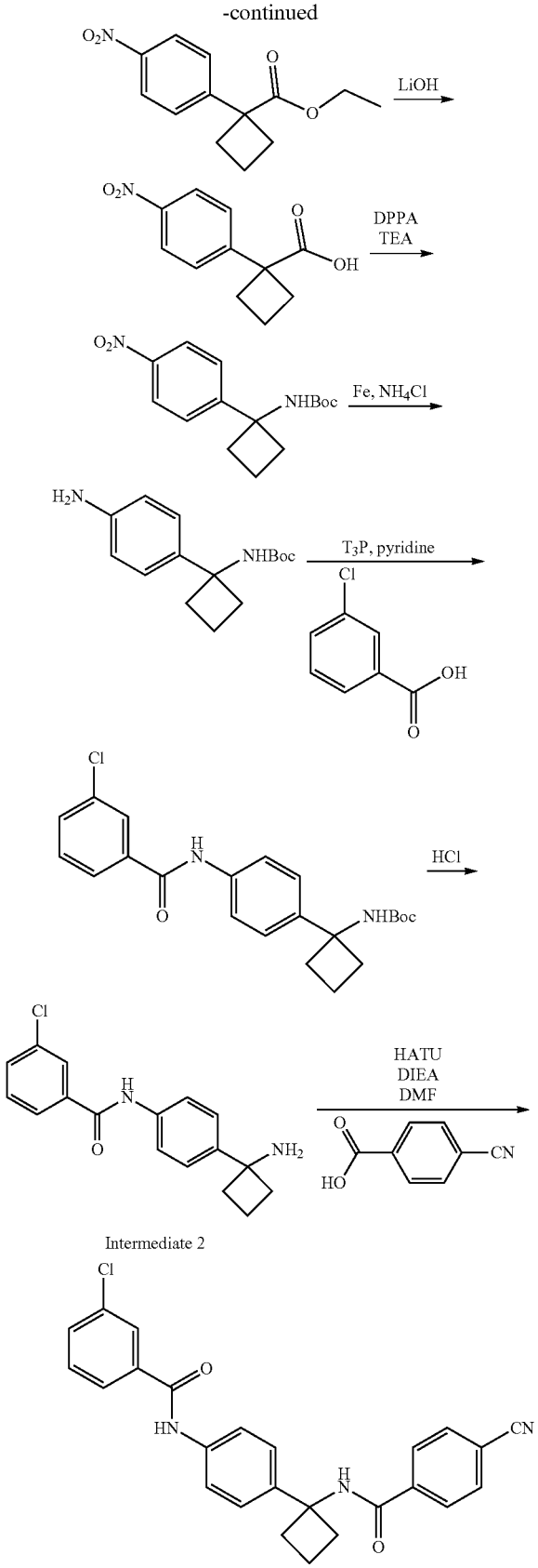

Intermediate 2

Example 2

Step 1: Preparation of ethyl 1-(4-nitrophenyl)cyclobutanecarboxylate

To a solution of ethyl 2-(4-nitrophenyl)acetate (9 g, 43 mmol) in DMF (100 mL) was added NaH (3.6 g, 90 mmol) (60% in oil) at 0° C. The reaction mixture was allowed to warm to RT and was stirred for 15 min. The mixture was cooled to 0° C. and 1,3-diiodopropane (10 mL, 89 mmol) was added. The resulting mixture was stirred at 0° C. for 30 min, then warmed to RT. After 1 h the reaction mixture was diluted with aqueous NH$_4$Cl (200 mL), and was extracted with EtOAc (200 mL×3). The combined organics were washed with brine (1000 mL), dried over saturated Na$_2$SO$_4$, filtered and concentrated under reduced pressure. The residue was purified by silica gel chromatography (SiO$_2$, petroleum ether/EtOAc=50:1 to 40:1) to afford ethyl 1-(4-nitrophenyl)cyclobutanecarboxylate.

Step 2: Preparation of 1-(4-nitrophenyl)cyclobutanecarboxylic Acid

To a solution of ethyl 1-(4-nitrophenyl)cyclobutanecarboxylate (6.6 g, 26 mmol) in THF (80 mL)/MeOH (80 mL)/water (40 mL) was added lithium hydroxide hydrate (3.3 g, 79 mmol) at RT. The reaction was stirred at RT for 15 h then concentrated under reduced pressure. The residue was acidified to pH ~5 with 3 M HCl then extracted with EtOAc (100 mL×3). The combined organics were washed with brine (50 mL), dried over anhydrous Na$_2$SO$_4$, filtered, and concentrated under reduced pressure. The residue was purified by silica column chromatography (petroleum ether:EtOAc=4:1) to afford 1-(4-nitrophenyl)cyclobutanecarboxylic acid.

Step 3: Preparation of tert-butyl (1-(4-nitrophenyl)cyclobutyl)carbamate (Intermediate 1)

To a solution of 1-(4-nitrophenyl)cyclobutanecarboxylic acid (3.9 g, 18 mmol) in t-BuOH (80 mL) was added TEA (3.7 mL, 27 mmol) and diphenyl phosphorazidate (5.6 g, 21 mmol) while stirring at RT. The reaction mixture was heated and stirred at 85° C. under N$_2$ for 2 h, cooled to RT, and concentrated under reduced pressure. The residue was purified by silica gel column chromatography (petroleum ether:ethyl acetate=20:1) to afford tert-butyl (1-(4-nitrophenyl)cyclobutyl)carbamate.

Step 4: Preparation of tert-butyl (1-(4-aminophenyl)cyclobutyl)carbamate

To a stirred solution of tert-butyl (1-(4-nitrophenyl)cyclobutyl)carbamate (3.7 g, 13 mmol) (Intermediate 1) in ethanol (50 mL) and water (5 mL) was added iron (3.5 g, 63 mmol) and NH$_4$Cl (6.8 g, 130 mmol). The reaction mixture was stirred at 90° C. for 3 h, cooled to RT, and filtered through a pad of Celite. The filtrate was concentrated under reduced pressure. The residue was dissolved in DCM (150 mL), and washed with water (100 mL) and brine (50 mL). The organic layer was dried over anhydrous Na$_2$SO$_4$, filtered, and concentrated under reduced pressure. The residue was purified by silica column chromatography (petroleum ether:EtOAc=5:1) to afford tert-butyl (1-(4-aminophenyl)cyclo-butyl)carbamate.

Step 5: Preparation of tert-butyl (1-(4-(3-chlorobenzamido)phenyl)cyclobutyl)carbamate To a stirred solution of 3-chlorobenzoic acid (2.1 g, 14 mmol) in THF (100 mL) was added tert-butyl (1-(4-aminophenyl)cyclobutyl)carbamate (3.0 g, 11 mmol), 2,4,6-tripropyl-1,3,5,2,4,6-trioxatriphosphinane 2,4,6-trioxide (15 g, 22.87 mmol) (50% in the EtOAc), and pyridine (2.77 mL, 34 mmol). The reaction mixture was stirred at RT for 3 h, then concentrated under reduced pressure. The residue was dissolved in DCM (100 mL), washed with water (100 mL), and the organic layer was concentrated under reduced pressure to afford tert-butyl (1-(4-(3-chlorobenzamido)phenyl)cyclobutyl)carbamate.

Step 6: Preparation of N-(4-(1-aminocyclobutyl)phenyl)-3-chlorobenzamide (Intermediate 2)

To a solution of tert-butyl (1-(4-(3-chlorobenzamido)phenyl)cyclobutyl)carbamate (1.6 g, 3.99 mmol) in 1,4-dioxane (20 mL) was added hydrogen chloride (30 mL, 120 mmol) (4M in dioxane) drop wise while stirring at RT. The reaction mixture was allowed to stir at RT for 15 h, then concentrated under reduced pressure. The residue was purified under Purification B conditions to afford N-(4-(1-aminocyclobutyl)phenyl)-3-chlorobenzamide.

Step 7: Preparation of 3-Chloro-N-(4-(1-(4-cyanobenzamido)cyclobutyl)phenyl)benzamide To a vial equipped with a stir bar was added 4-cyanobenzoic acid (14 mg, 0.083 mmol) in DMF (1.0 ml) and HATU (38 mg, 0.10 mmol). The reaction mixture was stirred for 5 min before N-(4-(1-aminocyclobutyl)phenyl)-3-chlorobenzamide (25 mg, 0.083 mmol) (Intermediate 2) was added, followed by DIEA (0.044 ml, 0.25 mmol). The reaction mixture was stirred for 12 h at RT, and was then filtered and purified under Purification A conditions to afford the title compound. MS ESI calc'd. $[M+H]^+$ 430, found 430. $^1$H NMR (500 MHz, DMSO-$d_6$) δ 10.31 (s, 1H), 8.51 (s, 1H), 8.00 (s, 1H), 7.90 (s, 1H), 7.74 (s, 1H), 7.66 (s, 3H), 7.56 (s, 1H), 7.43 (s, 2H), 6.53 (s, 1H), 3.37 (s, 2H), 2.62 (s, 2H), 1.97 (s, 1H), 1.79 (s, 1H).

Examples 3-17 in Table 1 were prepared in an analogous way to Example 2, using the corresponding carboxylic acid. Example 18 can be prepared in an analogous way to Example 2, using T$_3$P and pyridine in the final step with the corresponding carboxylic acids.

TABLE 1

| Ex. # | Structure | Chemical Name | Mass [M + H]+ |
|---|---|---|---|
| 3 | 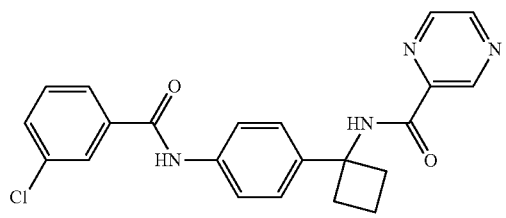 [SMILES: O=C(Nc1ccc(C2(NC(=O)c3cnccn3)CCC2)cc1)c1cccc(Cl)c1] | N-(1-{4-[(3-chlorobenzene-1-carbonyl)amino]phenyl}cyclobutyl)pyrazine-2-carboxamide | 407 |
| 4 | 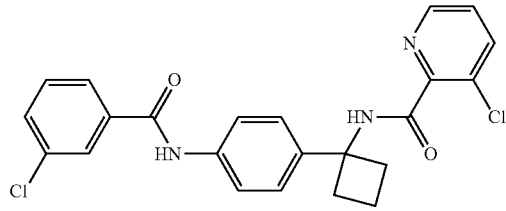 [SMILES: O=C(Nc1ccc(C2(NC(=O)c3ncccc3Cl)CCC2)cc1)c1cccc(Cl)c1] | 3-chloro-N-(1-{4-[(3-chlorobenzene-1-carbonyl)amino]phenyl}cyclobutyl)pyridine-2-carboxamide | 440 |
| 5 | 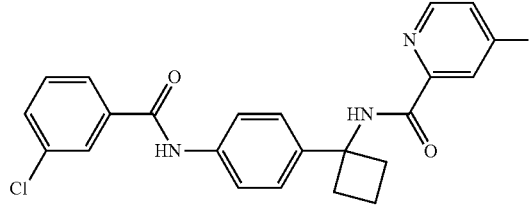 | 4-chloro-N-(1-{4-[(3-chlorobenzene-1-carbonyl)amino]phenyl}cyclobutyl)pyridine-2-carboxamide | 440 |
| 6 | 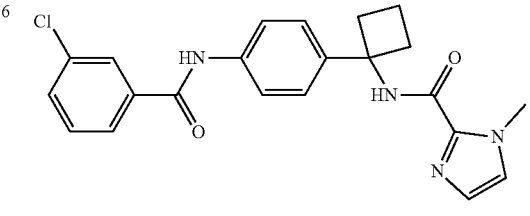 | N-(1-{4-[(3-chlorobenzene-1-carbonyl)amino]phenyl}cyclobutyl)-1-methyl-1H-imidazole-2-carboxamide | 409 |

TABLE 1-continued

| Ex. # | Structure | Chemical Name | Mass [M + H]+ |
|---|---|---|---|
| 7 | 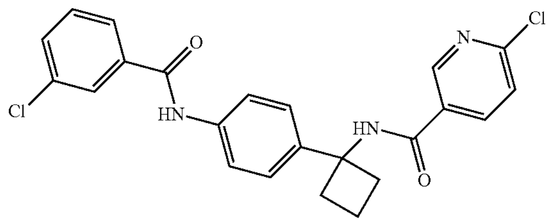 [SMILES: O=C(Nc1ccc(C2(NC(=O)c3ccc(Cl)nc3)CCC2)cc1)c1cccc(Cl)c1] | 6-chloro-N-(1-{4-[(3-chlorobenzene-1-carbonyl)amino]phenyl}cyclobutyl)pyridine-3-carboxamide | 440 |
| 8 | 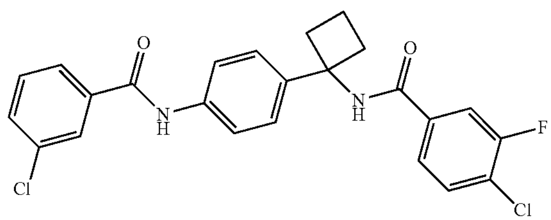 [SMILES: O=C(Nc1ccc(C2(NC(=O)c3ccc(Cl)c(F)c3)CCC2)cc1)c1cccc(Cl)c1] | 4-chloro-N-(1-{4-[(3-chlorobenzene-1-carbonyl)amino]phenyl}cyclobutyl)-3-fluorobenzamide | 457 |
| 9 | 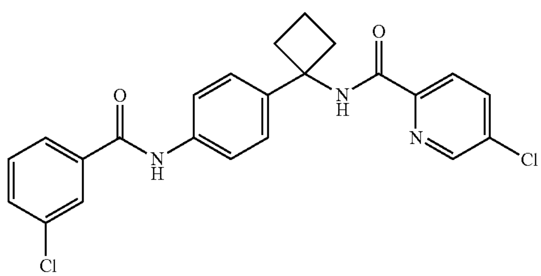 [SMILES: O=C(Nc1ccc(C2(NC(=O)c3ccc(Cl)cn3)CCC2)cc1)c1cccc(Cl)c1] | 5-chloro-N-(1-{4-[(3-chlorobenzene-1-carbonyl)amino]phenyl}cyclobutyl)pyridine-2-carboxamide | 440 |
| 10 | 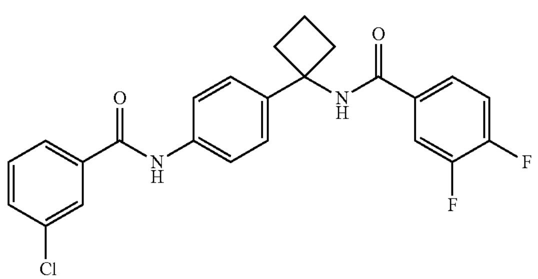 [SMILES: O=C(Nc1ccc(C2(NC(=O)c3ccc(F)c(F)c3)CCC2)cc1)c1cccc(Cl)c1] | N-(1-{4-[(3-chlorobenzene-1-carbonyl)amino]phenyl}cyclobutyl)-3,4-difluorobenzamide | 441 |
| 11 | 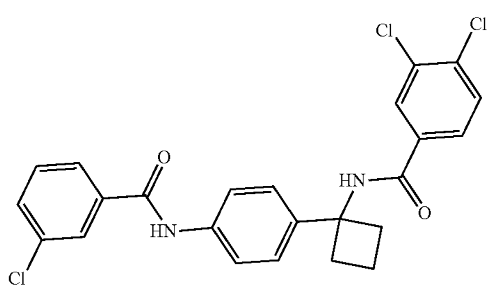 [SMILES: O=C(Nc1ccc(C2(NC(=O)c3ccc(Cl)c(Cl)c3)CCC2)cc1)c1cccc(Cl)c1] | 3,4-dichloro-N-(1-{4-[(3-chlorobenzene-1-carbonyl)amino]phenyl}cyclobutyl)benzamide | 473 |
| 12 | 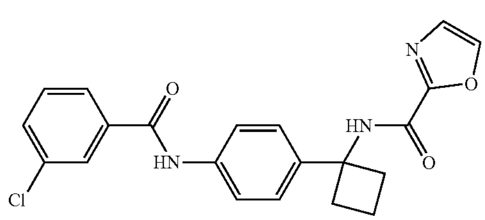 [SMILES: O=C(Nc1ccc(C2(NC(=O)c3ncco3)CCC2)cc1)c1cccc(Cl)c1] | N-(1-{4-[(3-chlorobenzene-1-carbonyl)amino]phenyl}cyclobutyl)-1,3-oxazole-2-carboxamide | 396 |

TABLE 1-continued

| Ex. # | Structure | Chemical Name | Mass [M + H]+ |
|---|---|---|---|
| 13 | 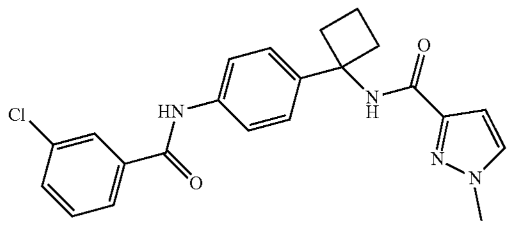 [SMILES: Cn1ccc(C(=O)NC2(c3ccc(NC(=O)c4cccc(Cl)c4)cc3)CCC2)n1] | N-(1-{4-[(3-chlorobenzene-1-carbonyl)amino]phenyl}cyclobutyl)-1-methyl-1H-pyrazole-3-carboxamide | 409 |
| 14 | 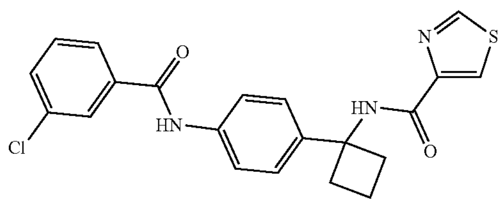 [SMILES: O=C(Nc1ccc(C2(NC(=O)c3cscn3)CCC2)cc1)c1cccc(Cl)c1] | N-(1-{4-[(3-chlorobenzene-1-carbonyl)amino]phenyl}cyclobutyl)-1,3-thiazole-4-carboxamide | 412 |
| 15 | 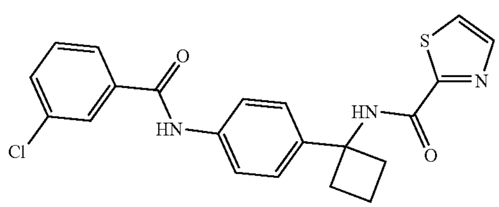 [SMILES: O=C(Nc1ccc(C2(NC(=O)c3nccs3)CCC2)cc1)c1cccc(Cl)c1] | N-(1-{4-[(3-chlorobenzene-1-carbonyl)amino]phenyl}cyclobutyl)-1,3-thiazole-2-carboxamide | 412 |
| 16 | 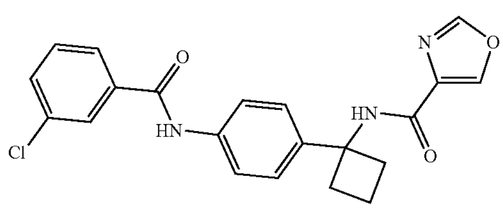 [SMILES: O=C(Nc1ccc(C2(NC(=O)c3cocn3)CCC2)cc1)c1cccc(Cl)c1] | N-(1-{4-[(3-chlorobenzene-1-carbonyl)amino]phenyl}cyclobutyl)-1,3-oxazole-4-carboxamide | 396 |
| 17 | 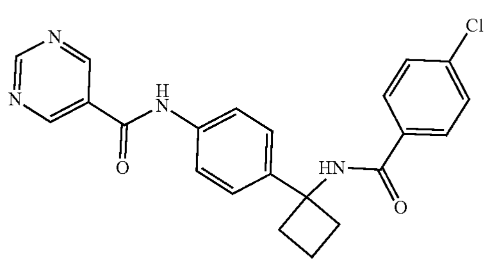 [SMILES: O=C(Nc1ccc(C2(NC(=O)c3ccc(Cl)cc3)CCC2)cc1)c1cncnc1] | N-(4-{1-[(4-chlorobenzene-1-carbonyl)amino]cyclobutyl}phenyl)pyrimidine-5-carboxamide | 407 |
| 18 | 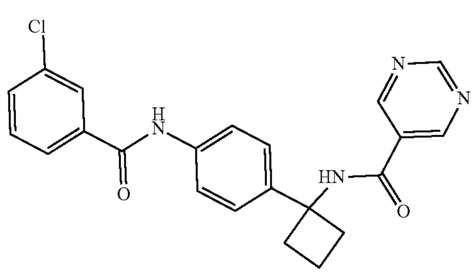 [SMILES: O=C(Nc1ccc(C2(NC(=O)c3cncnc3)CCC2)cc1)c1cccc(Cl)c1] | N-(1-{4-[(3-chlorobenzene-1-carbonyl)amino]phenyl}cyclobutyl)pyrimidine-5-carboxamide | 407 |

Example 19: 3-Chloro-N-(4-(1-(4-chlorobenzamido)cyclobutyl)phenyl)benzamide

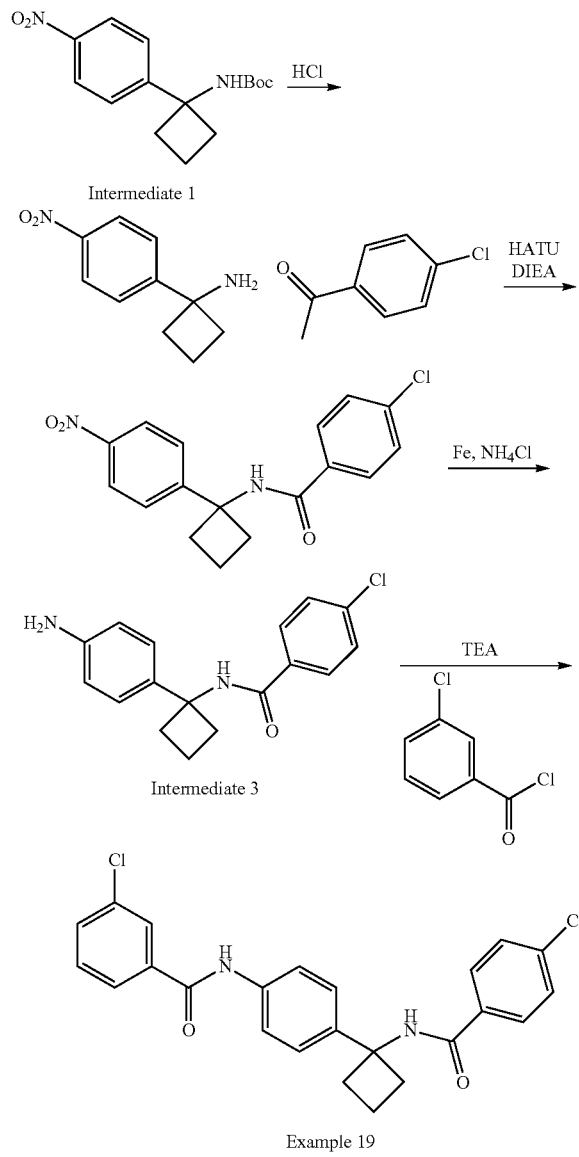

Example 19

Step 1: Preparation of 1-(4-Nitrophenyl)cyclobutan-1-amine

A mixture of tert-butyl (1-(4-nitrophenyl)cyclobutyl)carbamate (Intermediate 1) (250 mg, 0.86 mmol) and HCl (4 mL, 16 mmol) (4M in dioxane) was stirred at RT for 2 h, then concentrated under reduced pressure to afford 1-(4-nitrophenyl)cyclobutanamine hydrochloride.

Step 2: Preparation of 4-chloro-N-(1-(4-nitrophenyl)cyclobutyl)benzamide

To a solution of 1-(4-nitrophenyl)cyclobutanamine hydrochloride (200 mg, 0.86 mmol) in DMF (5 mL) was added HATU (330 mg, 0.87 mmol), 4-chlorobenzoic acid (140 mg, 0.87 mmol) and DIEA (0.6 mL, 3.4 mmol) while stirring at RT. The reaction mixture was allowed to stir for 15 h, and was then diluted with water (30 mL), and extracted with EtOAc (20 mL×3). The combined organics were washed with brine (20 mL), dried over anhydrous $Na_2SO_4$, filtered, and concentrated under reduced pressure. The residue was purified by silica column chromatography (petroleum ether:EtOAc=20:1 to 1:1) to afford 4-chloro-N-(1-(4-nitrophenyl)cyclobutyl)benzamide.

Step 3: Preparation of N-(1-(4-aminophenyl)cyclobutyl)-4-chlorobenzamide (Intermediate 3)

To a stirred solution of 4-chloro-N-(1-(4-nitrophenyl)cyclobutyl)benzamide (150 mg, 0.45 mmol) in EtOH (5 mL)/water (0.5 mL) was added iron (130 mg, 2.3 mmol) and $NH_4Cl$ (240 mg, 4.5 mmol). The reaction was stirred at 90° C. for 2 h, cooled to RT, then filtered through a pad of Celite. The filtrate was concentrated under reduced pressure to afford N-(1-(4-aminophenyl)cyclobutyl)-4-chlorobenzamide. MS ESI calc'd. $[M+H]^+$ 301, found 301.

Step 4: Preparation of 3-chloro-N-(4-(1-(4-chlorobenzamido)cyclobutyl)phenyl)benzamide To a solution of N-(1-(4-aminophenyl)cyclobutyl)-4-chlorobenzamide (130 mg, 0.43 mmol) (Intermediate 3) and TEA (0.2 mL, 1.4 mmol) in DCM (5 mL) was added 3-chlorobenzoyl chloride (150 mg, 0.86 mmol) in DCM (5 mL) at 0° C. The reaction was stirred at 0° C. for 1 h, then concentrated under reduced pressure. The residue was partitioned between water (20 mL) and EtOAc (10 mL×2). The organic layer was dried over anhydrous $Na_2SO_4$, filtered and concentrated under reduced pressure. The residue was purified under Purification B conditions to afford the title compound. MS ESI calc'd. $[M+H]^+$ 439, found 461 $(M+Na^+)$. $^1H$ NMR (400 MHz, DMSO-$d_6$) δ 10.30 (s, 1H), 9.06 (s, 1H), 7.98 (t, J=1.6 Hz, 1H), 7.84-7.91 (m, 3H), 7.62-7.70 (m, 3H), 7.48-7.58 (m, 3H), 7.44 (d, J=8.6 Hz, 2H), 2.51-2.65 (m, 4H), 1.94-2.04 (m, 1H), 1.76-1.89 (m, 1H).

Example 20: 3-Chloro-N-(4-(1-((4-fluorophenyl)carbamoyl)cyclobutyl)phenyl)benzamide

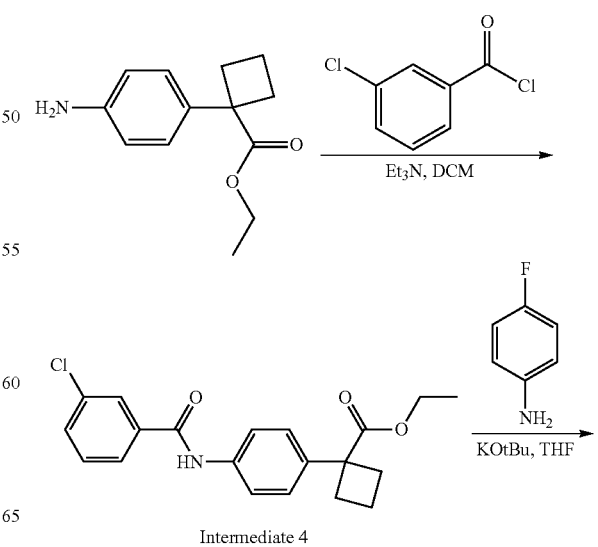

Intermediate 4

-continued

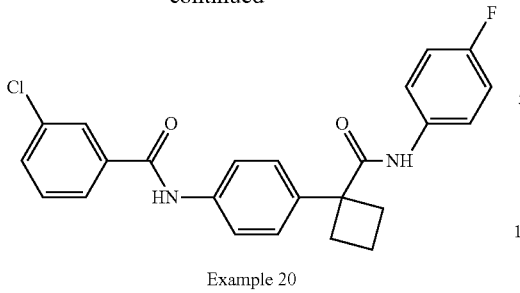

Example 20

Step 1: Preparation of ethyl 1-(4-(3-chlorobenzamido)phenyl)cyclobutane-1-carboxylate (Intermediate 4)

Ethyl 1-(4-aminophenyl)cyclobutanecarboxylate (1050 mg, 4.8 mmol) was dissolved in DCM (20 ml) and cooled to 0° C. using an ice bath. Et$_3$N (1.0 ml, 7.2 mmol) and 3-chlorobenzoyl chloride (0.77 ml, 6.1 mmol) were added to the solution drop wise at 0° C. The mixture was stirred at RT for 18 h. After 18 h the crude reaction mixture was concentrated under reduced pressure and purified on silica gel (100 g flash column, EtOAc in hexane, 0-20%, 5 CV; 20-20%, 10 CV) to afford ethyl 1-(4-(3-chlorobenzamido)phenyl)cyclobutanecarboxylate. MS (ESI) Calc'd [M+H]$^+$, 358; found, 358.

Step 2: Preparation of 3-chloro-N-(4-(1-((4-fluorophenyl)carbamoyl)cyclobutyl)phenyl)benzamide (Compound 20)

To a solution of KOtBu (27 mg, 0.24 mmol) in THF (600 μl) was added ethyl 1-(4-(3-chlorobenzamido)phenyl)cyclobutanecarboxylate (31 mg, 0.087 mmol) (Intermediate 4) and 4-fluoroaniline (10 μl, 0.11 mmol). The mixture was stirred at RT for 20 h. After 20 h the mixture was diluted with MeOH, filtered and purified under Purification A conditions to afford the title compound. MS (ESI) Calc'd [M+H]$^+$, 423; found, 423. $^1$H NMR (600 MHz, DMSO-d$_6$) δ 10.31 (s, 1H), 9.41 (s, 1H), 7.95 (s, 1H), 7.86 (d, J=7.7 Hz, 1H), 7.69 (d, J=8.3 Hz, 2H), 7.62 (d, J=7.8 Hz, 1H), 7.57 (dd, J=8.3, 5.1 Hz, 2H), 7.52 (t, J=7.8 Hz, 1H), 7.40 (d, J=8.3 Hz, 2H), 7.06 (t, J=8.7 Hz, 2H), 2.77 (q, J=8.5 Hz, 2H), 2.41 (q, J=8.7 Hz, 2H), 1.85-1.70 (m, 2H).

Examples 21-23: 1-(4-(3-Chlorobenzamido)phenyl)cyclobutane-1-carboxylic Acid

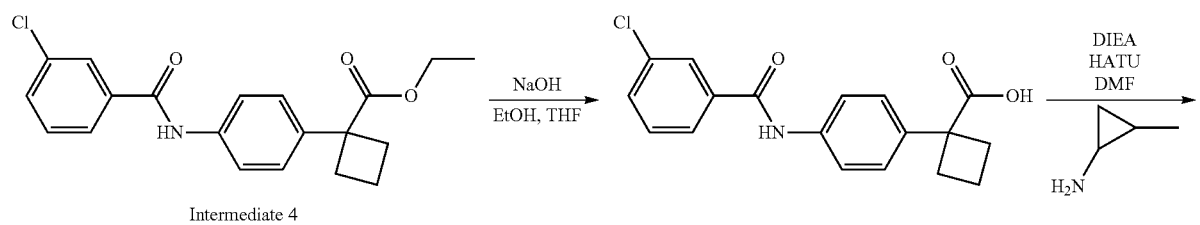

Intermediate 4

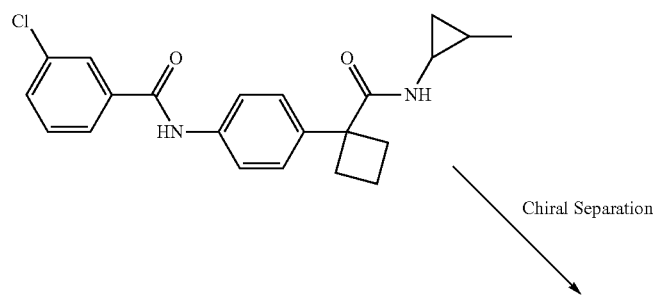

Chiral Separation

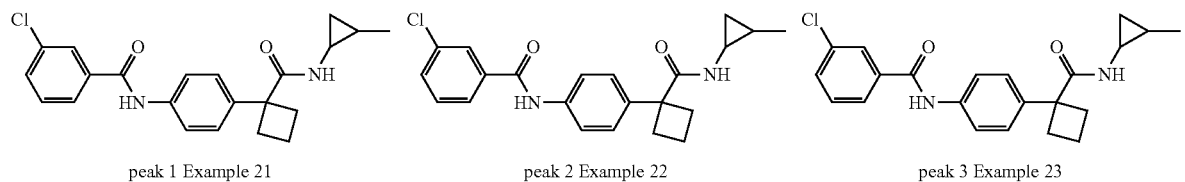

peak 1 Example 21      peak 2 Example 22      peak 3 Example 23

Step 1: Preparation of 1-(4-(3-chlorobenzamido)phenyl)cyclobutane-1-carboxylic Acid To a solution of ethyl 1-(4-(3-chlorobenzamido)phenyl)cyclobutanecarboxylate (1.7 g, 4.7 mmol) (Intermediate 4) in THF (10 ml), was added 1 M NaOH (10 ml, 10 mmol) and ethanol (10 ml). The mixture was stirred at RT for 18 h. An additional 5 ml of NaOH (1M) was added and the reaction was stirred at RT for an additional 18 h. After 18 h the crude reaction mixture was partially concentrated under reduced pressure. To the remaining aqueous solution was added HCl (1 M), to adjust the pH to ~3. The solution was extracted with EtOAc (3 times). The combined organics were washed with brine, dried over anhydrous $Na_2SO_4$, filtered, and concentrated under reduced pressure to afford 1-(4-(3-chlorobenzamido)phenyl)cyclobutanecarboxylic acid. MS (ESI) Calc'd [M+H]$^+$, 330; found, 330.

Step 2: Preparation of 3-chloro-N-(4-(1-((2-methylcyclopropyl)carbamoyl)cyclobutyl)phenyl)benzamide To a vial was added 1-(4-(3-chlorobenzamido)phenyl)cyclobutanecarboxylic acid (201.7 mg, 0.612 mmol), HATU (285.7 mg, 0.751 mmol), DMF (3500 µl), 2-methylcyclopropanamine (81.9 mg, 1.15 mmol) and DIEA (200 µl, 1.15 mmol). The mixture was stirred at RT for 18 h, then concentrated under reduced pressure. The residue was purified by silica gel chromatography (25 g flash column, EtOAc in hexane, 0-50%, 6 CV; 50%-50%, 6 CV) to afford 3-chloro-N-(4-(1-((2-methylcyclopropyl)carbamoyl)cyclobutyl)phenyl)benzamide. MS (ESI) Calc'd [M+H]$^+$, 383 found, 383.

Step 3: Chiral Resolution of 3-chloro-N-(4-(1-((2-methylcyclopropyl)carbamoyl)cyclobutyl)phenyl)benzamide (Examples 21, 22 and 23)

Preparative resolution of 3-chloro-N-(4-(1-((2-methylcyclopropyl)carbamoyl)cyclobutyl)phenyl)benzamide was performed using supercritical fluid chromatography on a Sepiatec Prep SFC 100. A Chiralpak IC column (5 m, 21 mm×250 mm, Chiral Technologies Inc., West Chester, Pa.) was used as the chiral stationary phase. The compound mixture was dissolved in methanol. Injection and collection were carried out using the following isocratic SFC conditions: 80% carbon dioxide and 20% methanol with 0.25% dimethylethyl amine as the mobile phase, 220 nm UV wavelength, 100 bar outlet pressure, 40° C. column compartment temperature, 70 mL/min total flow rate. Retention times for peak collection were as follows: Example 21 (isomer 1), 6.0 min; Example 22 (isomer 2), 7.2 min; and Example 23 (isomer 3), 8.9 min.

Peak 3 (Ex. 23): MS (ESI) Calc'd [M+H]$^+$, 383; found, 383. $^1$H NMR (600 MHz, DMSO-d$_6$) δ 10.35 (s, 1H), 8.04 (s, 1H), 7.95 (d, J=7.7 Hz, 1H), 7.75-7.78 (m, 3H), 7.61 (t, J=7.8 Hz, 1H), 7.41 (d, J=3.2 Hz, 1H), 7.36 (d, J=8.4 Hz, 2H), 2.78-2.65 (m, 2H), 2.42-2.32 (m, 2H), 1.87-1.73 (m, 2H), 0.78-0.69 (m, 4H), 0.28-0.21 (m, 1H).

Examples 24-44 in Table 2 were prepared in an analogous way to Examples 21, 22 and 23 using the corresponding amines in Step 2.

TABLE 2

| Ex. # | Structure | Chemical Name | Mass [M + H]+ |
|---|---|---|---|
| 24 | 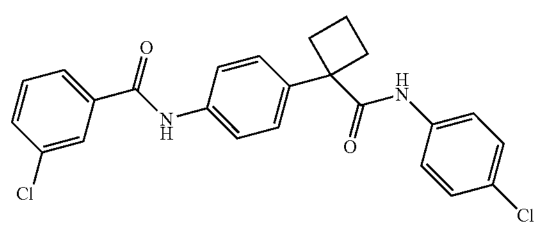 [SMILES: O=C(Nc1ccc(C2(C(=O)Nc3ccc(Cl)cc3)CCC2)cc1)c1cccc(Cl)c1] | 3-chloro-N-(4-{1-[(4-chlorophenyl)carbamoyl]cyclobutyl}phenyl)benzamide | 439 |
| 25 | 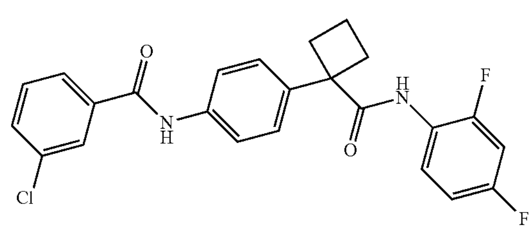 [SMILES: O=C(Nc1ccc(C2(C(=O)Nc3ccc(F)cc3F)CCC2)cc1)c1cccc(Cl)c1] | 3-chloro-N-(4-{1-[(2,4-difluorophenyl)carbamoyl]cyclobutyl}phenyl)benzamide | 441 |
| 26 | 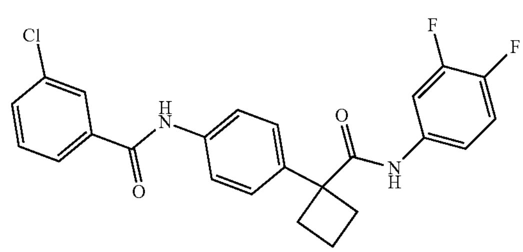 [SMILES: O=C(Nc1ccc(C2(C(=O)Nc3ccc(F)c(F)c3)CCC2)cc1)c1cccc(Cl)c1] | 3-chloro-N-(4-{1-[(3,4-difluorophenyl)carbamoyl]cyclobutyl}phenyl)benzamide | 441 |

TABLE 2-continued

| Ex. # | Structure | Chemical Name | Mass [M + H]+ |
|---|---|---|---|
| 27 | 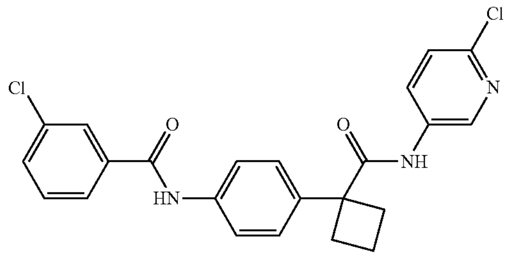 [SMILES: O=C(Nc1ccc(C2(C(=O)Nc3ccc(Cl)nc3)CCC2)cc1)c1cccc(Cl)c1] | 3-chloro-N-(4-{1-[(6-chloropyridin-3-yl)carbamoyl]cyclobutyl}phenyl)benzamide | 440 |
| 28 | 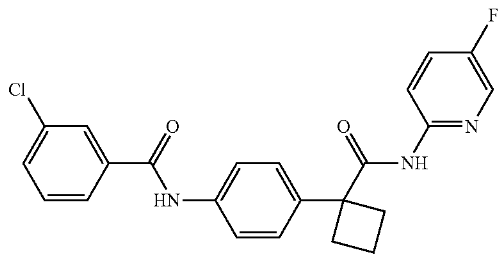 [SMILES: O=C(Nc1ccc(C2(C(=O)Nc3ccc(F)cn3)CCC2)cc1)c1cccc(Cl)c1] | 3-chloro-N-(4-{1-[(5-fluoropyridin-2-yl)carbamoyl]cyclobutyl}phenyl)benzamide | 424 |
| 29 | 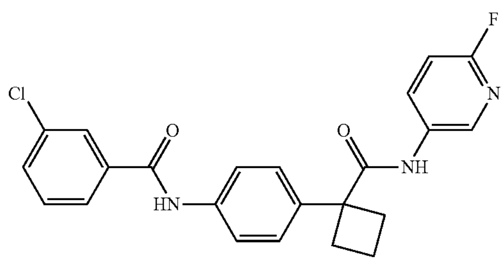 [SMILES: O=C(Nc1ccc(C2(C(=O)Nc3ccc(F)nc3)CCC2)cc1)c1cccc(Cl)c1] | 3-chloro-N-(4-{1-[(6-fluoropyridin-3-yl)carbamoyl]cyclobutyl}phenyl)benzamide | 424 |
| 30 | 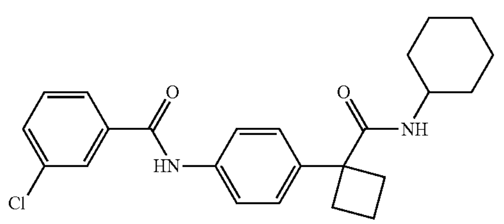 [SMILES: O=C(Nc1ccc(C2(C(=O)NC3CCCCC3)CCC2)cc1)c1cccc(Cl)c1] | 3-chloro-N-{4-[1-(cyclohexylcarbamoyl)cyclobutyl]phenyl}benzamide | 411 |
| 31 | 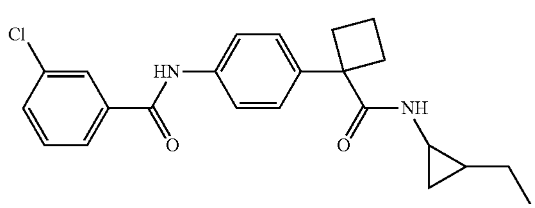 [SMILES: CCC1CC1NC(=O)C1(c2ccc(NC(=O)c3cccc(Cl)c3)cc2)CCC1] | 3-chloro-N-(4-{1-[(2-ethylcyclopropyl)carbamoyl]cyclobutyl}phenyl)benzamide | 397 |
| 32 | 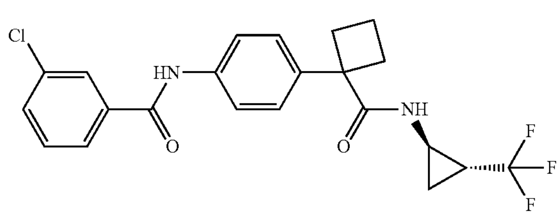 [SMILES: O=C(Nc1ccc(C2(C(=O)N[C@@H]3C[C@H]3C(F)(F)F)CCC2)cc1)c1cccc(Cl)c1] | 3-chloro-N-[4-(1-{[(1R;2R)-2-(trifluoromethyl)cyclopropyl]carbamoyl}cyclobutyl)phenyl]benzamide | 437 |

TABLE 2-continued

| Ex. # | Structure | Chemical Name | Mass [M + H]+ |
|---|---|---|---|
| 33 | 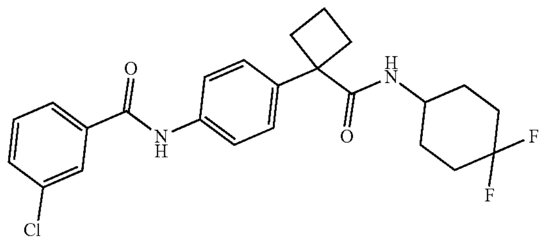 [SMILES: O=C(Nc1ccc(C2(C(=O)NC3CCC(F)(F)CC3)CCC2)cc1)c1cccc(Cl)c1] | 3-chloro-N-(4-{1-[(4,4-difluorocyclohexyl)carbamoyl]cyclobutyl}phenyl)benzamide | 447 |
| 34 | 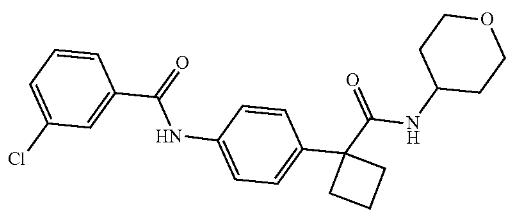 [SMILES: O=C(Nc1ccc(C2(C(=O)NC3CCOCC3)CCC2)cc1)c1cccc(Cl)c1] | 3-chloro-N-(4-{1-[(oxan-4-yl)carbamoyl]cyclobutyl}phenyl)benzamide | 413 |
| 35 | 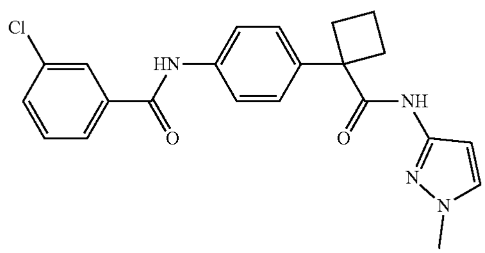 [SMILES: Cn1ccc(NC(=O)C2(c3ccc(NC(=O)c4cccc(Cl)c4)cc3)CCC2)n1] | 3-chloro-N-(4-{1-[(1-methyl-1H-pyrazol-3-yl)carbamoyl]cyclobutyl}phenyl)benzamide | 409 |
| 36 | 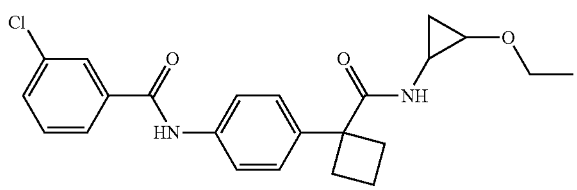 [SMILES: CCOC1CC1NC(=O)C1(c2ccc(NC(=O)c3cccc(Cl)c3)cc2)CCC1] | 3-chloro-N-(4-{1-[(2-ethoxycyclopropyl)carbamoyl]cyclobutyl}phenyl)benzamide | 413 |
| 37 | 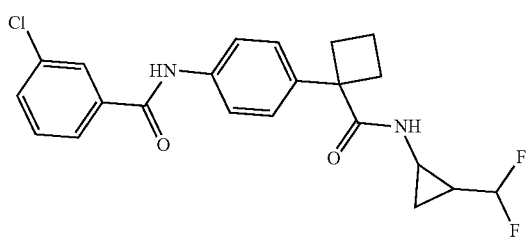 [SMILES: O=C(Nc1ccc(C2(C(=O)NC3CC3C(F)F)CCC2)cc1)c1cccc(Cl)c1] | 3-chloro-N-[4-(1-{[2-(difluoromethyl)cyclopropyl]carbamoyl}cyclobutyl)phenyl]benzamide | 419 |
| 38 | 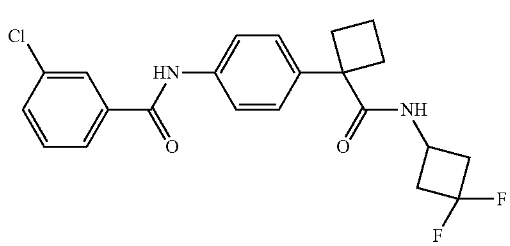 [SMILES: O=C(Nc1ccc(C2(C(=O)NC3CC(F)(F)C3)CCC2)cc1)c1cccc(Cl)c1] | 3-chloro-N-(4-{1-[(3,3-difluorocyclobutyl)carbamoyl]cyclobutyl}phenyl)benzamide | 419 |

TABLE 2-continued

| Ex. # | Structure | Chemical Name | Mass [M + H]+ |
|---|---|---|---|
| 39 | 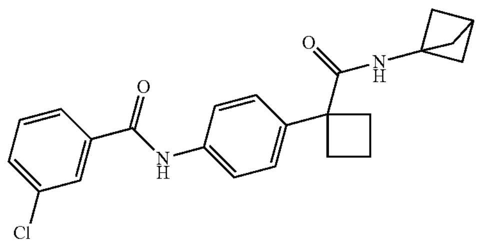 [SMILES: O=C(Nc1ccc(C2(C(=O)NC34CC(C3)C4)CCC2)cc1)c1cccc(Cl)c1] | N-(4-{1-[(bicyclo[1.1.1]pentan-1-yl)carbamoyl]cyclobutyl}phenyl)-3-chlorobenzamide | 395 |
| 40 | 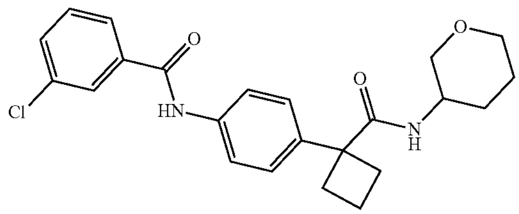 [SMILES: O=C(Nc1ccc(C2(C(=O)NC3CCCOC3)CCC2)cc1)c1cccc(Cl)c1] | 3-chloro-N-(4-{1-[(oxan-3-yl)carbamoyl]cyclobutyl}phenyl)benzamide | 413 |
| 41 | 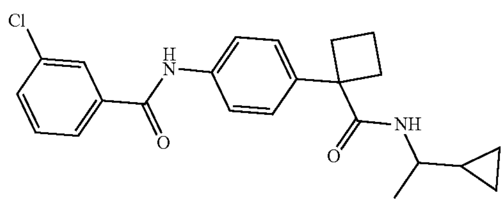 [SMILES: CC(NC(=O)C1(c2ccc(NC(=O)c3cccc(Cl)c3)cc2)CCC1)C1CC1] | 3-chloro-N-(4-{1-[(1-cyclopropylethyl)carbamoyl]cyclobutyl}phenyl)benzamide | 397 |
| 42 | 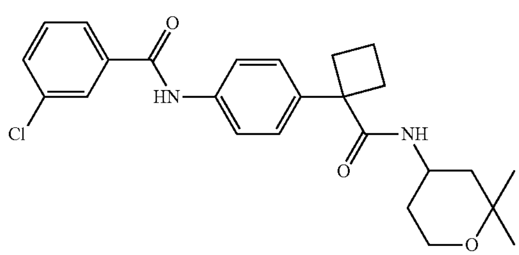 [SMILES: CC1(C)CC(NC(=O)C2(c3ccc(NC(=O)c4cccc(Cl)c4)cc3)CCC2)CCO1] | 3-chloro-N-(4-{1-[(2,2-dimethyloxan-4-yl)carbamoyl]cyclobutyl}phenyl)benzamide | 441 |
| 43 | 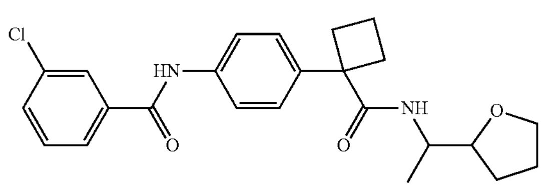 [SMILES: CC(NC(=O)C1(c2ccc(NC(=O)c3cccc(Cl)c3)cc2)CCC1)C1CCCO1] | 3-chloro-N-[4-(1-{[1-(oxolan-2-yl)ethyl]carbamoyl}cyclobutyl)phenyl]benzamide | 427 |
| 44 | 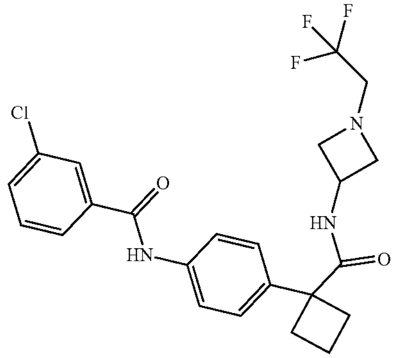 [SMILES: O=C(Nc1ccc(C2(C(=O)NC3CN(CC(F)(F)F)C3)CCC2)cc1)c1cccc(Cl)c1] | 3-chloro-N-[4-(1-{[1-(2,2,2-trifluoroethyl)azetidin-3-yl]carbamoyl}cyclobutyl)phenyl]benzamide | 466 |

Example 45: 3-Chloro-N-(4-(1-((2-ethoxypropyl) carbamoyl)cyclobutyl)phenyl)benzamide

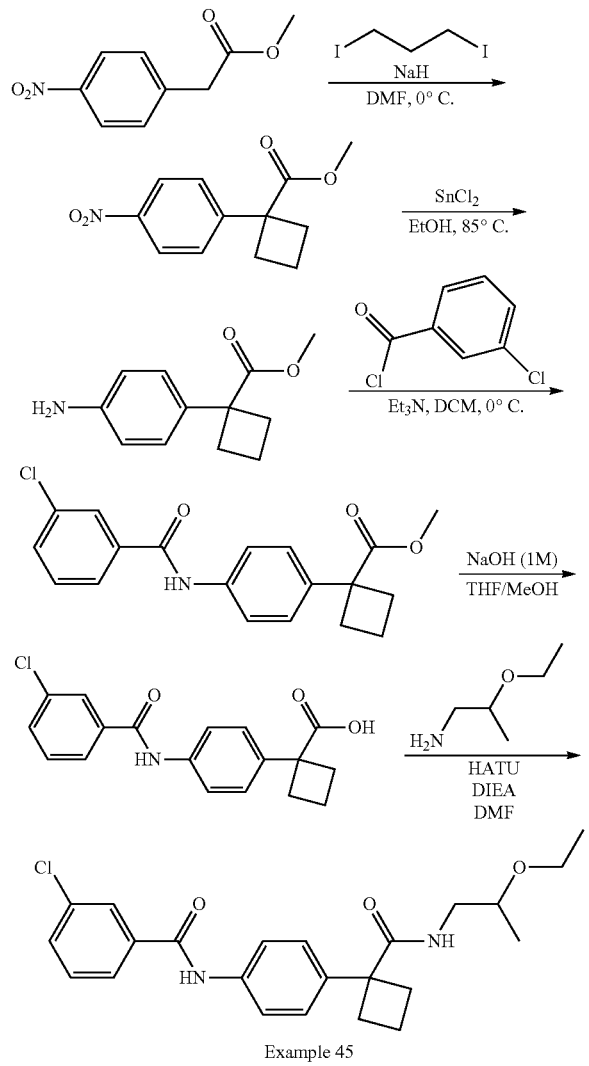

Example 45

Step 1: Preparation of methyl 1-(4-nitrophenyl)cyclobutane-1-carboxylate

A solution of methyl 2-(4-nitrophenyl)acetate (6 g, 31 mmol) in DMF (100 ml) was cooled to 0° C. with an ice bath. NaH (60% in oil) (2.5 g, 63 mmol) was added portion wise. The resulting mixture was allowed to warm to RT and was stirred for 15 min at RT. After 15 min the mixture was cooled again to 0° C. and 1,3-diiodopropane (6 ml, 52 mmol) was added drop wise. The resulting mixture was allowed to stir at 0° C. for 30 min, and from 0° C. to 10° C. for 1.5 h. After 1.5 h the solution was cooled to 0° C. and water was added. The reaction mixture was extracted 3 times with DCM. The combined organics were concentrated under reduced pressure and the residue was purified by flash chromatography on silica (120 g flash column, 0-20% EtOAc in hexane, 10 CV) to afford methyl 1-(4-nitrophenyl) cyclobutanecarboxylate.

Step 2: Preparation of methyl 1-(4-aminophenyl)cyclobutane-1-carboxylate

To a flask was added methyl 1-(4-nitrophenyl)cyclobutanecarboxylate (970 mg, 4.1 mmol), Ethanol (10 ml) and tin(II)chloride (3100 mg, 16 mmol). The reaction mixture was heated to 85° C. and was stirred for 4 h. After 4 h the reaction mixture was cooled to RT, and the pH was adjusted to ~10 by adding concentrated aq. NaOH dropwise. The mixture was extracted with EtOAc (4 times). The combined organic layers were washed with water, brine, dried over anhydrous $Na_2SO_4$, filtered and concentrated under reduced pressure to afford methyl 1-(4-aminophenyl)cyclobutanecarboxylate. MS (ESI) Calc'd [M+H]$^+$, 206; found, 206.

Step 3: Preparation of methyl 1-(4-(3-chlorobenzamido)phenyl)cyclobutane-1-carboxylate Methyl 1-(4-aminophenyl)cyclobutanecarboxylate (850 mg, 4.1 mmol) was dissolved in DCM (10 ml) and cooled to 0° C. using an ice bath. Et$_3$N (700 µl, 5.0 mmol) was added, then 3-chlorobenzoyl chloride (600 µl, 4.7 mmol) was added to the solution drop wise at 0° C. The mixture was stirred while warming to RT over 18 h. After 18 h the reaction mixture was concentrated under reduced pressure and purified by flash chromatography on silica (Silicycle, 40 g, EtOAc in hexane, 0-20%, 5 CV; 20-20%, 10 CV) to afford methyl 1-(4-(3-chlorobenzamido)phenyl)cyclobutanecarboxylate. MS (ESI) Calc'd [M+H]+, 344; found, 344.

Step 4: Preparation of 1-(4-(3-chlorobenzamido) phenyl)cyclobutane-1-carboxylic Acid To the solution of methyl 1-(4-(3-chlorobenzamido)phenyl)cyclobutanecarboxylate (1.0 g, 3.0 mmol) in THF (12 ml) was added NaOH (10 ml, 10 mmol, 1M). MeOH (5 ml) was added and the mixture was stirred at RT for 18 h. After 18 h the reaction mixture was concentrated under reduced pressure. To the resulting aqueous solution was added HCl (1 M) to adjust the pH to ~3. The solution was washed with EtOAc 3 times. The combined organics were washed with brine, dried over anhydrous $Na_2SO_4$, filtered, and concentrated under reduced pressure to afford 1-(4-(3-chlorobenzamido)phenyl)cyclobutanecarboxylic acid. MS (ESI) Calc'd [M+H]$^+$, 330; found, 330.

Step 5: Preparation of 3-chloro-N-(4-(1-((2-ethoxypropyl)carbamoyl)cyclobutyl)phenyl)benzamide (Compound 45)

To a vial was added 1-(4-(3-chlorobenzamido)phenyl) cyclobutanecarboxylic acid (15 mg, 0.045 mmol), HATU (30 mg, 0.079 mmol), 2-ethoxypropan-1-amine (15 mg, 0.145 mmol), DMF (300 µl) and DIEA (30 µl, 0.172 mmol). The mixture was stirred at RT for 4 h. After 4 h the mixture was filtered and purified under Purification A conditions to afford the title compound. MS (ESI) Calc'd [M+H]$^+$, 415; found, 415. $^1$H NMR (600 MHz, DMSO-d$_6$) δ 10.27 (s, 1H), 7.96 (s, 1H), 7.87 (d, J=7.7 Hz, 1H), 7.66 (d, J=8.1 Hz, 2H), 7.64-7.60 (m, 1H), 7.53 (t, J=7.8 Hz, 1H), 7.38 (t, J=5.6 Hz, 1H), 7.27 (d, J=8.3 Hz, 2H), 3.37-3.25 (m, 2H), 3.21 (p, J=7.0 Hz, 1H), 3.01-2.90 (m, 2H), 2.85-2.48 (m, 2H), 2.37-2.23 (m, 2H), 1.83-1.64 (m, 2H), 0.95 (t, J=6.9 Hz, 3H), 0.86 (d, J=6.1 Hz, 3H).

Examples 46-53 and 88 in Table 3 were prepared using an analogous way to Example 45, using the corresponding amines in Step 5.

TABLE 3

| Ex. # | Structure | Chemical Name | Mass [M + H]+ |
| --- | --- | --- | --- |
| 46 | 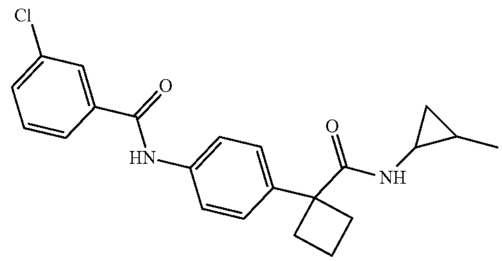 [SMILES: CC1CC1NC(=O)C1(c2ccc(NC(=O)c3cccc(Cl)c3)cc2)CCC1] | 3-chloro-N-(4-{1-[(2-methylcyclopropyl)carbamoyl]cyclobutyl}phenyl)benzamide | 383 |
| 47 | 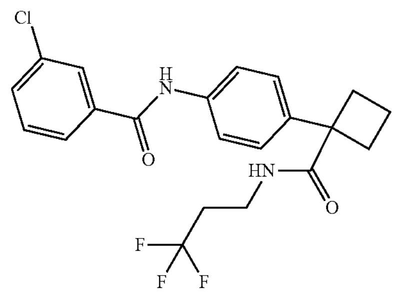 [SMILES: O=C(Nc1ccc(C2(C(=O)NCCC(F)(F)F)CCC2)cc1)c1cccc(Cl)c1] | 3-chloro-N-(4-{1-[(3,3,3-trifluoropropyl)carbamoyl]cyclobutyl}phenyl)benzamide | 425 |
| 48 | 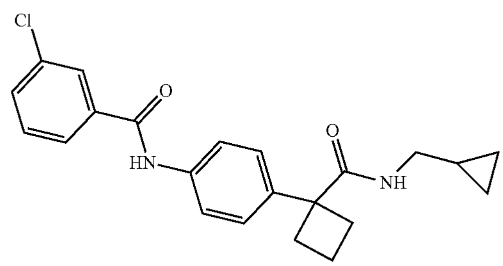 [SMILES: O=C(Nc1ccc(C2(C(=O)NCC3CC3)CCC2)cc1)c1cccc(Cl)c1] | 3-chloro-N-(4-{1-[(cyclopropylmethyl)carbamoyl]cyclobutyl}phenyl)benzamide | 383 |
| 49 | 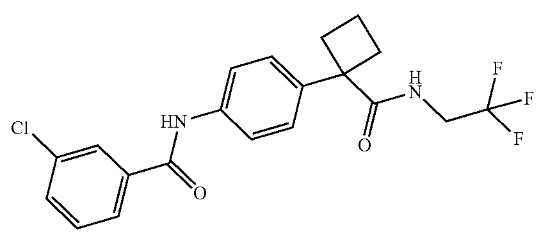 [SMILES: O=C(Nc1ccc(C2(C(=O)NCC(F)(F)F)CCC2)cc1)c1cccc(Cl)c1] | 3-chloro-N-(4-{1-[(2,2,2-trifluoroethyl)carbamoyl]cyclobutyl}phenyl)benzamide | 411 |
| 50 | 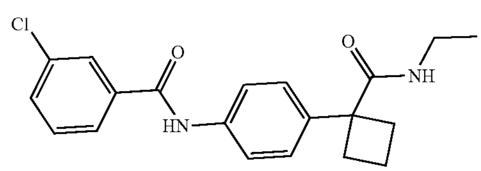 [SMILES: CCNC(=O)C1(c2ccc(NC(=O)c3cccc(Cl)c3)cc2)CCC1] | 3-chloro-N-{4-[1-(ethylcarbamoyl)cyclobutyl]phenyl}benzamide | 357 |
| 51 | 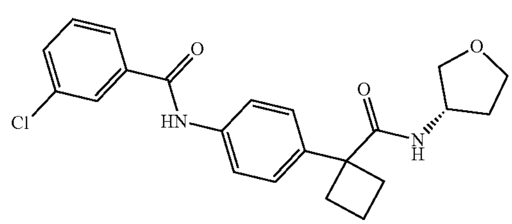 [SMILES: O=C(Nc1ccc(C2(C(=O)N[C@H]3CCOC3)CCC2)cc1)c1cccc(Cl)c1] | 3-chloro-N-[4-(1-{[(3S)-oxolan-3-yl]carbamoyl}cyclobutyl)phenyl]benzamide | 399 |

TABLE 3-continued

| Ex. # | Structure | Chemical Name | Mass [M + H]+ |
|---|---|---|---|
| 52 | 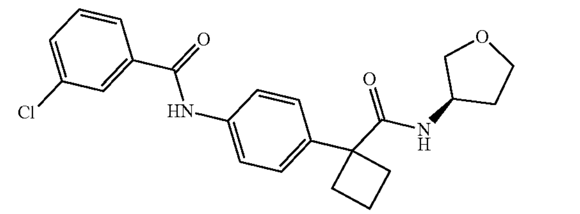 [SMILES: O=C(Nc1ccc(C2(C(=O)N[C@@H]3CCOC3)CCC2)cc1)c1cccc(Cl)c1] | 3-chloro-N-[4-(1-{[(3R)-oxolan-3-yl]carbamoyl}cyclobutyl)phenyl]benzamide | 399 |
| 53 | 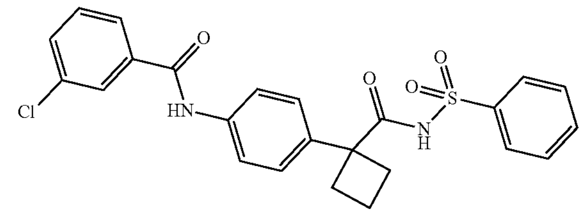 [SMILES: O=C(Nc1ccc(C2(C(=O)NS(=O)(=O)c3ccccc3)CCC2)cc1)c1cccc(Cl)c1] | 3-chloro-N-(4-{1-[(phenylsulfonyl)carbamoyl]cyclobutyl}phenyl)benzamide | 469 |
| 88 | 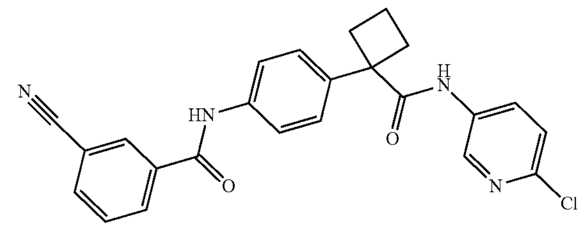 [SMILES: N#Cc1cccc(C(=O)Nc2ccc(C3(C(=O)Nc4ccc(Cl)nc4)CCC3)cc2)c1] | N-(4-{1-[(6-chloropyridin-3-yl)carbamoyl]cyclobutyl}phenyl)-3-cyanobenzamide | 431 |

Example 54: 5-Methyl-N-(4-(1-(propylcarbamoyl)cyclobutyl)phenyl)-1,2,3-thiadiazole-4-carboxamide

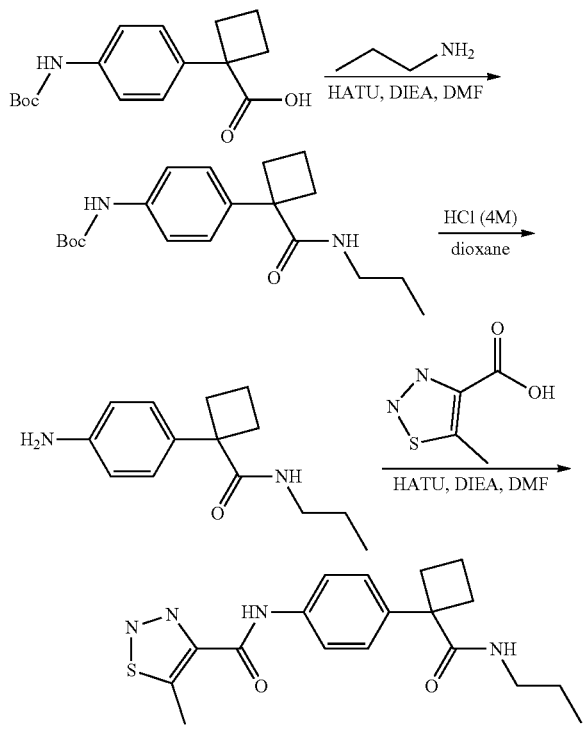

Example 54

Step 1: Preparation of tert-butyl (4-(1-(propylcarbamoyl)cyclobutyl)phenyl)carbamate To a flask was added 1-(4-((tert-butoxycarbonyl)amino)phenyl)cyclobutanecarboxylic acid (1 g, 3.4 mmol), HATU (1600 mg, 4.1 mmol), DCM (25 ml), DIEA (2.0 ml, 11 mmol) and propan-1-amine (380 mg, 6.4 mmol). The mixture was stirred at RT for 18 h. After 18 h the mixture was washed with water, followed by brine. The combined organics were dried over anhydrous Na$_2$SO$_4$, filtered, and concentrated under reduced pressure. The residue was purified on silica gel (40 g flash column, EtOAc in hexane, 0-40%, 15 CV) to afford tert-butyl (4-(1-(propylcarbamoyl)cyclobutyl)phenyl)carbamate. MS (ESI) Calc'd [M+H]$^+$, 333; found, 333.

Step 2: Preparation of 1-(4-aminophenyl)-N-propyl-cyclobutane-1-carboxamide

To the flask containing tert-butyl (4-(1-(propylcarbamoyl)cyclobutyl)phenyl)carbamate (950 mg, 2.9 mmol) was added dioxane (10 ml) and 4 M HCl in dioxane (10 ml, 40 mmol). The mixture was stirred at RT for 16 h. After 16 h the reaction mixture was concentrated under reduced pressure to afford 1-(4-aminophenyl)-N-propylcyclobutanecarboxamide, HCl. MS (ESI) Calc'd [M+H]$^+$, 233; found, 233.

Step 3: Preparation of 5-methyl-N-(4-(1-(propylcarbamoyl)cyclobutyl)phenyl)-1,2,3-thiadiazole-4-carboxamide To a vial was added 1-(4-aminophenyl)-N-propylcyclobutanecarboxamide, HCl (15 mg, 0.056 mmol), HATU (32 mg, 0.084 mmol), 5-methyl-1,2,3-thiadiazole-4-carboxylic acid (14 mg, 0.097 mmol), DMF (300 µl) and DIEA (100 µl, 0.57 mmol). The mixture was stirred at RT for 18 h. After 18 h the mixture was filtered and purified under Purification A conditions to afford the title compound. MS (ESI) Calc'd [M+H]+, 359; found, 359. $^1$H NMR (500 MHz, DMSO-$d_6$) δ 9.95 (s, 1H), 7.73 (d, J=8.6 Hz, 2H), 7.50 (t, J=5.7 Hz, 1H), 7.25 (d, J=8.6 Hz, 2H), 3.32 (s, 3H), 2.95 (q, J=6.6 Hz, 2H), 2.73-2.58 (m, 2H), 2.39-2.26 (m, 2H), 1.89-1.64 (m, 2H), 1.41-1.27 (m, 2H), 0.72 (t, J=7.4 Hz, 3H).

Examples 55-58 in Table 4 were prepared in an analogous way to Example 54, using the corresponding carboxylic acids in Step 3.

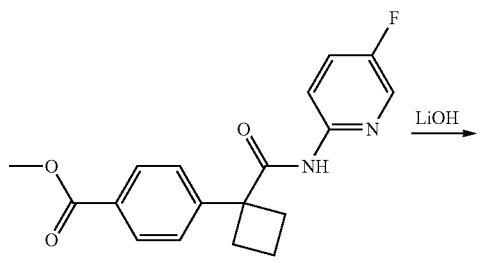

TABLE 4

| Ex. # | Structure | Chemical Name | Mass [M + H]+ |
|---|---|---|---|
| 55 | 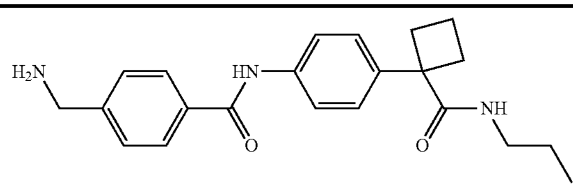 | 4-(aminomethyl)-N-{4-[1-(propylcarbamoyl)cyclobutyl]phenyl}benzamide | 366 |
| 56 | 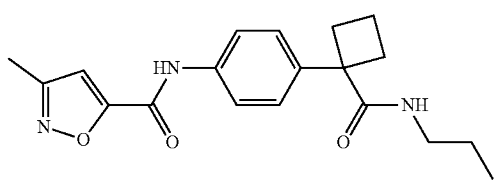 [SMILES: CCCNC(=O)C1(c2ccc(NC(=O)c3cc(C)no3)cc2)CCC1] | 3-methyl-N-{4-[1-(propylcarbamoyl)cyclobutyl]phenyl}-1,2-oxazole-5-carboxamide | 342 |
| 57 | 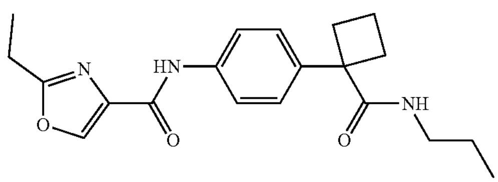 [SMILES: CCCNC(=O)C1(c2ccc(NC(=O)c3coc(CC)n3)cc2)CCC1] | 2-ethyl-N-{4-[1-(propylcarbamoyl)cyclobutyl]phenyl}-1,3-oxazole-4-carboxamide | 356 |
| 58 | 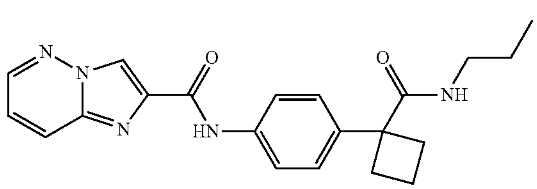 [SMILES: CCCNC(=O)C1(c2ccc(NC(=O)c3cn4ncccc4n3)cc2)CCC1] | N-{4-[1-(propylcarbamoyl)cyclobutyl]phenyl}imidazo[1,2-b]pyridazine-2-carboxamide | 378 |

Example 59: N-(3-chloro-2-fluorophenyl)-4-(1-((5-fluoropyridin-2-yl)carbamoyl)cyclobutyl)benzamide

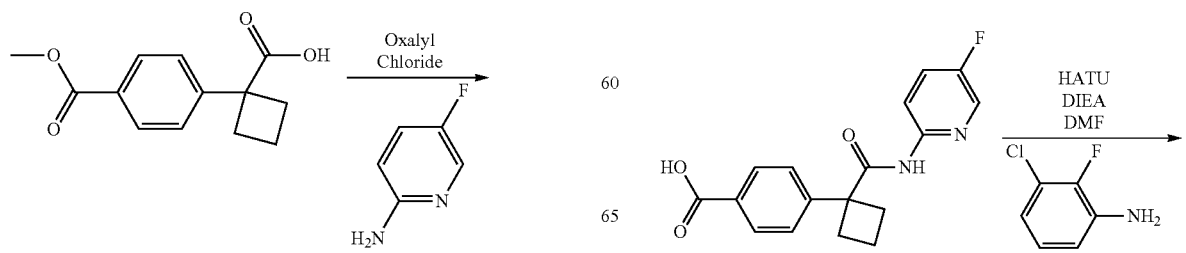

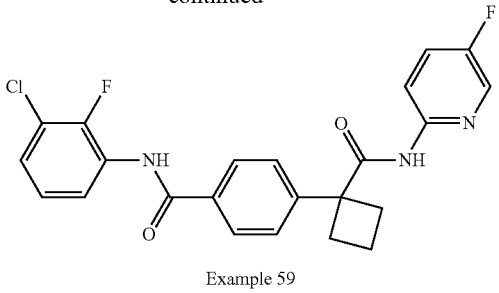

Example 59

Step 1: Preparation of methyl 4-(1-((5-fluoropyridin-2-yl)carbamoyl)cyclobutyl)benzoate 1-(4-(methoxycarbonyl)phenyl)cyclobutanecarboxylic acid (2000 mg, 8.5 mmol) and oxalyl chloride (0.75 ml, 8.5 mmol) were stirred in DCM (10.0 ml)/DMF (0.2 ml). The reaction mixture was stirred at RT for 4 h. After 4 h the reaction mixture was concentrated under reduced pressure. To the residue was added a mixture of 2-amino-5-fluoropyridine (960 mg, 8.5 mmol) in pyridine (10 ml), and the mixture was cooled to 0° C. The mixture was slowly warmed to RT and stirred for 15 h. After 15 h the reaction mixture was concentrated under reduced pressure and purified by column chromatography on silica gel (DCM/MeOH; 0-10%) to afford methyl 4-(1-((5-fluoropyridin-2-yl)carbamoyl)cyclobutyl)benzoate. MS (ESI) Calc'd [M+H]+, 329; found, 329.

Step 2: Preparation of 4-(1-((5-fluoropyridin-2-yl)carbamoyl)cyclobutyl)benzoic Acid To a vial containing methyl 4-(1-((5-fluoropyridin-2-yl)carbamoyl)cyclobutyl)benzoate (1000 mg, 3.1 mmol) in THF (4.0 ml) and MeOH (1.33 ml) was added LiOH in water (6.1 ml, 12 mmol). The mixture was stirred at RT for 24 h. After 24 h the crude reaction mixture was concentrated under reduced pressure. The resulting aqueous solution was acidified to pH ~3 by adding HCl (1M) drop wise. The residue was washed with DCM (3 times). The combined organic phase was washed with brine, dried over anhydrous magnesium sulfate, filtered, and concentrated under reduced pressure to afford 4-(1-((5-fluoropyridin-2-yl)carbamoyl)cyclobutyl)benzoic acid. MS (ESI) Calc'd [M+H]+, 315; found, 315.

Step 3: Preparation N-(3-chloro-2-fluorophenyl)-4-(1-((5-fluoropyridin-2-yl)carbamoyl)cyclobutyl)benzamide A 20 mL vial was charged with 4-(1-((5-fluoropyridin-2-yl)carbamoyl)cyclobutyl)benzoic acid (30 mg, 0.095 mmol) and DMF (2.0 ml). HATU (44 mg, 0.12 mmol) was added to the reaction mixture, and the reaction mixture was allowed for stir for 5 min. After 5 min 3-chloro-2-fluoroaniline (14 mg, 0.095 mmol) was added, followed by DIEA (0.10 ml, 0.57 mmol). The reaction was stirred for 24 h at 50° C. After 24 h EtOAc was added, and the reaction mixture was washed with 3 portions of 1 N aqueous HCl, 2 portions of water, 1 portion of brine, and 1 portion of saturated aqueous NaHCO$_3$. The combined organics were dried over anhydrous Na$_2$SO$_4$, filtered, and concentrated under reduced pressure. The residue was purified under Purification A conditions to afford the title compound. MS (ESI) Calc'd [M+H]+, 442; found, 442. $^1$H NMR (400 MHz, DMSO-d$_6$) δ 10.25 (s, 1H), 10.22 (s, 1H), 8.29 (s, 1H), 8.07 (s, 1H), 7.95 (s, 2H), 7.72 (s, 1H), 7.64 (s, 2H), 7.56 (s, 1H), 7.45 (s, 1H), 7.25 (s, 1H), 2.91 (s, 3H), 1.82 (s, 3H).

Examples 60-61 in Table 5 were prepared in an analogous manner to Example 59, using the corresponding amines in Step 3.

TABLE 5

| Ex. # | Structure | Chemical Name | Mass [M + H]+ |
| --- | --- | --- | --- |
| 60 | 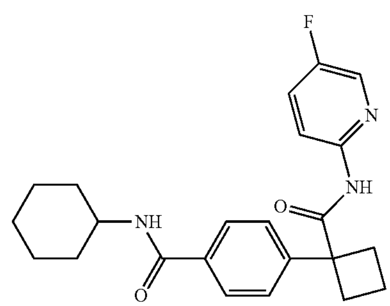 [SMILES: O=C(NC1CCCCC1)c1ccc(C2(C(=O)Nc3ccc(F)cn3)CCC2)cc1] | N-cyclohexyl-4-{1-[(5-fluoropyridin-2-yl)carbamoyl]cyclobutyl}benzamide | 396 |
| 61 | 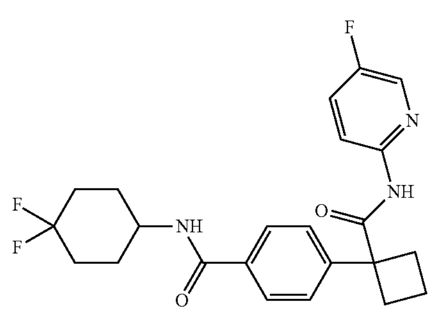 [SMILES: O=C(NC1CCC(F)(F)CC1)c1ccc(C2(C(=O)Nc3ccc(F)cn3)CCC2)cc1] | N-(4,4-difluorocyclohexyl)-4-{1-[(5-fluoropyridin-2-yl)carbamoyl]cyclobutyl}benzamide | 432 |

Example 62: 3-Chloro-N-(4-(3-fluoro-1-((4-fluorophenyl)carbamoyl)cyclobutyl)phenyl)benzamide

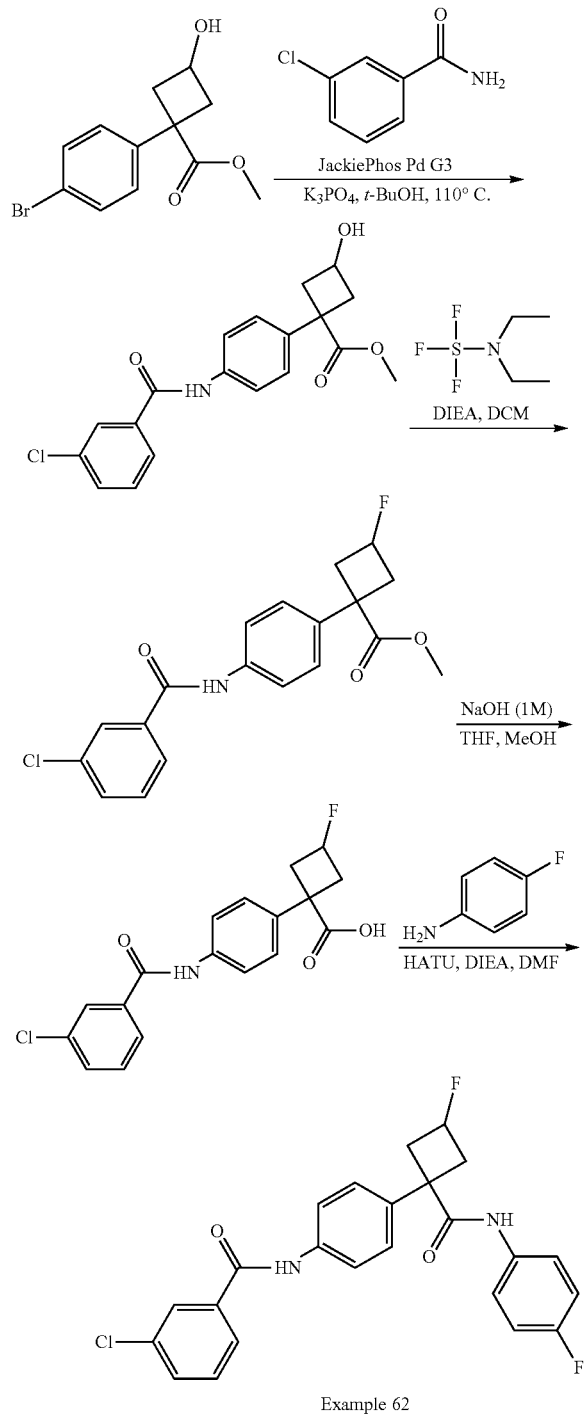

Example 62

Step 1: Preparation of methyl 1-(4-(3-chlorobenzamido)phenyl)-3-hydroxycyclobutane-1-carboxylate To a vial was added methyl 1-(4-bromophenyl)-3-hydroxycyclobutanecarboxylate (250 mg, 0.89 mmol), 3-chlorobenzamide (210 mg, 1.3 mmol), $K_3PO_4$ (570 mg, 2.7 mmol), JackiePhos Pd G3 (120 mg, 0.100 mmol) and t-BuOH (4 ml). The mixture was evacuated and backfilled with $N_2$ (4 times), then heated to 110° C. for 2.5 h. After 2.5 h the reaction mixture was filtered and purified under Purification A conditions to afford methyl 1-(4-(3-chlorobenzamido)phenyl)-3-hydroxycyclobutanecarboxylate. MS (ESI) Calc'd [M+H]$^+$, 360; found, 360.

Step 2: Preparation of methyl 1-(4-(3-chlorobenzamido)phenyl)-3-fluorocyclobutane-1-carboxylate To a solution of methyl 1-(4-(3-chlorobenzamido)phenyl)-3-hydroxycyclobutanecarboxylate (40 mg, 0.11 mmol) in DCM (800 µl) and DIEA (50 µl, 0.29 mmol), was added a solution of diethylaminosulfur trifluoride (27 mg, 0.17 mmol) in DCM (200 µl) at 0° C. The mixture was warmed to RT and stirred at RT for 24 h. After 24 h the mixture was cooled to 0° C. and DAST (16 µl, 0.12 mmol) in DCM (200 ul) was added. After stirring at RT for 20 h, saturated $NaHCO_3$ was added and the mixture was washed with DCM. The organic layers were washed with brine, dried over anhydrous $Na_2SO_4$, filtered, and concentrated under reduced pressure. The residue was purified on silica gel (25 g flash column, EtOAc in hexane, 0-50%, 15 CV) to afford methyl 1-(4-(3-chlorobenzamido)phenyl)-3-fluorocyclobutanecarboxylate. MS (ESI) Calc'd [M+H]$^+$, 362; found, 362.

Step 3: Preparation of 1-(4-(3-chlorobenzamido)phenyl)-3-fluorocyclobutane-1-carboxylic Acid To a vial containing methyl 1-(4-(3-chlorobenzamido)phenyl)-3-fluorocyclobutanecarboxylate (14 mg, 0.039 mmol) was added THF (300 µl), MeOH (100 µl) and NaOH (100 µl, 0.100 mmol, 1M). The mixture was stirred at RT for 18 h. After 18 h the reaction mixture was concentrated under reduced pressure. To the resulting aqueous solution, was added HCl (1M) to adjust the pH to ~3. The reaction mixture was concentrated under reduced pressure to afford 1-(4-(3-chlorobenzamido)phenyl)-3-fluorocyclobutane-1-carboxylic acid. MS (ESI) Calc'd [M+H]$^+$, 348; found, 348.

Step 4: Preparation of 3-chloro-N-(4-(3-fluoro-1-((4-fluorophenyl)carbamoyl)cyclobutyl)phenyl)benzamide (Compound 62)

To a vial was added 1-(4-(3-chlorobenzamido)phenyl)-3-fluorocyclobutanecarboxylic acid (13 mg, 0.037 mmol), HATU (21 mg, 0.056 mmol), DMF (400 µl), 4-fluoroaniline (21 mg, 0.19 mmol) and DIEA (50 µl, 0.29 mmol). The mixture was stirred at RT for 2 h. After 2 h the mixture was filtered and purified under Purification A conditions to afford the title compound. MS (ESI) Calc'd [M+H]$^+$, 441; found, 441. $^1$H NMR (600 MHz, DMSO-$d_6$) δ 10.32 (s, 1H), 9.52 (s, 1H), 7.95 (s, 1H), 7.86 (d, J=7.7 Hz, 1H), 7.71 (d, J=8.4 Hz, 2H), 7.62 (d, J=7.8 Hz, 1H), 7.57-7.41 (m, 3H), 7.35 (d, J=8.4 Hz, 2H), 7.07 (t, J=8.8 Hz, 2H), 5.07 (dq, J=56.0, 6.7 Hz, 1H), 3.39-3.17 (m, 2H), 2.64-2.45 (m, 2H).

Example 63: Preparation of 3-chloro-N-(4-(3,3-difluoro-1-((4-fluorophenyl)carbamoyl)cyclobutyl)phenyl)benzamide

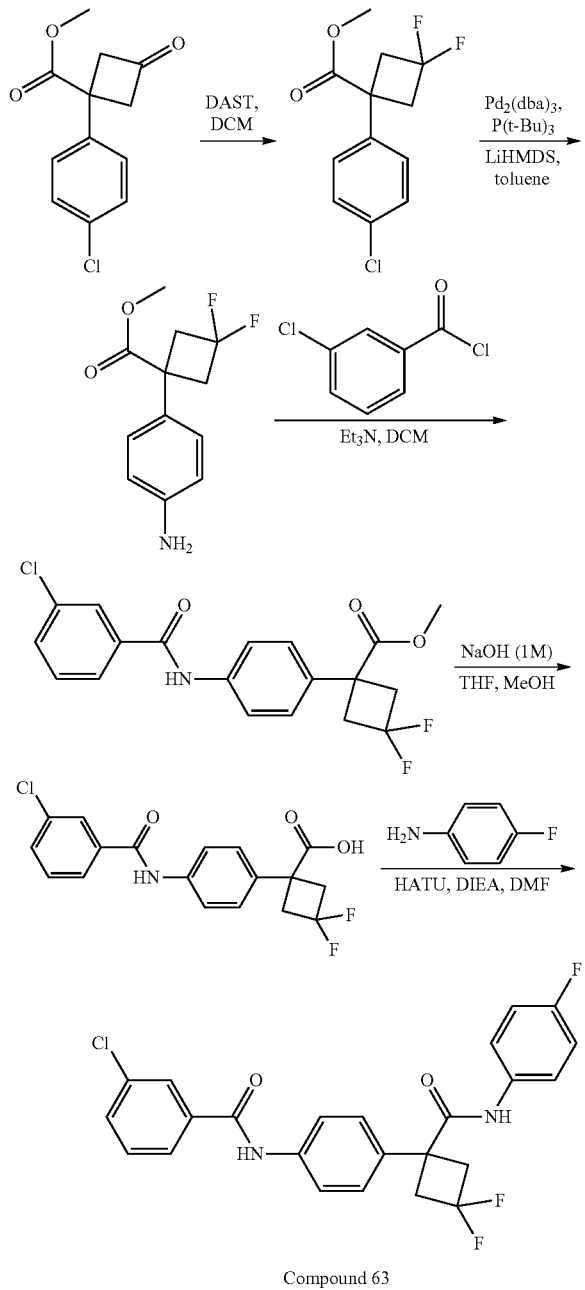

Compound 63

Step 1: Preparation of methyl 1-(4-chlorophenyl)-3,3-difluorocyclobutane-1-carboxylate To a solution of methyl 1-(4-chlorophenyl)-3-oxocyclobutanecarboxylate (0.49 g, 2.0 mmol) in DCM (10 ml), was added a solution of DAST (0.6 ml, 4.5 mmol) in DCM (2 ml) at 0° C. The mixture was warmed to RT and stirred at RT for 16 h. After 16 h saturated NaHCO$_3$ was added and the mixture was washed with DCM. The organic layers were washed with brine, dried over anhydrous Na$_2$SO$_4$, filtered, and concentrated under reduced pressure. The residue was purified on silica gel chromatography (12 g flash column, EtOAc in hexane, 0-10%, 15 CV) to afford methyl 1-(4-chlorophenyl)-3,3-difluorocyclobutanecarboxylate.

Step 2: Preparation of methyl 1-(4-aminophenyl)-3,3-difluorocyclobutane-1-carboxylate To a vial was added methyl 1-(4-chlorophenyl)-3,3-difluorocyclobutanecarboxylate (95 mg, 0.36 mmol), Pd$_2$(dba)$_3$ (42 mg, 0.046 mmol), and Toluene (1500 µl). The mixture was evacuated and back filled with N$_2$ (3 times). Tri-tert-butylphosphine 10% weight in hexane (97 mg, 0.048 mmol) and LiHMDS (500 µl, 0.500 mmol) were added to the reaction vial. The mixture was evacuated and back filled with N$_2$ (3 times). The resulting solution was stirred at RT for 17 h. After 17 h the mixture was diluted with Et$_2$O (2 ml), and the silylamide was deprotected by adding 1 drop of 1 N HCl. The mixture was washed with 1N NaOH. The organic layer was washed with brine, dried over magnesium sulfate, filtered, and concentrated under reduced pressure. The residue was purified on silica gel chromatography (12 g flash column, 0-50%, 15 C V; 50-50%, 5 CV) to afford methyl 1-(4-aminophenyl)-3,3-difluorocyclobutanecarboxylate. MS (ESI) Calc'd [M+H]$^+$, 242; found, 242.

Step 3: Preparation of methyl 1-(4-(3-chlorobenzamido)phenyl)-3,3-difluorocyclobutane-1-carboxylate Methyl 1-(4-aminophenyl)-3,3-difluorocyclobutanecarboxylate (74 mg, 0.31 mmol) was dissolved in DCM (1500 µl) and cooled to 0° C. using an ice bath. Et$_3$N (70 µl, 0.50 mmol) and 3-chlorobenzoyl chloride (50 µl, 0.39 mmol) were added to the solution drop wise at 0° C. The mixture was stirred at RT for 18 h. After 18 h the reaction mixture was concentrated under reduced pressure. The residue was purified on silica gel chromatography (12 g flash column, EtOAc in hexane, 0-20%, 5 CV; 20-20%, 10 CV) to afford methyl 1-(4-(3-chlorobenzamido)phenyl)-3,3-difluorocyclobutanecarboxylate. MS (ESI) Calc'd [M+H]$^+$, 380; found, 380.

Step 4: Preparation of 1-(4-(3-chlorobenzamido)phenyl)-3,3-difluorocyclobutane-1-carboxylic Acid To the vial containing methyl 1-(4-(3-chlorobenzamido)phenyl)-3,3-difluorocyclobutanecarboxylate (75 mg, 0.20 mmol) was added THF (1.5 ml). To this solution was added NaOH (500 µl, 0.500 mmol), followed by MeOH (0.5 ml). The mixture was stirred at RT for 3 h. After 3 h the reaction mixture was concentrated under reduced pressure. The resulting aqueous solution was acidified to pH ~2 by drop wise addition of HCl (1 M). The resulting solution was washed with EtOAc 3 times. The combined organics were dried over anhydrous Na$_2$SO$_4$, filtered, and concentrated under reduced pressure to afford 1-(4-(3-chlorobenzamido)phenyl)-3,3-difluorocyclobutane-1-carboxylic acid. MS (ESI) Calc'd [M+H]$^+$, 366; found, 366.

Step 5: Preparation of 3-chloro-N-(4-(3,3-difluoro-1-((4-fluorophenyl)carbamoyl)cyclobutyl)phenyl)benzamide (Compound 63)

To a vial was added 1-(4-(3-chlorobenzamido)phenyl)-3,3-difluorocyclobutanecarboxylic acid (36 mg, 0.098 mmol), 4-fluoroaniline (28 mg, 0.25 mmol), HATU (45 mg, 0.12 mmol), DMF (800 μl) and DIEA (60 μl, 0.34 mmol). The mixture was stirred at RT for 18 h. After 18 h the mixture was filtered and purified under Purification A conditions to afford the title compound. MS (ESI) Calc'd [M+H]+, 459; found, 459. ¹H NMR (600 MHz, DMSO-d₆) δ 10.34 (s, 1H), 9.73 (s, 1H), 7.95 (s, 1H), 7.86 (d, J=7.7 Hz, 1H), 7.73 (d, J=8.4 Hz, 2H), 7.62 (d, J=7.8 Hz, 1H), 7.58-7.49 (m, 3H), 7.44 (d, J=8.4 Hz, 2H), 7.08 (t, J=8.7 Hz, 2H), 3.63-3.29 (m, 2H), 3.08 (q, J=13.0 Hz, 2H).

Examples 65 and 69 in Table 6 were prepared in an analogous way to Example 63, using the corresponding amines in Step 5.

Examples 64 and 66-68 in Table 6 were prepared in an analogous fashion to Example 63, with the corresponding amines in step 5.

Preparative resolution of 3-chloro-N-(4-(1-((2-ethoxycyclopropyl)carbamoyl)-3,3-difluorocyclobutyl)phenyl)benzamide was performed using supercritical fluid chromatography on a Berger Multigram II preparative SFC. A Chiralcel OD-H column (5 μm, 21 mm×250 mm, Chiral Technologies Inc., West Chester, Pa.) was used as the chiral stationary phase. The compound mixture was dissolved in methanol. Injection and collection were carried out using the following isocratic SFC conditions: 80% carbon dioxide and 20% methanol with 0.25% dimethylethyl amine as the mobile phase, 220 nm UV wavelength, 100 bar outlet pressure, 35° C. column compartment temperature, 70 mL/min total flow rate. Retention times for peak collection were as follows: Compound 68, 3.6 min; Compound 67, 5.1 min, Compound 64, 6.3 min, Compound 66, 7.9 min.

TABLE 6

| Ex. # | Structure | Chemical Name | Mass [M + H]+ |
|---|---|---|---|
| 64 | 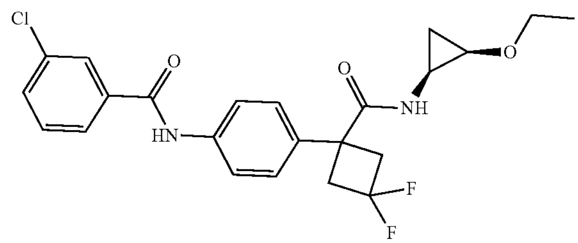 [SMILES: CCO[C@@H]1C[C@@H]1NC(=O)C1(c2ccc(NC(=O)c3cccc(Cl)c3)cc2)CC(F)(F)C1] | 3-chloro-N-[4-(1-{[(1S,2R)-2-ethoxycyclopropyl]carbamoyl}-3,3-difluorocyclobutyl)phenyl]benzamide | 449 |
| 65 | 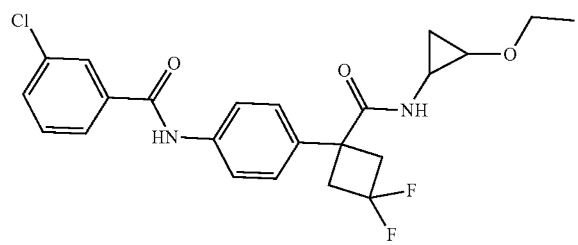 [SMILES: CCOC1CC1NC(=O)C1(c2ccc(NC(=O)c3cccc(Cl)c3)cc2)CC(F)(F)C1] | 3-chloro-N-(4-{1[a-ethoxycyclopropyl)carbamoyl]-3,3-difluorocyclobutyl}phenyl)benzamide | 449 |
| 66 | 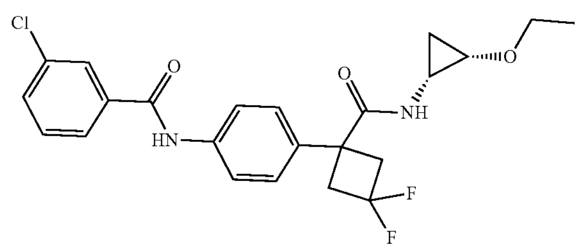 [SMILES: CCO[C@H]1C[C@H]1NC(=O)C1(c2ccc(NC(=O)c3cccc(Cl)c3)cc2)CC(F)(F)C1] | 3-chloro-N-[4-(1-{[(1R,2S)-2-ethoxycyclopropyl]carbamoyl}-3,3-difluorocyclobutyl)phenyl]benzamide | 449 |
| 67 | 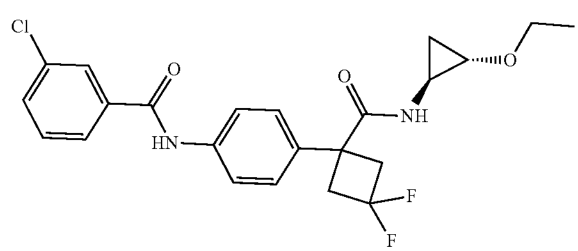 [SMILES: CCO[C@H]1C[C@@H]1NC(=O)C1(c2ccc(NC(=O)c3cccc(Cl)c3)cc2)CC(F)(F)C1] | 3-chloro-N-[4-(1-{[(1S,2S)-2-ethoxycyclopropyl]carbamoyl}-3,3-difluorocyclobutyl)phenyl]benzamide | 449 |

TABLE 6-continued

| Ex. # | Structure | Chemical Name | Mass [M + H]+ |
|---|---|---|---|
| 68 | 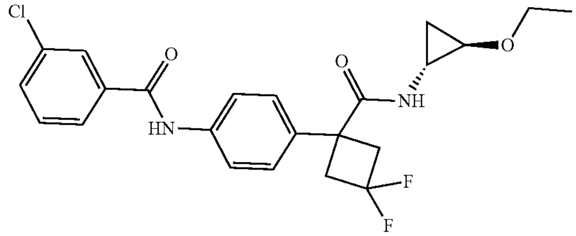 [SMILES: CCO[C@@H]1C[C@H]1NC(=O)C1(c2ccc(NC(=O)c3cccc(Cl)c3)cc2)CC(F)(F)C1] | 3-chloro-N-[4-(1-{[(1R,2R)-2-ethoxycyclopropyl]carbamoyl}-3,3-difluorocyclobutyl)phenyl]benzamide | 449 |
| 69 | 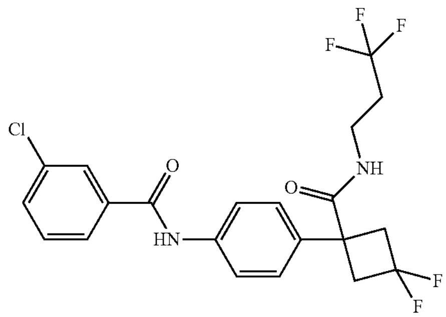 [SMILES: O=C(Nc1ccc(C2(C(=O)NCCC(F)(F)F)CC(F)(F)C2)cc1)c1cccc(Cl)c1] | 3-chloro-N-(4-{3,3-difluoro-1-[(3,3,3-trifluoropropyl)carbamoyl]cyclobutyl}phenyl)benzamide | 461 |

Example 70: 3-Chloro-N-(4-((cis)-1-((4-fluorophenyl)carbamoyl)-3-hydroxycyclobutyl)phenyl)benzamide

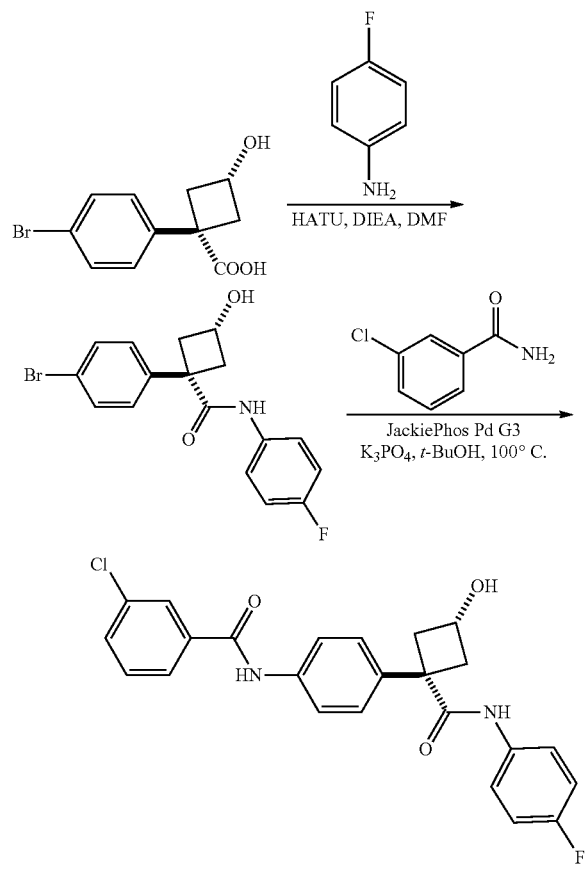

Example 70

Step 1: Preparation of (cis)-1-(4-bromophenyl)-N-(4-fluorophenol)-3-hydroxycyclobutane-1-carboxamide To a vial was added (cis)-1-(4-bromophenyl)-3-hydroxycyclobutanecarboxylic acid (100 mg, 0.37 mmol), HATU (170 mg, 0.44 mmol), DMF (2500 µl), 4-fluoroaniline (45 mg, 0.41 mmol) and DIEA (200 µl, 1.1 mmol). The mixture was stirred at RT for 18 h. After 18 h the solvent was concentrated under reduced pressure. The residue was purified by flash chromatography on silica (12 g, EtOAc in hexane, 0-80%, 10 CV) to afford (cis)-1-(4-bromophenyl)-N-(4-fluorophenyl)-3-hydroxycyclobutanecarboxamide. MS (ESI) Calc'd [M+H]+, 364; found, 364.

Step 2: Preparation of 3-chloro-N-(4-((cis)-1-((4-fluorophenyl)carbamoyl)-3-hydroxycyclobutyl)phenyl)benzamide To a vial was added (cis)-1-(4-bromophenyl)-N-(4-fluorophenyl)-3-hydroxycyclobutanecarboxamide (39 mg, 0.11 mmol), 3-chlorobenzamide (25 mg, 0.16 mmol), K$_3$PO$_4$ (70 mg, 0.33 mmol), JackiePhos Pd G3 (12 mg, 11 µmol) and t-BuOH (700 µl). The mixture was evacuated and backfilled with N$_2$ (4 times), then heated at 100° C. for 3 h. After 3 h the mixture was filtered and purified under Purification A conditions to afford the title compound. MS (ESI) Calc'd [M+H]+, 439; found, 439. $^1$H NMR (600 MHz, DMSO-d$_6$) δ 10.30 (s, 1H), 9.30 (s, 1H), 7.95 (s, 1H), 7.86 (d, J=7.7 Hz, 1H), 7.70 (d, J=8.4 Hz, 2H), 7.62 (d, J=7.8 Hz, 1H), 7.58-7.49 (m, 3H), 7.44 (d, J=8.4 Hz, 2H), 7.05 (t, J=8.8 Hz, 2H), 3.87 (p, J=7.2 Hz, 1H), 3.33 (s, 1H), 2.86-2.73 (m, 2H), 2.54-2.43 (m, 2H).

Example 71: 3-Chloro-N-(4-((1r,3r)-1-((4-fluorophenyl)carbamoyl)-3-hydroxy-3-methylcyclobutyl)phenyl)benzamide

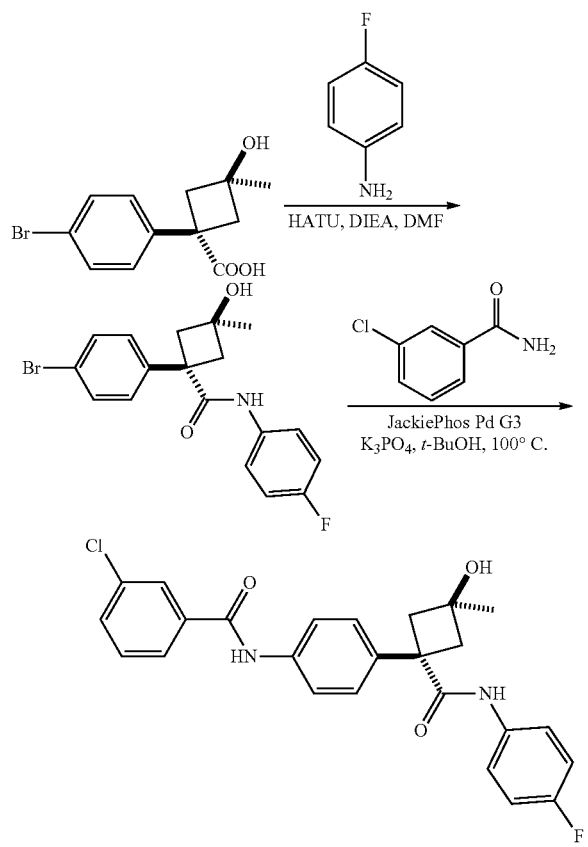

Example 71

Step 1: Preparation of (1r,3r)-1-(4-bromophenyl)-N-(4-fluorophenyl)-3-hydroxy-3-methylcyclobutane-1-carboxamide To a vial was added (1R,3R)-1-(4-bromophenyl)-3-hydroxy-3-methylcyclobutanecarboxylic acid (120 mg, 0.41 mmol), HATU (200 mg, 0.52 mmol), DMF (2.5 ml), 4-fluoroaniline (50 mg, 0.45 mmol) and DIEA (250 µl, 1.4 mmol). The mixture was stirred at RT for 18 h. After 18 h the reaction mixture was concentrated under reduced pressure. The residue was purified by flash chromatography on silica (12 g, EtOAc in hexane, 0-60%, 10 CV) to afford (1R,3R)-1-(4-bromophenyl)-N-(4-fluorophenyl)-3-hydroxy-3-methylcyclobutanecarboxamide. MS (ESI) Calc'd [M+H]$^+$, 378; found, 378.

Step 2: Preparation of 3-chloro-N-(4-((1 r,3r)-1-((4-fluorophenyl)carbamoyl)-3-hydroxy-3-methylcyclobutyl)phenyl)benzamide To a vial was added (1r,3r)-1-(4-bromophenyl)-N-(4-fluorophenyl)-3-hydroxy-3-methylcyclobutanecarboxamide (38 mg, 0.10 mmol), 3-chlorobenzamide (24 mg, 0.15 mmol), K$_3$PO$_4$ (65 mg, 0.31 mmol), JackiePhos Pd G3 (12 mg, 10 µmol) and t-BuOH (1000 µl). The mixture was evacuated and backfilled with N$_2$ (4 times), then heated at 100° C. for 3.5 h. After 3.5 h the mixture was filtered and purified under Purification A conditions to afford the title compound. MS (ESI) Calc'd [M+H]$^+$, 453; found, 453. $^1$H NMR (600 MHz, DMSO-d$_6$) δ 10.28 (s, 1H), 9.55 (s, 1H), 7.95 (s, 1H), 7.86 (d, J=7.7 Hz, 1H), 7.66 (d, J=8.4 Hz, 2H), 7.62 (d, J=7.8 Hz, 1H), 7.58-7.48 (m, 3H), 7.33 (d, J=8.4 Hz, 2H), 7.06 (t, J=8.7 Hz, 2H), 3.38 (s, 1H), 2.96 (d, J=12.2 Hz, 2H), 2.51-2.37 (m, 2H), 1.17 (s, 3H).

Example 72: N-(4-(3,3-Difluoro-1-((4-fluorophenyl)carbamoyl)cyclobutyl)phenyl)-3-fluorobenzamide

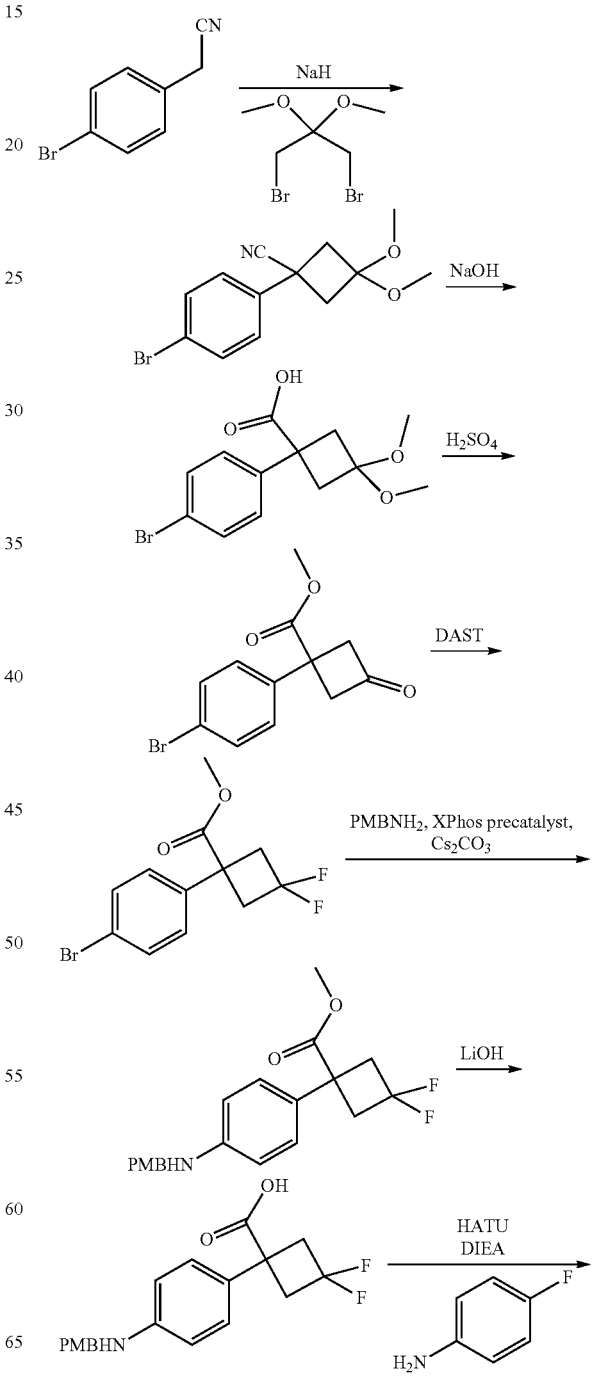

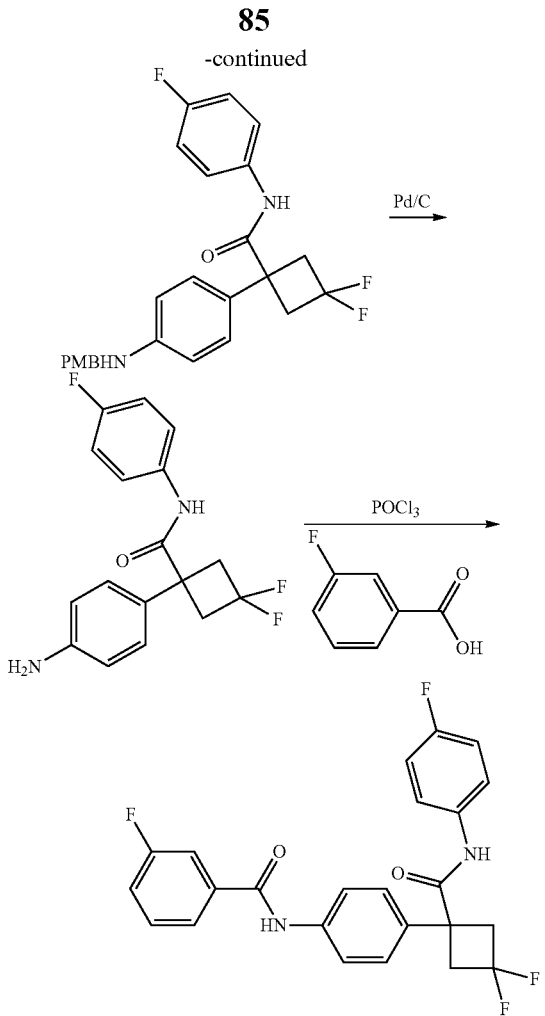

Example 72

Step 1: Preparation of 1-(4-bromophenyl)-3,3-dimethoxycyclobutanecarbonitrile To a suspension of NaH (4.1 g, 100 mmol) (60% in mineral oil) in DMF (100 mL) was added 2-(4-bromophenyl)acetonitrile (10 g, 51 mmol) followed by 1,3-dibromo-2,2-dimethoxypropane (11 g, 42 mmol). The reaction mixture was heated to 60° C. for 12 h. After 12 h the reaction mixture was diluted with water (1000 mL) and washed with EtOAc (400 mL×2). The combined organics were washed with brine (100 mL), dried over anhydrous $Na_2SO_4$, and concentrated under reduced pressure. The residue was purified by flash chromatography on silica (petroleum ether:EtOAc=50:1 to 20:1) to afford 1-(4-bromophenyl)-3,3-dimethoxycyclobutanecarbonitrile. MS (ESI) Calc'd $[M+H]^+$, 296; found, 296.

Step 2: Preparation of 1-(4-bromophenyl)-3,3-dimethoxycyclobutanecarboxylic Acid To a solution of 1-(4-bromophenyl)-3,3-dimethoxycyclobutanecarbonitrile (15.11 g, 51.0 mmol) in EtOH (20 mL) was added NaOH (5.54 g, 137 mmol) and water (5 mL) while stirring at RT. The reaction mixture was heated to 85° C. for 36 h. After 36 h the reaction mixture was concentrated under reduced pressure. The residue was diluted with water (150 mL) and washed with EtOAc (50 mL×3). The combined organics were washed with brine (50 mL), dried over $Na_2SO_4$, filtered, and concentrated under reduced pressure to afford 1-(4-bromophenyl)-3,3-dimethoxycyclobutanecarboxamide.

Step 3: Preparation of methyl 1-(4-bromophenyl)-3-oxocyclobutanecarboxylate

To a solution of 1-(4-bromophenyl)-3,3-dimethoxycyclobutanecarboxylic acid (2.5 g, 8.0 mmol) in MeOH (30 mL) was added $H_2SO_4$ (2.0 mL, 38 mmol) while stirring at RT. The reaction mixture was stirred for 14 h. After 14 h the reaction mixture was concentrated under reduced pressure. The residue was diluted with water (30 mL) and washed with EtOAc (30 mL×3). The combined organics were washed with brine (20 mL), dried over $Na_2SO_4$, filtered, and concentrated under reduced pressure. The residue was purified by silica gel column chromatography (petroleum ether:EtOAc 30:1-10:1 as eluent) to afford methyl 1-(4-bromophenyl)-3-oxocyclobutanecarboxylate.

Step 4: Preparation of methyl 1-(4-bromophenyl)-3,3-difluorocyclobutanecarboxylate To a solution of methyl 1-(4-bromophenyl)-3-oxocyclobutanecarboxylate (1.5 g, 5.4 mmol) in DCM (15 mL) was added DAST (1.4 mL, 11 mmol) while stirring at 0° C. under $N_2$. The reaction mixture was stirred at 0° C. while warming to RT for 15 h. After 15 h saturated $NaHCO_3$ (20 mL) was added slowly. The mixture was washed with DCM (30 mL×3). The combined organics were washed with brine (20 mL), dried over anhydrous $Na_2SO_4$, filtered and concentrated under reduced pressure. The residue was purified by silica gel column chromatography ($SiO_2$) using (petroleum ether:EtOAc 50:1-30:1 as eluent) to afford methyl 1-(4-bromophenyl)-3,3-difluorocyclobutanecarboxylate.

Step 5: Preparation of methyl 3,3-difluoro-1-(4-((4-methoxybenzyl)amino)phenyl)cyclobutane-1-carboxylate To a solution of methyl 1-(4-bromophenyl)-3,3-difluorocyclobutanecarboxylate (800 mg, 2.6 mmol) and (4-methoxyphenyl)methanamine (430 mg, 3.2 mmol) in dioxane (10 mL) was added $Cs_2CO_3$ (2600 mg, 7.9 mmol) and XPhos precatalyst (190 mg, 0.26 mmol) while stirring at RT under $N_2$ atmosphere. The reaction mixture was stirred 100° C. for 14 h. After 14 h the reaction mixture was diluted with water (20 mL), then washed with EtOAc (30 mL×3). The combined organics were washed with brine (20 mL), dried over anhydrous $Na_2SO_4$, filtered, and concentrated under reduced pressure. The residue was purified by silica gel column chromatography (petroleum ether:EtOAc 30:1-5:1) to afford methyl 3,3-difluoro-1-(4-((4-methoxybenzyl)amino)phenyl)cyclobutanecarboxylate.

Step 6: Preparation of 3,3-difluoro-1-(4-((4-methoxybenzyl)amino) phenyl)cyclobutanecarboxylic Acid To a solution of methyl 3,3-difluoro-1-(4-((4-methoxybenzyl)amino)phenyl)cyclobutanecarboxylate (950 mg, 2.6 mmol) in THF (2.0 ml)/MeOH (2.0 ml)/water (1.0 mL) was added lithium hydroxide hydrate (440 mg, 11 mmol) while stirring at RT. The reaction was allowed to stir at RT for 14 h. After 14 h the reaction mixture was diluted with water (10 mL) and 1N HCl was added drop wise to reach pH ~3. The combined organics were concentrated under reduced pressure. The residue was washed with EtOAc (20 mL×2). The combined organics were washed with brine (20 mL), dried over $Na_2SO_4$, filtered, and concentrated under reduced pressure to afford 3,3-difluoro-1-(4-((4-methoxybenzyl)amino) phenyl)cyclobutanecarboxylic acid. MS (ESI) Calc'd $[M+H]^+$, 348; found, 348.

Step 7: Preparation of 3,3-difluoro-N-(4-fluorophenyl)-1-(4-((4-methoxybenzyl)amino)phenyl)cyclobutanecarboxamide To a solution of 3,3-difluoro-1-(4-((4-methoxybenzyl) amino)phenyl)cyclobutanecarboxylic acid (860 mg, 2.5 mmol) and 4-fluoroaniline (300 mg, 2.7 mmol) in DCM (5.0 mL) was added HATU (940 mg, 2.5 mmol) and DIEA (1.3 ml, 7.4 mmol) while stirring at RT. The reaction mixture was stirred for 1 h. After 1 h the reaction mixture was concentrated under reduced pressure. The residue was purified by silica gel column chromatography (petroleum ether:EtOAc 20:1-5:1) to afford 3,3-difluoro-N-(4-fluorophenyl)-1-(4-((4-methoxybenzyl)amino)phenyl)cyclobutanecarboxamide. MS (ESI) Calc'd $[M+H]^+$, 441; found, 463 $(M+Na^+)$.

Step 8: Preparation of 1-(4-aminophenyl)-3,3-difluoro-N-(4-fluorophenyl)cyclobutanecarboxamide To a solution of 3,3-difluoro-N-(4-fluorophenyl)-1-(4-((4-methoxybenzyl)amino)phenyl)cyclobutanecarboxamide (460 mg, 1.04 mmol) in MeOH (10 mL) was added Pd/C (100 mg, 0.094 mmol) (10%) while stirring at RT under $N_2$ atmosphere. The reaction mixture was stirred at RT under $H_2$ (15 PSI) for 5 h. After 5 h the reaction mixture was filtered and concentrated under reduced pressure. The residue was purified by silica gel column chromatography (petroleum ether:EtOAc 5:1-2:1) to afford 1-(4-aminophenyl)-3,3-difluoro-N-(4-fluorophenyl)cyclobutanecarboxamide. MS (ESI) Calc'd $[M+H]^+$, 321; found, 321.

Step 9: Preparation of N-(4-(3,3-difluoro-1-((4-fluorophenyl)carbamoyl)cyclobutyl)-phenyl)-3-fluorobenzamide To a solution of 1-(4-aminophenyl)-3,3-difluoro-N-(4-fluorophenyl)cyclobutanecarboxamide (30 mg, 0.094 mmol) and 3-fluorobenzoic acid (13 mg, 0.094 mmol) in pyridine (2.0 mL) was added $POCl_3$ (0.474 mL, 5.09 mmol) while stirring at 0° C. The reaction mixture was stirred at 0° C. for 1 h. After 1 h, water (3 mL) was added and the mixture was concentrated under reduced pressure. The residue was purified under Purification A conditions to afford the title compound. MS (ESI) Calc'd $[M+H]^+$, 443; found, 443. $^1$H NMR (400 MHz, $CD_3OD$) δ 7.71-7.80 (m, 3H), 7.68 (br d, J=9.7 Hz, 1H), 7.43-7.58 (m, 5H), 7.29-7.38 (m, 1H), 7.02 (t, J=8.7 Hz, 2H), 3.43-3.56 (m, 2H), 3.13 (q, J=13.1 Hz, 2H).

Examples 73-76 in Table 7 were prepared in an analogous way to Example 72, using the corresponding carboxylic acids in Step 9.

TABLE 7

| Ex. # | Structure | Chemical Name | Mass [M + H]+ |
|---|---|---|---|
| 73 | 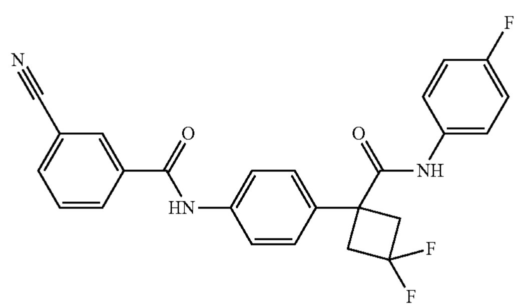 [SMILES: N#Cc1cccc(C(=O)Nc2ccc(C3(C(=O)Nc4ccc(F)cc4)CC(F)(F)C3)cc2)c1] | 3-cyano-N-(4-{3,3-difluoro-1-[(4-fluorophenyl)carbamoyl]cyclobutyl}phenyl)benzamide | 450 |
| 74 | 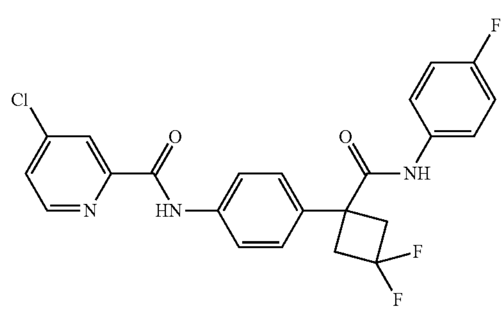 [SMILES: O=C(Nc1ccc(C2(C(=O)Nc3ccc(F)cc3)CC(F)(F)C2)cc1)c1cc(Cl)ccn1] | 4-chloro-N-(4-{3,3-difluoro-1-[(4-fluorophenyl)carbamoyl]cyclobutyl}phenyl)pyridine-2-carboxamide | 460 |

TABLE 7-continued

| Ex. # | Structure | Chemical Name | Mass [M + H]+ |
|---|---|---|---|
| 75 | 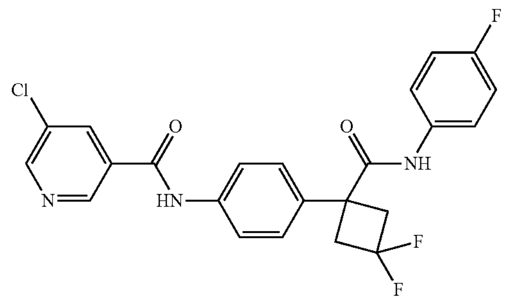 [SMILES: O=C(Nc1ccc(C2(C(=O)Nc3ccc(F)cc3)CC(F)(F)C2)cc1)c1cncc(Cl)c1] | 5-chloro-N-(4-{3,3-difluoro-1-[(4-fluorophenyl)carbamoyl]cyclobutyl}phenyl)pyridine-3-carboxamide | 460 |
| 76 | 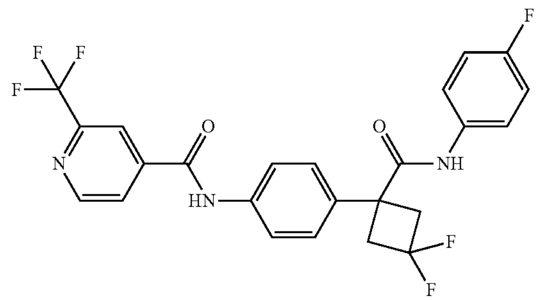 [SMILES: O=C(Nc1ccc(C2(C(=O)Nc3ccc(F)cc3)CC(F)(F)C2)cc1)c1ccnc(C(F)(F)F)c1] | N-(4-{3,3-difluoro-1-[(4-fluorophenyl)carbamoyl]cyclobutyl}phenyl)-2-(trifluoromethyl)pyridine-4-carboxamide | 494 |

Example 77: 4-Fluoro-3-methyl-N-(4-(1-(propylcarbamoyl)cyclobutyl)phenyl)benzamide

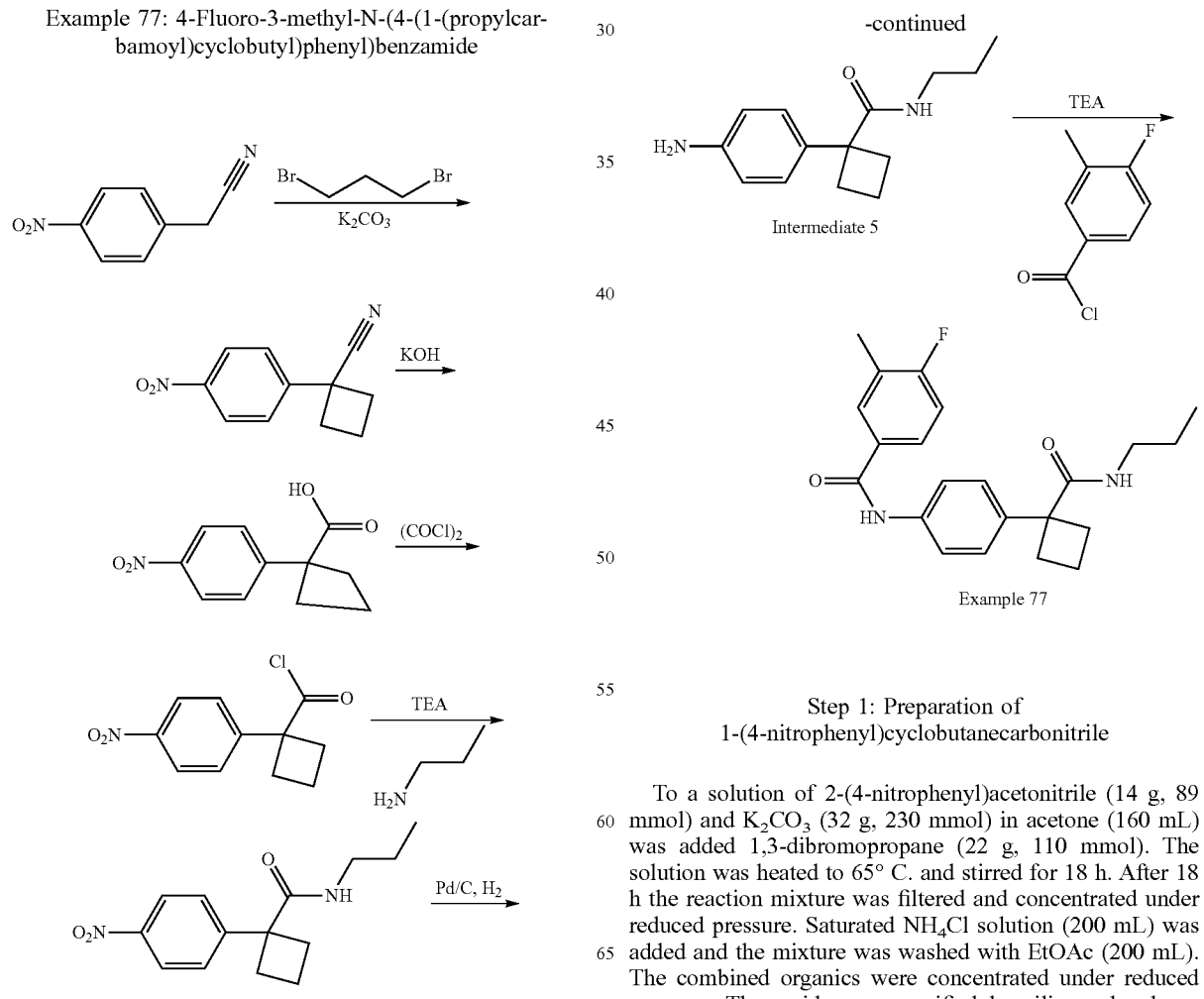

Example 77

Step 1: Preparation of 1-(4-nitrophenyl)cyclobutanecarbonitrile

To a solution of 2-(4-nitrophenyl)acetonitrile (14 g, 89 mmol) and $K_2CO_3$ (32 g, 230 mmol) in acetone (160 mL) was added 1,3-dibromopropane (22 g, 110 mmol). The solution was heated to 65° C. and stirred for 18 h. After 18 h the reaction mixture was filtered and concentrated under reduced pressure. Saturated $NH_4Cl$ solution (200 mL) was added and the mixture was washed with EtOAc (200 mL). The combined organics were concentrated under reduced pressure. The residue was purified by silica gel column chromatography (Petroleum ether:EtOAc=30:1 to 5:1) to afford 1-(4-nitrophenyl)cyclobutane-carbonitrile.

Step 2: Preparation of 1-(4-nitrophenyl)cyclobutanecarboxylic Acid

To a solution of 1-(4-nitrophenyl)cyclobutanecarbonitrile (1.5 g, 7.4 mmol) in EtOH (30 ml)/H$_2$O (10 ml) was added KOH (4.2 g, 74 mmol). The reaction mixture was stirred while refluxing for 24 h. After 24 h the reaction mixture was concentrated under reduced pressure. The residue was dissolved in water (50 mL) and the aqueous solution was washed with EtOAc (40 mL×2). The pH of the aqueous mixture was adjusted to ~2.0 (with drop wise addition of 3 M HCl) and was washed with EtOAc (50 mL×2). The combined organics were washed with brine (25 mL), dried over anhydrous sodium sulfate, filtered, and concentrated under reduced pressure to afford 1-(4-nitrophenyl)cyclobutanecarboxylic acid.

Step 3: Preparation of 1-(4-nitrophenyl)cyclobutanecarbonyl Chloride

To a solution of 1-(4-nitrophenyl)cyclobutanecarboxylic acid (900 mg, 4.1 mmol) in DCM (20 ml) was added oxalyl dichloride (1030 mg, 8.1 mmol) at 0° C., drop wise. The mixture was stirred at RT for 2 h. After 2 h the reaction mixture was concentrated under reduced pressure to afford 1-(4-nitrophenyl)cyclobutanecarbonyl chloride.

Step 4: Preparation of 1-(4-nitrophenyl)-N-propylcyclobutanecarboxamide

To a solution of propan-1-amine (330 mg, 5.6 mmol) and Et$_3$N (1.6 ml, 11 mmol) in DCM (15 mL) was added a solution of 1-(4-nitrophenyl)cyclobutanecarbonyl chloride (900 mg, 3.8 mmol) in DCM (5 mL) at 0° C. The reaction mixture was stirred at 0° C. for 1 h. After 1 h the reaction mixture was diluted with DCM (50 mL) and washed with aqueous 1.0 M HCl (20 mL×2). The resulting organics were washed with saturated NaHCO$_3$ (20 mL), and brine (20 mL). The combined organics were dried over anhydrous sodium sulfate, filtered, and concentrated under reduced pressure to afford 1-(4-nitrophenyl)-N-propylcyclobutanecarboxamide. MS (ESI) Calc'd [M+H]$^+$, 263; found, 263.

Step 5: Preparation of 1-(4-aminophenyl)-N-propylcyclobutanecarboxamide (Intermediate 5)

To a solution of 1-(4-nitrophenyl)-N-propylcyclobutanecarboxamide (900 mg, 3.43 mmol) in EtOAc (30 ml) was added Pd/C (100 mg, 0.094 mmol). The reaction mixture was stirred under 15 PSI H$_2$ at RT for 1 h. After 1 h the reaction mixture was filtered and the filter cake was washed with EtOAc (100 mL). The combined filtrate was concentrated under reduced pressure to afford 1-(4-aminophenyl)-N-propylcyclobutanecarboxamide. MS (ESI) Calc'd [M+H]$^+$, 233; found, 233.

Step 6: Preparation of 4-fluoro-3-methyl-N-(4-(1-(propylcarbamoyl)cyclobutyl)phenyl) benzamide To a solution of 1-(4-aminophenyl)-N-propylcyclobutanecarboxamide (100 mg, 0.43 mmol) (Intermediate 5) and TEA (0.180 ml, 1.29 mmol) in DCM (5 mL) was added 4-fluoro-3-methylbenzoyl chloride (150 mg, 0.86 mmol) in DCM (2 mL) while stirring at 0° C. The reaction mixture was stirred at 0° C. for 1 h. After 1 h the reaction mixture was diluted with water (100 mL) and washed with EtOAc (50 mL×2). The combined organics were washed with aqueous NaHCO$_3$ (100 mL), dried over anhydrous Na$_2$SO$_4$, filtered, and concentrated under reduced pressure. The residue was purified under Purification C conditions to afford the title compound. MS (ESI) Calc'd [M+H]$^+$, 369; found, 369. $^1$H NMR (400 MHz, DMSO-d$_6$) δ 10.2 (s, 1H), 7.9 (dd, J=7.5, 1.8 Hz, 1H), 7.8-7.9 (m, 1H), 7.7 (d, J=8.7 Hz, 2H), 7.5 (t, J=5.8 Hz, 1H), 7.3-7.3 (m, 3H), 3.0 (q, J=6.7 Hz, 2H), 2.7 (dq, J=8.3, 6.1 Hz, 2H), 2.3-2.4 (m, 5H), 1.7-1.9 (m, 2H), 1.3 (sxt, J=7.2 Hz, 2H), 0.7 (t, J=7.4 Hz, 3H).

Examples 78-81 in Table 8 were prepared in an analogous way to Example 77, using the corresponding acid chloride in Step 6.

TABLE 8

| Ex. # | Structure | Chemical Name | Mass [M + H]+ |
|---|---|---|---|
| 78 | 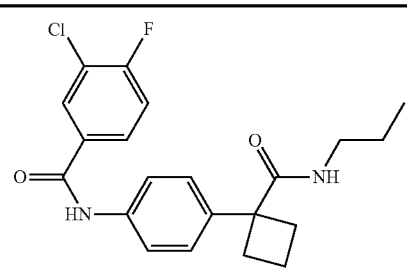 | 3-chloro-4-fluoro-N-{4-[1-(propylcarbamoyl)cyclobutyl]phenyl}benzamide | 389 |
| 79 | 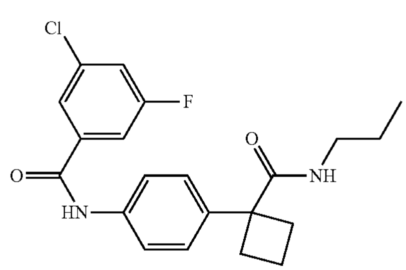 [SMILES: CCCNC(=O)C1(c2ccc(NC(=O)c3cc(F)cc(Cl)c3)cc2)CCC1] | 3-chloro-5-fluoro-N-{4-[1-(propylcarbamoyl)cyclobutyl]phenyl}benzamide | 389 |

TABLE 8-continued

| Ex. # | Structure | Chemical Name | Mass [M + H]+ |
|---|---|---|---|
| 80 | 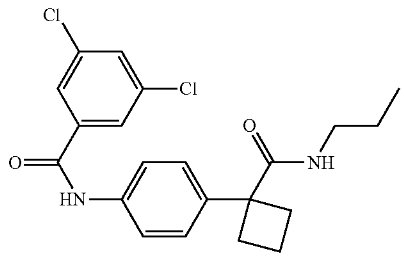 | 3,5-dichloro-N-{4-[1-(propylcarbamoyl)cyclobutyl]phenyl}benzamide | 405 |
| 81 | 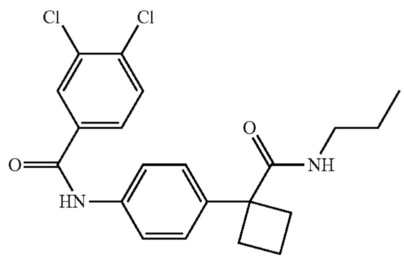 [SMILES: CCCNC(=O)C1(c2ccc(NC(=O)c3ccc(Cl)c(Cl)c3)cc2)CCC1] | 3,4-dichloro-N-{4-[1-(propylcarbamoyl)cyclobutyl]phenyl}benzamide | 405 |

Example 82: 3-Chloro-N-(2-fluoro-4-(1-((3,3,3-trifluoropropyl)carbamoyl)cyclobutyl)phenyl)benzamide

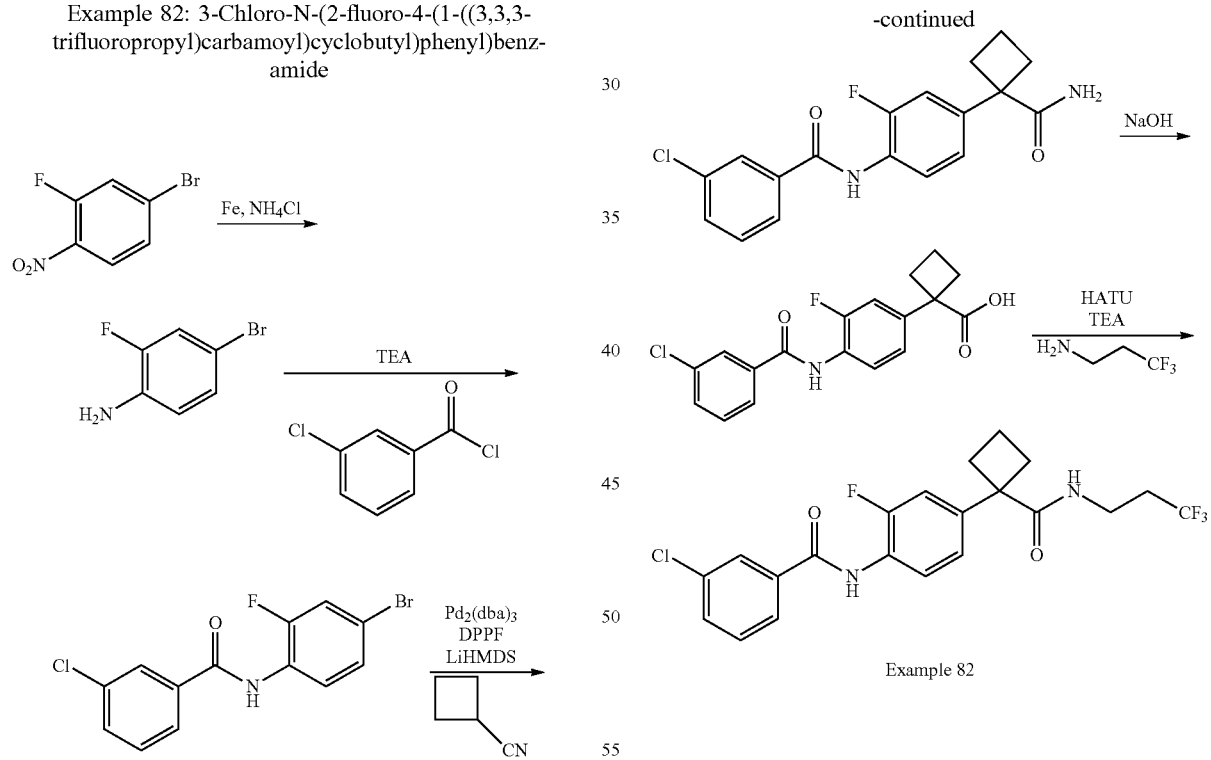

Step 1: Preparation of 4-bromo-2-fluoroaniline

To a stirred solution of 4-bromo-2-fluoro-1-nitrobenzene (10 g, 45.5 mmol) in EtOH (50 mL)/Water (20 mL) was added iron (12.7 g, 230 mmol) and NH$_4$Cl (24.3 g, 455 mmol). The reaction mixture was stirred at 90° C. for 2 h. After 2 h the reaction mixture was filtered over Celite. The filter cake was washed with EtOH (300 mL), and the filtrate was concentrated under reduced pressure. The residue was purified by silica gel chromatography (SiO$_2$, Petroleum ether/EtOAc=10:1 to 5:1) to afford 4-bromo-2-fluoroaniline.

Step 2: Preparation of N-(4-bromo-2-fluorophenyl)-3-chlorobenzamide

To a solution of 4-bromo-2-fluoroaniline (1 g, 5.26 mmol) and TEA (2.20 mL, 15.79 mmol) in DCM (15 mL) was added 3-chlorobenzoyl chloride (1.84 g, 10.53 mmol) in DCM (2 mL). The mixture was stirred at 0° C. for 1 h. After 1 h the reaction mixture was diluted with water (100 mL) and washed with EtOAc (50 mL×2). The combined organics were washed with aqueous saturated NaHCO$_3$ (100 mL), dried over anhydrous Na$_2$SO$_4$, filtered, and concentrated under reduced pressure. The residue was purified by silica gel chromatography (SiO$_2$, Petroleum ether:EtOAc=10:1 to 5:1) to afford N-(4-bromo-2-fluorophenyl)-3-chlorobenzamide.

Step 3: Preparation of 3-chloro-N-(4-(1-cyanocyclobutyl)-2-fluorophenyl)benzamide To a solution of N-(4-bromo-2-fluorophenyl)-3-chlorobenzamide (350 mg, 1.07 mmol) in THF (15 mL) was added DPPF (59 mg, 0.11 mmol), Pd$_2$(dba)$_3$ (49 mg, 0.054 mmol) and cyclobutanecarbonitrile (173 mg, 2.13 mmol). LiHMDS (2.13 ml, 2.13 mmol) was added. The reaction mixture was stirred at 80° C. for 16 h. After 16 h, aqueous NH$_4$Cl (20 mL) was added to the reaction mixture, and the reaction mixture was washed with EtOAc (10 mL×5). The combined organics were washed with brine (5 mL), dried over anhydrous Na$_2$SO$_4$, filtered, and concentrated under reduced pressure. The residue was purified by Prep-TLC using (SiO$_2$, petroleum ether:EtOAc=5:1) to afford 3-chloro-N-(4-(1-cyanocyclobutyl)-2-fluorophenyl)benzamide. MS (ESI) Calc'd [M+H]$^+$, 329; found, 329.

Step 4: Preparation of N-(4-(1-carbamoylcyclobutyl)-2-fluorophenyl)-3-chlorobenzamide To a stirred solution of 3-chloro-N-(4-(1-cyanocyclobutyl)-2-fluorophenyl)benzamide (38 mg, 0.12 mmol) in AcOH (1 mL) was added H$_2$SO$_4$ (12 mg, 0.12 mmol) at 0° C. The reaction mixture was stirred at 90° C. for 16 h. After 16 h the pH was adjusted to pH ~9 by addition of 2 N NaOH (20 mL). The reaction mixture was washed with ethyl acetate (20 mL×3) and the combined organics were washed with brine (5 mL), dried over Na$_2$SO$_4$, filtered, and concentrated under reduced pressure to afford N-(4-(1-carbamoylcyclobutyl)-2-fluorophenyl)-3-chlorobenzamide. MS (ESI) Calc'd [M+H]$^+$, 347; found, 347.

Step 5: Preparation of 1-(4-(3-chlorobenzamido)-3-fluorophenyl)cyclobutanecarboxylic Acid To a solution of N-(4-(1-carbamoylcyclobutyl)-2-fluorophenyl)-3-chlorobenzamide (20 mg, 0.058 mmol) in ethanol (2 mL) was added NaOH (28 mg, 0.700 mmol) while stirring at RT. The reaction was heated to 90° C. and the reaction mixture was stirred for 24 h. After 24 h the reaction mixture was acidified to pH-2 with 1 M HCl (2 mL). The mixture was washed with EtOAc (30 mL×3) and the combined organics were washed with brine (30 mL), dried over Na$_2$SO$_4$, filtered, and concentrated under reduced pressure. The residue was purified under Purification B conditions to afford 1-(4-(3-chlorobenzamido)-3-fluorophenyl)cyclobutanecarboxylic acid. MS (ESI) Calc'd [M+H]$^+$, 348; found, 348.

Step 6: Preparation of 3-chloro-N-(2-fluoro-4-(1-((3,3,3-trifluoropropyl)carbamoyl) cyclobutyl)phenyl)benzamide To a solution of 1-(4-(3-chlorobenzamido)-3-fluorophenyl)cyclobutanecarboxylic acid (30 mg, 0.086 mmol) and HATU (33 mg, 0.087 mmol) in DMF (1 mL) was added 3,3,3-trifluoropropan-1-amine (10 mg, 0.088 mmol) and DIEA (0.045 mL, 0.255 mmol) while stirring at RT. The reaction was stirred at RT for 18 h. After 18 h the reaction mixture was purified under Purification B conditions to afford the title compound. MS (ESI) Calc'd [M+H]$^+$, 348; found, 348. $^1$H NMR (400 MHz, CD$_3$OD) δ 8.0 (s, 1H), 7.9 (br d, J=7.5 Hz, 1H), 7.7 (t, J=8.1 Hz, 1H), 7.6 (br d, J=7.9 Hz, 1H), 7.5-7.5 (m, 1H), 7.2-7.3 (m, 2H), 3.4-3.4 (m, 2H), 2.8 (s, 2H), 2.5 (br d, J=7.5 Hz, 2H), 2.3-2.4 (m, 2H), 1.9 (br s, 2H).

Example 83: 3-Chloro-N-(2-(hydroxymethyl)-4-(1-((3,3,3-trifluoropropyl)carbamoyl)cyclobutyl)phenyl)benzamide

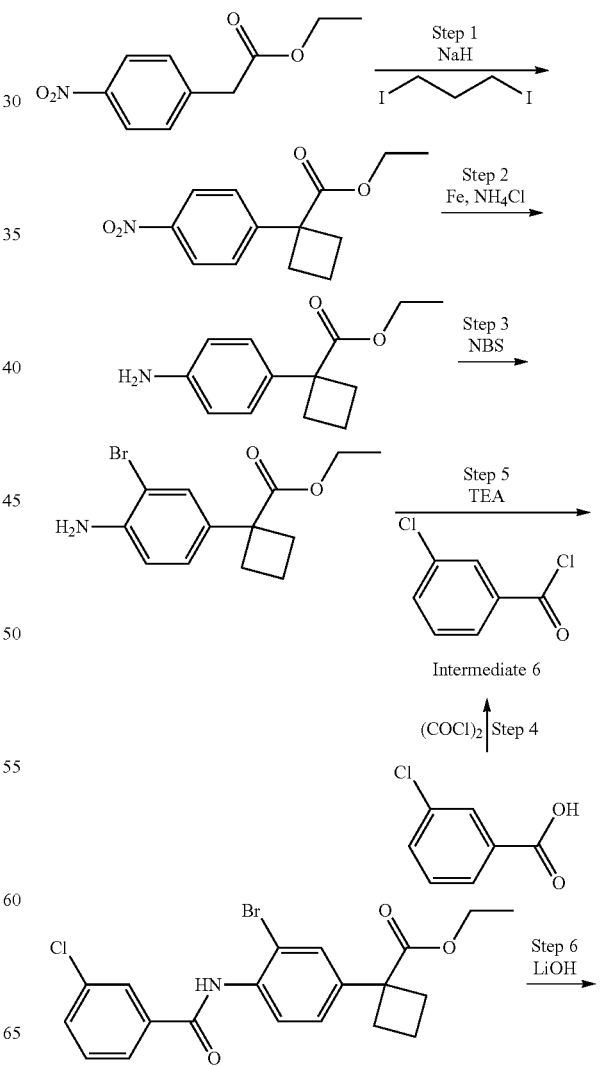

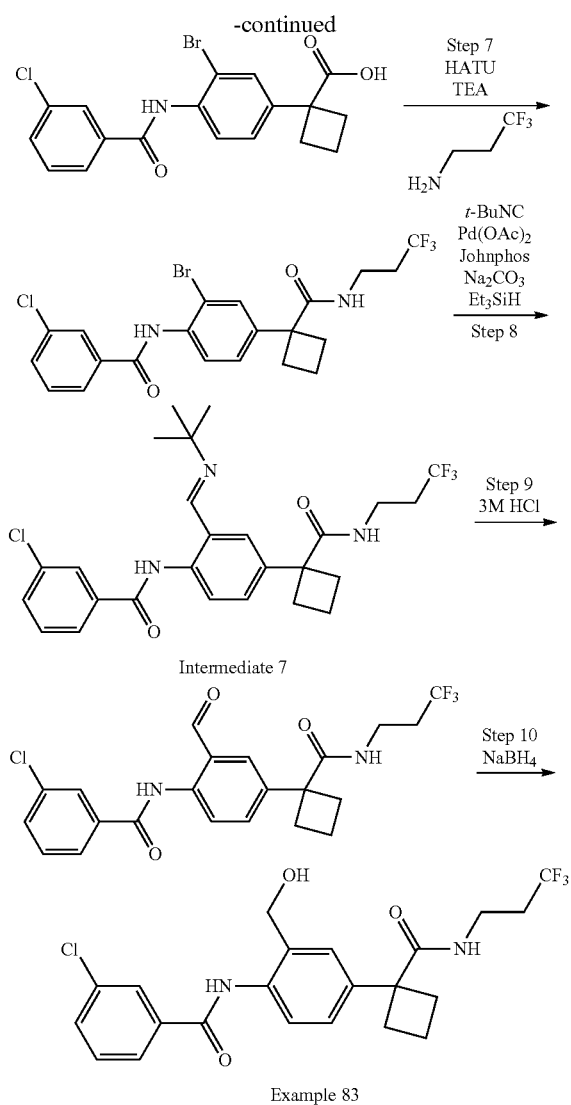

Example 83

Step 1: Preparation of ethyl 1-(4-nitrophenyl)cyclobutanecarboxylate

To a solution of ethyl 2-(4-nitrophenyl)acetate (3 g, 14.34 mmol) in DMF (60 mL) was added NaH (1.20 g, 30.1 mmol) (60% in oil) while stirring at 0° C. The reaction mixture was allowed to warm to RT and was stirred for 15 min. After 15 min the mixture was cooled to 0° C. and 1,3-diiodopropane (3.4 mL, 29.6 mmol) was added. The resulting mixture was stirred at 0° C. for 30 min, then warmed to RT and stirred for 1 h. After 1 h the reaction mixture was diluted with aqueous NH$_4$Cl (60 mL) and was washed with EtOAc (30 mL×3). The combined organic phase was washed with brine (20 mL), dried over Na$_2$SO$_4$, filtered, and concentrated under reduced pressure. The residue was purified by silica gel chromatography (Petroleum ether/EtOAc=100:1 to 50:1) to afford ethyl 1-(4-nitrophenyl)cyclobutanecarboxylate.

Step 2: Preparation of ethyl 1-(4-aminophenyl)cyclobutanecarboxylate

To a solution of ethyl 1-(4-nitrophenyl)cyclobutanecarboxylate (1.65 g, 6.62 mmol) in EtOH (27 mL)/Water (3 mL) was added ammonium chloride (3.54 g, 66.2 mmol) and iron (1.9 g, 34.0 mmol) while stirring at RT. The reaction mixture was stirred at 90° C. for 2 h. After 2 h the reaction mixture was filtered and concentrated under reduced pressure. The residue was diluted with water (30 mL) and washed with EtOAc (20 mL×3). The combined organics were washed with brine, dried over Na$_2$SO$_4$, filtered, and concentrated under reduced pressure. The residue was purified by silica gel chromatography (SiO$_2$, Petroleum ether/ EtOAc=5:1) to afford ethyl 1-(4-aminophenyl)cyclobutanecarboxylate. MS (ESI) Calc'd [M+H]$^+$, 220; found, 220.

Step 3: Preparation of ethyl 1-(4-amino-3-bromophenyl)cyclobutanecarboxylate To a solution of ethyl 1-(4-aminophenyl)cyclobutanecarboxylate (0.5 g, 2.28 mmol) in DMF (10 mL) was added NBS (0.37 g, 2.08 mmol) while stirring at −10° C. The reaction mixture was stirred −10° C. for 2 h. After 2 h the reaction mixture was diluted with water (5 mL) and washed with EtOAc (5 mL×3). The combined organics were washed with brine, dried over Na$_2$SO$_4$, filtered, and concentrated under reduced pressure. The residue was purified by silica gel chromatography (SiO$_2$, Petroleum ether/EtOAc=40:1 to 20:1) to afford ethyl 1-(4-amino-3-bromophenyl)cyclobutanecarboxylate. MS (ESI) Calc'd [M+H]$^+$, 298; found, 298.

Step 4: Preparation of 3-chlorobenzoyl Chloride (Intermediate 6)

To a solution of 3-chlorobenzoic acid (0.4 g, 2.55 mmol) in DCM (2 mL) was added DMF (0.05 g, 0.68 mmol) and oxalyl dichloride (0.44 mL, 5.13 mmol) while stirring at 0° C. The reaction mixture was stirred at 20° C. for 2 h, then concentrated under reduced pressure to afford 3-chlorobenzoyl chloride.

Step 5: Preparation of ethyl 1-(3-bromo-4-(3-chlorobenzamido)phenyl)cyclobutanecarboxylate To a solution of ethyl 1-(4-amino-3-bromophenyl)cyclobutanecarboxylate (0.46 g, 1.54 mmol) and TEA (0.47 g, 4.63 mmol) in DCM (5 mL) was added 3-chlorobenzoyl chloride (0.27 g, 1.543 mmol) (Intermediate 6) in DCM (3 mL) while stirring at 0° C. The reaction mixture was stirred at 0° C. for 3 h. After 3 h the reaction mixture was concentrated under reduced pressure. The residue was purified under Purification D conditions to afford ethyl 1-(3-bromo-4-(3-chlorobenzamido)phenyl)cyclobutanecarboxylate. MS (ESI) Calc'd [M+H]$^+$, 436; found, 438.

Step 6: Preparation of 1-(3-bromo-4-(3-chlorobenzamido)phenyl)cyclobutanecarboxylic Acid To a solution of ethyl 1-(3-bromo-4-(3-chlorobenzamido)phenyl)cyclobutanecarboxylate (0.32 g, 0.72 mmol) in MeOH (2 mL)/THF (2 mL)/water (1 mL) was added lithium hydroxide hydrate (0.15 g, 3.61 mmol) while stirring at RT. The reaction mixture was stirred at RT for 15 h. After 15 h the reaction mixture was diluted water (20 mL) and acidified with 2.0 M aqueous HCl to pH ~3.0. The mixture was washed with EtOAc (20 mL×3) and the combined organics were washed with brine, dried over Na$_2$SO$_4$, filtered, and concentrated under reduced pressure to afford 1-(3-bromo-4-(3-chlorobenzamido)phenyl)cyclobutanecarboxylic acid. MS (ESI) Calc'd [M+H]$^+$, 408; found, 410.

Step 7: Preparation of N-(2-bromo-4-(1-((3,3,3-trifluoropropyl)carbamoyl)cyclobutyl) phenyl)-3-chlorobenzamide To a solution of 1-(3-bromo-4-(3-chlorobenzamido)phenyl)cyclobutanecarboxylic acid (270 mg, 0.66 mmol) in THF (10 mL) was added HATU (276 mg, 0.73 mmol), 3,3,3-trifluoropropan-1-amine (82 mg, 0.73 mmol) and TEA (0.4 mL, 2.87 mmol) while stirring at RT. The reaction mixture was stirred at RT for 2 h. After 2 h the reaction mixture was poured into water (20 mL) and washed with EtOAc (20 mL×2). The combined organics were washed with brine (20 mL), dried over anhydrous $Na_2SO_4$, filtered, and concentrated under reduced pressure. The residue was purified by column chromatography on silica gel (Petroleum ether:EtOAc=20:1 to 5:1) to afford N-(2-bromo-4-(1-((3,3,3-trifluoropropyl)carbamoyl)cyclobutyl)phenyl)-3-chlorobenzamide. MS (ESI) Calc'd [M+H]+, 503; found, 505.

Step 8: Preparation of (E)-N-(2-((tert-butylimino) methyl)-4-(1-((3,3,3-trifluoropropyl) carbamoyl) cyclobutyl)phenyl)-3-chlorobenzamide (Intermediate 7)

To a solution of N-(2-bromo-4-(1-((3,3,3-trifluoropropyl) carbamoyl)cyclobutyl)phenyl)-3-chlorobenzamide (300 mg, 0.60 mmol) in DMF (6 mL) was added [1,1'-biphenyl]-2-yldi-tert-butylphosphine (8 mg, 0.027 mmol), 2-isocyano-2-methylpropane (60 mg, 0.72 mmol), diacetoxypalladium (4 mg, 0.018 mmol), triethylsilane (208 mg, 1.79 mmol) and $Na_2CO_3$ (64 mg, 0.60 mmol) while stirring at RT. The reaction mixture was heated to 65° C. and stirred for 10 h. After 10 h the reaction mixture was diluted with water (60 mL) and washed with EtOAc (20 mL×2). The combined organics were dried over anhydrous $Na_2SO_4$, filtered, and concentrated under reduced pressure. The residue was purified by pre-TLC (petroleum ether:EtOAc=2:1) to afford (E)-N-(2-((tert-butylimino)methyl)-4-(1-((3,3,3-trifluoropropyl)carbamoyl)cyclobutyl)phenyl)-3-chlorobenzamide. MS (ESI) Calc'd [M+H]+, 508; found, 508.

Step 9: Preparation of 3-chloro-N-(2-formyl-4-(1-((3,3,3-trifluoropropyl)carbamoyl) cyclobutyl)phenyl)benzamide To a solution of (E)-N-(2-((tert-butylimino)methyl)-4-(1-((3,3,3-trifluoropropyl)carbamoyl)cyclobutyl)phenyl)-3-chlorobenzamide (25 mg, 0.049 mmol) (Intermediate 7) in acetonitrile (2 mL)/water (1 mL) was added 3 M hydrogen chloride (0.5 mL, 1.50 mmol) while stirring at RT. The reaction mixture was stirred at RT for 5 h. After 5 h the reaction mixture was concentrated under reduced pressure to afford 3-chloro-N-(2-formyl-4-(1-((3,3,3-trifluoropropyl) carbamoyl)cyclobutyl)phenyl)benzamide. MS (ESI) Calc'd [M+H]+, 453; found, 453.

Step 10: Preparation of 3-chloro-N-(2-(hydroxymethyl)-4-(1-((3,3,3-trifluoropropyl)carbamoyl)cyclobutyl)phenyl)benzamide To a solution of 3-chloro-N-(2-formyl-4-(1-((3,3,3-trifluoropropyl)carbamoyl)cyclobutyl)phenyl)benzamide (22 mg, 0.049 mmol) in MeOH (2 mL) was added $NaBH_4$ (4 mg, 0.11 mmol) while stirring at RT. The reaction mixture was stirred at RT for 30 min. After 30 min the reaction mixture was concentrated under reduced pressure and purified under Purification B conditions to afford the title compound. MS (ESI) Calc'd [M+H]+, 455; found, 477 (M+Na+). $^1$H NMR (400 MHz, $CD_3OD$) δ 7.96 (s, 1H), 7.87 (d, J=7.8 Hz, 1H), 7.72-7.80 (m, 2H), 7.59-7.63 (m, 1H), 7.50-7.55 (m, 1H), 7.41 (d, J=2.2 Hz, 1H), 7.34 (dd, J=8.4, 2.2 Hz, 1H), 4.71 (s, 2H), 3.33-3.38 (m, 2H), 2.73-2.81 (m, 2H), 2.46-2.54 (m, 2H), 2.32 (qt, J=11.0, 7.0 Hz, 2H), 1.82-1.99 (m, 2H).

Examples 84-85 in Table 9 were prepared in an analogous way to Example 83. Example 84 was Intermediate 7 formed in the synthesis of Example 83.

TABLE 9

| Ex. # | Structure | Chemical Name | Mass [M + H]+ |
|---|---|---|---|
| 84 | 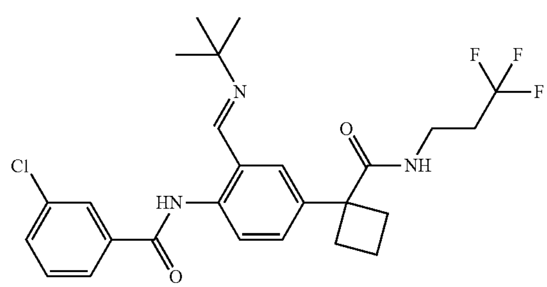 [SMILES: CC(C)(C)/N=C/c1cc(C2(C(=O)NCCC(F)(F)F)CCC2)ccc1NC(=O)c1cccc(Cl)c1] | N-(2-[(E)-(tert-butylimino)melhyl]-4-{1-[(3,3,3-trifluoropropyl)carbamoyl]cyclobutyl}phenyl)-3-chlorobenzamide | 508 |
| 85 | 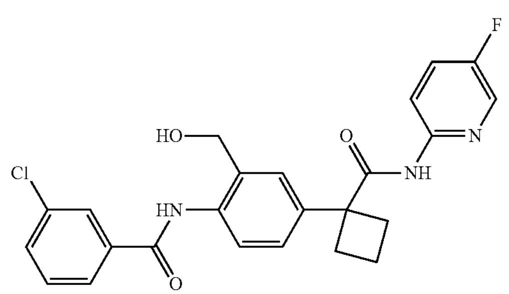 [SMILES: O=C(Nc1ccc(C2(C(=O)Nc3ccc(F)cn3)CCC2)cc1CO)c1cccc(Cl)c1] | 3-chloro-N-[4-{1-[(5-fluoropyridin-2-yl)carbamoyl]cyclobutyl}-2-(hydroxymethyl)phenyl]benzamide | 454 |

Example 86: 3-Chloro-N-(4-(1-((4-fluorobicyclo[4.2.0]octa-1(6),2,4-trien-7-yl)carbamoyl)cyclobutyl)phenyl)benzamide

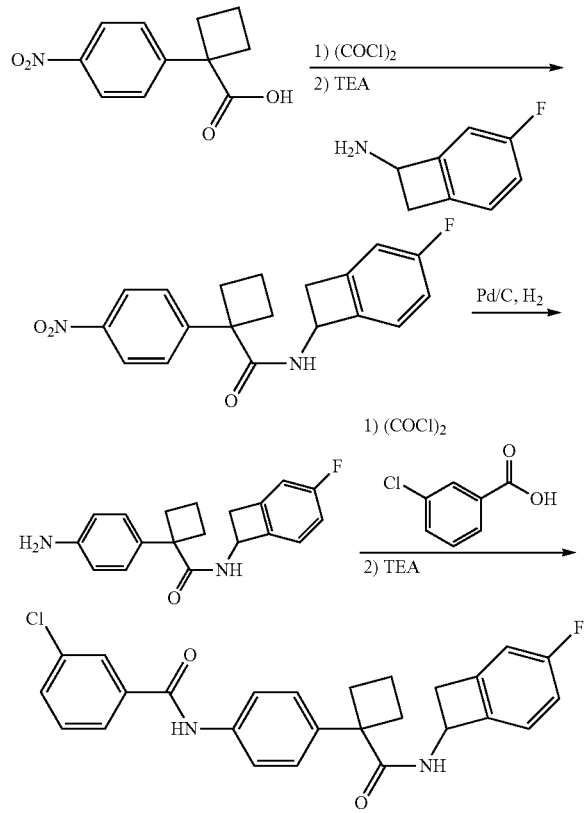

Example 86

Step 1: Preparation of N-(4-fluorobicyclo[4.2.0]octa-1 (6),2,4-trien-7-yl)-1-(4-nitrophenyl)cyclobutane-1-carboxamide To a solution of 1-(4-nitrophenyl)cyclobutanecarboxylic acid (734 mg, 3.32 mmol) and DMF (cat, 48 mg) in DCM (20 mL) was added oxalyl dichloride (842 mg, 6.64 mmol) drop wise at 0° C. The reaction mixture was stirred at RT for 2 h. After 2 h the reaction mixture was concentrated under reduced pressure. The residue was dissolved in DCM (20 mL) and TEA (0.23 ml, 1.70 mmol) was added, followed by the addition of 4-fluorobicyclo[4.2.0]octa-1(6),2,4-trien-7-amine (100 mg, 0.42 mmol) in DCM (5 mL) while stirring at 0° C. The reaction mixture was stirred at 0° C. for 1 h. After 1 h the reaction mixture was diluted with DCM (50 mL) and washed with 1.0 M HCl aqueous solution (20 mL×2). The mixture was washed with saturated NaHCO$_3$ aqueous solution (20 mL) and brine (20 mL). The combined organics were dried over anhydrous sodium sulfate, filtered, and concentrated under reduced pressure to afford N-(4-fluorobicyclo[4.2.0]octa-1 (6),2,4-trien-7-yl)-1-(4-nitrophenyl)cyclobutanecarboxamide. MS (ESI) Calc'd [M+H]$^+$, 341; found, 341.

Step 2: Preparation of N-(4-fluorobicyclo[4.2.0]octa-1 (6),2,4-trien-7-yl)-1-(4-nitrophenyl)cyclobutane-1-carboxamide To a solution of N-(4-fluorobicyclo[4.2.0]octa-1 (6),2,4-trien-7-yl)-1-(4-nitrophenyl)cyclobutanecarboxamide (142 mg, 0.42 mmol) in EtOAc (30 mL) was added Pd/C (13 mg, 0.012 mmol) and the mixture was subjected to hydrogenation under 15 PSI at 20° C. for 1 h. After 1 h the reaction mixture was filtered over Celite, rinsing with EtOAc (100 mL). The filtrate was concentrated under reduced pressure to afford 1-(4-aminophenyl)-N-(4-fluorobicyclo[4.2.0]octa-1 (6),2,4-trien-7-yl)cyclobutanecarboxamide. MS (ESI) Calc'd [M+H]$^+$, 311; found, 311.

Step 3: Preparation of 3-chloro-N-(4-(1-((4-fluorobicyclo[4.2.0]octa-1(6),2,4-trien-7-yl)carbamoyl)cyclobutyl)phenyl)benzamide To a solution of 1-(4-aminophenyl)-N-(4-fluorobicyclo[4.2.0]octa-1(6),2,4-trien-7-yl)cyclobutanecarboxamide (65 mg, 0.21 mmol) and TEA (0.088 mL, 0.63 mmol) in DCM (5 mL) was added a solution of 3-chlorobenzoyl chloride (73.3 mg, 0.42 mmol) in DCM (2 mL) while stirring at 0° C. The reaction mixture was stirred at 0° C. for 1 h. After 1 h the reaction mixture was diluted with water (50 mL) and washed with EtOAc (25 mL×2). The combined organics were washed with aqueous NaHCO$_3$ (50 mL), dried over anhydrous Na$_2$SO$_4$, filtered, and concentrated under reduced pressure. The residue was purified under Purification C conditions to afford the title compound. MS (ESI) Calc'd [M+H]$^+$, 449; found, 449. $^1$H NMR (400 MHz, DMSO-d$_6$). δ10.3 (s, 1H), 8.3 (d, J=7.5 Hz, 1H), 8.0 (s, 1H), 7.9 (d, J=7.9 Hz, 1H), 7.6-7.7 (m, 3H), 7.5-7.6 (m, 1H), 7.3 (d, J=8.3 Hz, 2H), 7.1-7.2 (m, 1H), 7.0-7.1 (m, 1H), 6.9 (br d, J=7.9 Hz, 1H), 5.2 (br s, 1H), 3.4 (dd, J=13.4, 5.0 Hz, 1H), 2.9 (br d, J=14.0 Hz, 1H), 2.6-2.8 (m, 2H), 2.3-2.4 (m, 2H), 1.7-1.9 (m, 2H).

Example 87 in Table 10 were prepared from Intermediate 5, following the conditions exemplified in the preparation of Example 86 (Step 3) using the corresponding carboxylic acid (bicyclo[4.2.0]octa-1 (6),2,4-triene-7-carboxylic acid).

TABLE 10

| Ex. # | Structure | Chemical Name | Mass [M + H]+ |
|---|---|---|---|
| 87 | 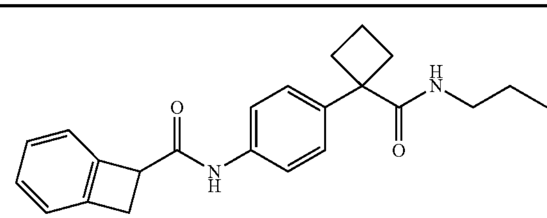 | N-{4-[1-(propylcarbamoyl)cyclobutyl]phenyl}bicyclo[4.2.0]octa-1,3,5-triene-7-carboxamide | 363 |

Biological Assays

Exemplary compounds disclosed herein were prepared, and tested to determine their effect as IDO inhibitors.

IDO1 HEK293 Cellular Assay

Compounds to be tested were serially diluted in ten 3-fold steps in DMSO starting from 10 mM DMSO stocks. Compound dilutions or DMSO alone were then dispensed from the dilution plate into a Greiner black 384-well assay plate (catalog #781086) using an Echo 550 acoustic liquid handler (Labcyte).

HEK293 cell pellets were resuspended to $5\times10^5$ cells/mL in complete HEK293 culture media (89% DMEM, 10% FBS, 1% penicillin/streptomycin). Suspended cells (2 mL) were dispensed into each well of a 6-well Corning plate (Catalog #3516). Cells were allowed to attach and were incubated for 20 hours at 37° C. in a 5% $CO_2$ incubator. Flag-IDO1 vector (Genscript True ORF Gold, 2 ug) in 150 uL of Opti-MEM medium was added to each well of a Corning 24 well plate (Cat #3527) and incubated for 5 minutes at room temperature. To each well of the 24-well plate was added 150 mL Lipofectamine 2000 (Gibco) and the plate incubated at room temperature for 20-30 minutes. To each well of attached cells in the 6-well plate, 250 mL of the transfection mix from the 24-well plate was gently added to each well and IDO1 protein was allowed to express for 24-30 hours at 37 degrees Celsius in a 5% $CO_2$ incubator.

Media was removed from the cells which were then washed with 2 mL Dulbecco's phosphate-buffered saline (DPBS). After removal of DPBS, 0.5 mL of TrypLE (Gibco) was added and incubated at 5 minutes until cells lift from the surface of the wells. Complete HEK293 culture media (4 mL) was added to each well and cells were collected and pooled into a conical tube. Cells were pelleted at 200×g for 5 minutes and resuspended in an equal volume of complete DMEM medium. Cells were diluted to $4\times10^5$ cells per mL in complete HEK293 media. L-Tryptophan was added to give a final concentration of 200 mM. The diluted transfected cells (50 mL) or nontransfected cells (50 mL) were dispensed into wells of Greiner black 384-well assay plates (catalog #781086) containing previously diluted compounds. The plate is briefly mixed and centrifuged at 200×g for 10 seconds to collect cells at the bottom of the plate. Plates were covered and incubated for 20-24 hours at 37 degrees C. in a 5% $CO_2$ incubator. Afterwards 10 mL of 0.5 M methyl isonipecotate in dimethyl sulfoxide was added to each well, mixed, sealed, and centrifuged at 500 rpm for 10 seconds. Plates were incubated at 37 degrees in a 5% $CO_2$ incubator overnight to develop fluoresence. The plates are allowed to cool and then centrifuged for 1 minute at 1000×g. The resulting fluoresence was measured in an Envision plate reader (Perkin Elmer) with a 400/25 nm excitation filter and an 510/20 nm emission filter.

The fluoresence intensity of each well was corrected for the background observed in wells with untransfected cells and was expressed as a fraction of the intensity observed in wells of IDO1 transfected cells and DMSO only. Potencies were calculated by linear least squares fit to the four parameter logistic IC50 equation.

IDO1 Cellular Assay in Hela Cells Stimulated with IFNγ

Hela cells were cultured in complete Hela culture medium (90% EMEM, 10% heat-inactivated fetal bovine serum) and expanded to about $1\times10^9$ cells. The cells were then collected and frozen down at $1\times10^7$ cells/vial in 1 mL frozen medium (90% complete Hela culture medium, 10% DMSO)

Compounds to be tested were serially diluted in ten 3-fold steps in DMSO starting from 10 mM DMSO stocks in Echo low volume plate(s). Compound dilutions or DMSO alone were then dispensed from the dilution plate(s) into Greiner black 384-well assay plate(s) (catalog #781086, 50 nL/well) using an Echo 550 acoustic liquid handler (Labcyte).

Frozen Hela cells were thawed and transferred into Hela assay medium (99% complete Hela culture medium, 1% Pen/Strep) with 20 mL medium/vial of cells. The cells were spun down at 250 g in a table top centrifuge for 5 min and suspended in same volume of Hela assay medium. The cells were then counted and adjusted to a density of $2\times10^5$ cells/ml in Hela assay medium. Sterile L-tryptophan were added to the cells with final concentration of 300 uM L-tryptophan. A small aliquot (2 mL/plate) of Hela cells were set aside and were not treated with IFNγ, to serve as the Max-E control. The rest of Hela cells were added with sterile IFNγ (Cat #285-IF, R & D systems) with a final concentration of 100 ng/mL.

Hela cells with and without IFNγ were dispensed to the respective wells of 384-well assay plates containing the compounds. The plates were incubated for about 48 hours at a 37° C., 5% $CO_2$ incubator. Afterwards, 12 mL of 0.5 M methyl isonipecotate in dimethyl sulfoxide were added into each well and the plates were sealed and incubated at 37° C. without $CO_2$ overnight. The plates were centrifuged for 1 min at 200×g. The resulting fluorescence was measured in a Spectramax plate reader (Molecular Devices) with a 400 nm excitation filter and a 510 nm emission filter.

The fluorescence intensity of each well was corrected for the background observed in wells with non-IFNγ-treated cells and was expressed as a fraction of the intensity observed in wells of IFNγ-treated cells and DMSO only. Potencies were calculated by linear least squares fit to the four parameter logistic $IC_{50}$ equation.

TDO Cellular Assay in Frozen SW48 Cells

SW48 cells were cultured in complete RPMI culture medium (90% RPMI, 10% heat-inactivated fetal bovine serum). When reaching near confluent, the cells were collected and frozen down at $20\times10^6$ cells/vial in 1 mL frozen medium (90% complete RPMI culture medium, 10% DMSO. A2780 cells (with minimal TDO activity) were cultured in complete RPMI culture medium and also frozen down at $5\times10^6$/vial similarly to serve as the Max-E control.

Compounds to be tested were serially diluted in ten 3-fold steps in DMSO starting from 10 mM DMSO stocks in Echo low volume plate(s). Compound dilutions or DMSO alone were then dispensed from the dilution plate(s) into the Greiner black 384-well assay plate(s) (catalog #781086, 50 nL/well) using an Echo 550 acoustic liquid handler (Labcyte) Frozen SW48 and A2780 cells were thawed and transferred into RPMI complete assay medium (99% complete RPMI culture medium, 1% Pen/Strep) with 20 mL medium/vial of cells. The cells were spun down at 350 g in a table top centrifuge for 5 minutes and suspended in same volume of RPMI assay medium. The cells were counted and adjusted to density of $2\times10^5$ cells/ml in RPMI assay medium. Sterile L-tryptophan (Sigma, Cat # T0254) was added to the cells with final concentration of 300 uM.

SW48 and A2780 cells were dispensed to the respective wells of 384-well assay plates containing the compounds. The plates were incubated for about 48 hours at a 37° C., 5% $CO_2$ incubator. Afterwards, 12 μL of 0.5 M ethyl isonipecotate (Sigma Aldrich, Cat # E33505) in dimethyl sulfoxide were added into each well and the plates were sealed and incubated at 37° C. without $CO_2$ overnight. The plates were centrifuged for 1 minute at 200×g. The resulting fluorescence was measured in a Spectramax plate reader (Molecular Devices) with a 400 nm excitation filter and a 510 nm emission filter.

The fluorescence intensity of each well was corrected for the background observed in wells with A2780 cells and was expressed as a fraction of the intensity observed in wells of SW48 cells and DMSO only. Potencies were calculated by linear least squares fit to the four parameter logistic $IC_{50}$ equation.

The $pIC_{50}$ values for compounds disclosed herein are shown in the following table:

| Ex. # | Hela $IC_{50}$ (nM) | HEK293 $IC_{50}$ (nM) | SW48 $IC_{50}$ (nM) | Form Screened |
|---|---|---|---|---|
| 1 | 48 | | | Neutral |
| 2 | 3 | | 10000 | Neutral |
| 3 | 131 | | 10000 | TFA Salt |
| 4 | 136 | | 10000 | TFA Salt |
| 5 | 136 | | 10000 | TFA Salt |
| 6 | 577 | | 10000 | TFA Salt |
| 7 | 4 | | 10000 | TFA Salt |
| 8 | 4 | | 10000 | Neutral |
| 9 | 11 | | 10000 | TFA Salt |
| 10 | 14 | | 10000 | Neutral |
| 11 | 19 | | 10000 | Neutral |
| 12 | 28 | 16 | 585 | TFA Salt |
| 13 | 30 | | 10000 | TFA Salt |
| 14 | 39 | 23 | 1211 | TFA Salt |
| 15 | 53 | 14 | 2505 | TFA Salt |
| 16 | 92 | | 10000 | TFA Salt |
| 17 | 108 | 125 | 10000 | Neutral |
| 18 | 92 | 92 | 10000 | Neutral |
| 19 | 2 | | 10000 | Neutral |
| 20 | 2 | | | Neutral |
| 21 | 7 | | 10000 | Neutral |
| 22 | 35 | | 10000 | Neutral |
| 23 | 78 | | 10000 | Neutral |
| 24 | 3 | | 10000 | Neutral |
| 25 | 3 | | 10000 | Neutral |
| 26 | 3 | | 10000 | Neutral |
| 27 | 4 | | 10000 | TFA Salt |
| 28 | 4 | | 10000 | TFA Salt |
| 29 | 4 | | 10000 | TFA Salt |
| 30 | 5 | | 10000 | Neutral |
| 31 | 8 | | 10000 | Neutral |
| 32 | 12 | | 10000 | Neutral |
| 33 | 15 | | 10000 | Neutral |
| 34 | 21 | | 10000 | Neutral |
| 35 | 24 | | 10000 | TFA Salt |
| 36 | 24 | | 10000 | Neutral |
| 37 | 28 | | 10000 | Neutral |
| 38 | 31 | | | Neutral |
| 39 | 34 | | | Neutral |
| 40 | 39 | | 10000 | Neutral |
| 41 | 101 | | | Neutral |
| 42 | 119 | | 10000 | Neutral |
| 43 | 660 | | | Neutral |
| 44 | 709 | | 10000 | Neutral |
| 45 | 58 | | 10000 | Neutral |
| 46 | 13 | | | Neutral |
| 47 | 26 | | | Neutral |
| 48 | 27 | | | Neutral |
| 49 | 126 | | 10000 | Neutral |
| 50 | 151 | | | Neutral |
| 51 | 404 | | 10000 | Neutral |
| 52 | 427 | | 10000 | Neutral |
| 53 | 834 | | 10000 | Neutral |
| 54 | 500 | | | TFA Salt |
| 55 | 613 | | | TFA Salt |
| 56 | 923 | | | TFA Salt |
| 57 | 1710 | | | TFA Salt |
| 58 | 2010 | | | TFA Salt |
| 59 | 17 | | 10000 | TFA Salt |
| 60 | 489 | | 10000 | TFA Salt |
| 61 | 1811 | | 10000 | TFA Salt |
| 62 | 2 | | 10000 | Neutral |
| 63 | 2 | | 10000 | Neutral |
| 64 | 37 | | 10000 | Neutral |
| 65 | 71 | | 10000 | Neutral |
| 66 | 89 | | 10000 | Neutral |
| 67 | 207 | | 10000 | Neutral |
| 68 | 1435 | | 10000 | Neutral |
| 69 | 56 | | 10000 | Neutral |
| 70 | 32 | | 10000 | Neutral |
| 71 | 440 | | 10000 | Neutral |
| 72 | 4 | | 10000 | Neutral |
| 73 | 4 | | 10000 | Neutral |
| 74 | 5 | | 10000 | Neutral |
| 75 | 10 | | 10000 | Neutral |
| 76 | 20 | | 7640 | Neutral |
| 77 | 8 | | 10000 | Neutral |
| 78 | 10 | | 10000 | Neutral |
| 79 | 11 | | 10000 | Neutral |
| 80 | 12 | | 10000 | Neutral |
| 81 | 13 | | 10000 | Neutral |
| 82 | 117 | | 10000 | Neutral |
| 83 | 128 | | 10000 | Neutral |
| 84 | 176 | | 10000 | Neutral |
| 85 | 5 | | 10000 | Neutral |
| 86 | 182 | | 10000 | Neutral |
| 87 | 1051 | | 10000 | Neutral |
| 88 | 2 | | 10000 | Neutral |

IDO1 Human Whole Blood Assay

Compounds to be tested were serially diluted in ten 3-fold steps in DMSO starting from 10 mM. 3 mL of compound dilutions or DMSO alone were then dispensed from the dilution plate into a polypropylene 96-well assay plate containing 97 mL of RPMI using an Echo 555 acoustic liquid handler (Labcyte). LPS and IFNγ was prepared in in RPMI to a 10× of final conc. (1000 ng/mL), final concentration is 100 ng/mL.

Human whole blood was drawn in sodium heparin coated tubes from healthy internal donors. 240 mL of blood was transferred to each of the wells of a v-bottom 96 well plate. 30 mL of compound was transferred from intermediate dilution plate, and incubated for 15 min. 30 µL from stimulants was then transferred to blood and mixed thoroughly. Plate was covered with breathable membrane and incubated at 37° C. for overnight (18 h).

On day 2 isotope labeled standard of kynurenine and tryptophan was made in water at 10× concentration and 30 mL was added to the blood at 3 mM final concentration. The assay plates were centrifuged at 300×G for 10 min with no brake to separate plasma from red blood cells. 60 mL of plasma samples was removed without disturbing red blood cells. Plasma was diluted with RPMI in 1:1 ratio and proteins were precipitated out with two volume of Acetonitrile. The plates was centrifuged at 4000×G for 60 min. 20 mL of supernatant was carefully transferred to a 384 well plate contain 40 mL of 0.1% formic acid in water and analyzed by LC/MS/MS.

LC/MS/MS analyses were performed using Thermo Fisher's LX4-TSQ Quantum Ultra system. This system consists of four Agilent binary high-performance liquid chromatography (HPLC) pumps and a TSQ Quantum Ultra triple quadruple MS/MS instrument. For each sample, 5 mL were injected onto an Atlantis T3 column (2.1 mm×150 mm, 3 mm particle size) from Waters. The mobile phase gradient pumped at 0.8 mL/min was used to elute the analytes from the column at 25° C. The elution started at 0% B increasing linearly to 25% B at 6.5 min, holding at 25% for 1 min, re-equilibrating to 10 min. Mobile phase A consisted of 0.1% formic acid in water. Mobile phase B consisted of 0.1% of formic acid in acetonitrile. Data was acquired in positive mode using a HESI interface. The operational parameters for the TSQ Quantum Ultra instrument were a spray voltage of 4000 V, capillary temperature of 380° C., vaporizer temperature 400° C., shealth gas 60 arbitrary units, Aux gas 20 arbitrary units, tube lens 85 and collision gas 1.2 mTorr. SRM chromatograms of kynurenine (Q1: 209.2>Q3:94.0) and internal standard (Q1: 215.3>Q3:98.2) were collected for 90 sec. The peak area was integrated by Xcalibur Quan software. The ratios between the kynurenine generated in the reaction and 2D6-Kynurenine spiked-in internal standard were used to generate percentage inhibition and $IC_{50}$ values. Compounds were titrated and $IC_{50}$'s were calculated by 4 parameter sigmoidal curve fitting formula.

The biological activity data of selective compounds using the IDO1 human whole blood assay described above are summarized in the table below.

| Ex. # | Whole Blood $IC_{50}$ (nM) | Form Screened |
|---|---|---|
| 2 | 186 | Neutral |
| 7 | 345 | TFA Salt |
| 19 | 336 | Neutral |
| 21 | 797 | Neutral |
| 27 | 21 | TFA Salt |
| 28 | 253 | TFA Salt |
| 30 | 795 | Neutral |
| 32 | 738 | Neutral |
| 33 | 1877 | Neutral |
| 35 | 1604 | TFA Salt |
| 63 | 70 | Neutral |
| 70 | 1712 | Neutral |
| 77 | 333 | Neutral |
| 85 | 219 | Neutral |
| 88 | 57 | Neutral |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of formula (Ib), or a pharmaceutically acceptable salt thereof:

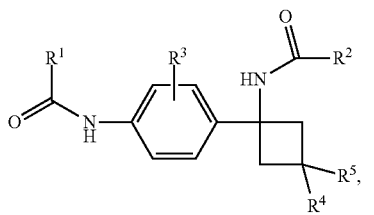

wherein:
$R^1$ is selected from:
(1) $C_{3-6}$ cycloalkyl, optionally substituted with 1-3 substituents independently selected from (a) halogen, (b) —O—$C_{1-6}$ alkyl and (c) $C_{1-6}$ alkyl optionally substituted with 1-3 halogens,
(2) phenyl, optionally substituted with 1-3 substituents independently selected from (a) halogen, (b) —CN, (c) —O—$C_{1-6}$ alkyl and (d) $C_{1-6}$ alkyl optionally substituted with 1-3 halogens,
(3) a bicyclic ring comprising a phenyl fused to a $C_{4-7}$cycloalkyl, wherein the bicyclic ring is optionally substituted with halogen or $C_{1-6}$ alkyl, and (4) a heterocyclyl selected from (a) a saturated 4-7 membered monocyclic heterocyclyl, (b) a partially unsaturated 4-7 membered monocyclic heterocyclyl, (c) an aromatic 4-7 membered monocyclic heterocyclyl, and (d) a 6-9 membered fused bicyclic ring containing one or more heteroatoms selected from N, O, and S in either of the rings, wherein the heterocyclyl is optionally substituted with 1-3 substituents independently selected from (a) halogen, (b) —CN and (c) $C_{1-6}$ alkyl;

$R^2$ is selected from:
(1) $C_{1-6}$ alkyl, optionally substituted with 1-3 substituents independently selected from (a) halogen and (b) $C_{3-6}$ cycloalkyl,
(2) $C_{3-6}$ cycloalkyl, optionally substituted with 1-3 substituents independently selected from (a) halogen and (b) $C_{1-6}$ alkyl optionally substituted with $NH_2$,
(3) phenyl, optionally substituted with 1-3 substituents independently selected from (a) halogen and (b) $C_{1-6}$ alkyl,
(4) a bicyclic ring comprising a phenyl fused to a $C_{4-7}$cycloalkyl, optionally substituted with halogen or $C_{1-6}$ alkyl,
(5) $S(O)_2$-aryl, and
(6) a heterocyclyl selected from (a) a saturated 4-7 membered monocyclic heterocyclyl, (b) a partially unsaturated 4-7 membered monocyclic heterocyclyl, and (c) an aromatic 4-7 membered monocyclic heterocyclyl, wherein the heterocyclyl is optionally substituted with 1-3 substituents independently selected from (a) halogen and (b) $C_{1-6}$ alkyl;

$R^3$ is selected from (1) H, (2) fluoro, (3) methyl, (4) ethyl, (5) —$CH_2$—OH, and (6) —C═N—C($CH_3$)$_3$; and
each of $R^4$ and $R^5$ is independently selected from (1) H, (2) halogen, (3) —OH, and (4) methyl.

2. A compound selected from the group consisting of, or a pharmaceutically acceptable salt thereof:
N-(4-(1-butyramidocyclobutyl)phenyl)-3-chlorobenzamide,
3-chloro-N-(4-(1-(4-cyanobenzamido)cyclobutyl)phenyl)benzamide,
N-(1-{4-[(3-chlorobenzene-1-carbonyl)amino]phenyl}cyclobutyl)pyrazine-2-carboxamide,
3-chloro-N-(1-{4-[(3-chlorobenzene-1-carbonyl)amino]phenyl}cyclobutyl)pyridine-2-carboxamide,
4-chloro-N-(1-{4-[(3-chlorobenzene-1-carbonyl)amino]phenyl}cyclobutyl)pyridine-2-carboxamide,
N-(1-{4-[(3-chlorobenzene-1-carbonyl)amino]phenyl}cyclobutyl)-1-methyl-1H-imidazole-2-carboxamide,
6-chloro-N-(1-{4-[(3-chlorobenzene-1-carbonyl)amino]phenyl}cyclobutyl)pyridine-3-carboxamide,
4-chloro-N-(1-{4-[(3-chlorobenzene-1-carbonyl)amino]phenyl}cyclobutyl)-3-fluorobenzamide,
5-chloro-N-(1-{4-[(3-chlorobenzene-1-carbonyl)amino]phenyl}cyclobutyl)pyridine-2-carboxamide,
N-(1-{4-[(3-chlorobenzene-1-carbonyl)amino]phenyl}cyclobutyl)-3,4-difluorobenzamide,
3,4-dichloro-N-(1-{4-[(3-chlorobenzene-1-carbonyl)amino]phenyl}cyclobutyl)benzamide,
N-(1-{4-[(3-chlorobenzene-1-carbonyl)amino]phenyl}cyclobutyl)-1,3-oxazole-2-carboxamide,
N-(1-{4-[(3-chlorobenzene-1-carbonyl)amino]phenyl}cyclobutyl)-1-methyl-1H-pyrazole-3-carboxamide,
N-(1-{4-[(3-chlorobenzene-1-carbonyl)amino]phenyl}cyclobutyl)-1,3-thiazole-4-carboxamide, N-(1-{4-[(3-chlorobenzene-1-carbonyl)amino]
  phenyl}cyclobutyl)-1,3-thiazole-2-carboxamide,
N-(1-{4-[(3-chlorobenzene-1-carbonyl)amino]
  phenyl}cyclobutyl)-1,3-oxazole-4-carboxamide,
N-(4-{1-[(4-chlorobenzene-1-carbonyl)amino]
  cyclobutyl}phenyl)pyrimidine-5-carboxamide,
N-(1-{4-[(3-chlorobenzene-1-carbonyl)amino]
  phenyl}cyclobutyl)pyrimidine-5-carboxamide,
3-chloro-N-(4-(1-(4-chlorobenzamido)cyclobutyl)phe-
  nyl)benzamide,
3-chloro-N-(4-(1-((4-fluorophenyl)carbamoyl)cy-
  clobutyl)phenyl)benzamide,
1-(4-(3-chlorobenzamido)phenyl)cyclobutane-1-carbox-
  ylic acid,
3-chloro-N-(4-{1-[(4-chlorophenyl)carbamoyl]
  cyclobutyl}phenyl)benzamide,
3-chloro-N-(4-{1-[(2,4-difluorophenyl)carbamoyl]
  cyclobutyl}phenyl)benzamide,
3-chloro-N-(4-{1-[(3,4-difluorophenyl)carbamoyl]
  cyclobutyl}phenyl)benzamide,
3-chloro-N-(4-{1-[(6-chloropyridin-3-yl)carbamoyl]
  cyclobutyl}phenyl)benzamide,
3-chloro-N-(4-{1-[(5-fluoropyridin-2-yl)carbamoyl]
  cyclobutyl}phenyl)benzamide,
3-chloro-N-(4-{1-[(6-fluoropyridin-3-yl)carbamoyl]
  cyclobutyl}phenyl)benzamide,
3-chloro-N-{4-[1-(cyclohexylcarbamoyl)cyclobutyl]
  phenyl}benzamide,
3-chloro-N-(4-{1-[(2-ethylcyclopropyl)carbamoyl]
  cyclobutyl}phenyl)benzamide,
3-chloro-N-[4-(1-{[(1R,2R)-2-(trifluoromethyl)cyclopro-
  pyl]carbamoyl}cyclobutyl)phenyl]benzamide,
3-chloro-N-(4-{1-[(4,4-difluorocyclohexyl)carbamoyl]
  cyclobutyl}phenyl)benzamide,
3-chloro-N-(4-{1-[(oxan-4-yl)carbamoyl]
  cyclobutyl}phenyl)benzamide,
3-chloro-N-(4-{1-[(1-methyl-1H-pyrazol-3-yl)carbam-
  oyl]cyclobutyl}phenyl)benzamide,
3-chloro-N-(4-{1-[(2-ethoxycyclopropyl)carbamoyl]
  cyclobutyl}phenyl)benzamide,
3-chloro-N-[4-(1-{[2-(difluoromethyl)cyclopropyl]
  carbamoyl}cyclobutyl)phenyl]benzamide,
3-chloro-N-(4-{1-[(3,3-difluorocyclobutyl)carbamoyl]
  cyclobutyl}phenyl)benzamide,
N-(4-{1-[(bicyclo[1.1.1]pentan-1-yl)carbamoyl]
  cyclobutyl}phenyl)-3-chlorobenzamide,
3-chloro-N-(4-{1-[(oxan-3-yl)carbamoyl]
  cyclobutyl}phenyl)benzamide,
3-chloro-N-(4-{1-[(1-cyclopropylethyl)carbamoyl]
  cyclobutyl}phenyl)benzamide,
3-chloro-N-(4-{1-[(2,2-dimethyloxan-4-yl)carbamoyl]
  cyclobutyl}phenyl)benzamide,
3-chloro-N-[4-(1-{[1-(oxolan-2-yl)ethyl]
  carbamoyl}cyclobutyl)phenyl]benzamide,
3-chloro-N-[4-(1-{[1-(2,2,2-trifluoroethyl)azetidin-3-yl]
  carbamoyl}cyclobutyl)phenyl]benzamide,
3-chloro-N-(4-(1-((2-ethoxypropyl)carbamoyl)cy-
  clobutyl)phenyl)benzamide,
3-chloro-N-(4-{1-[(2-methylcyclopropyl)carbamoyl]
  cyclobutyl}phenyl)benzamide,
3-chloro-N-(4-{1-[(3,3,3-trifluoropropyl)carbamoyl]
  cyclobutyl}phenyl)benzamide,
3-chloro-N-(4-{1-[(cyclopropylmethyl)carbamoyl]
  cyclobutyl}phenyl)benzamide,
3-chloro-N-(4-{1-[(2,2,2-trifluoroethyl)carbamoyl]
  cyclobutyl}phenyl)benzamide,
3-chloro-N-{4-[1-(ethylcarbamoyl)cyclobutyl]
  phenyl}benzamide,
3-chloro-N-[4-(1-{[(3S)-oxolan-3-yl]
  carbamoyl}cyclobutyl)phenyl]benzamide,
3-chloro-N-[4-(1-{[(3R)-oxolan-3-yl]
  carbamoyl}cyclobutyl)phenyl]benzamide,
3-chloro-N-(4-{1-[(phenylsulfonyl)carbamoyl]
  cyclobutyl}phenyl)benzamide,
5-methyl-N-(4-(1-(propylcarbamoyl)cyclobutyl)phenyl)-
  1,2,3-thiadiazole-4-carboxamide,
4-(aminomethyl)-N-{4-[1-(propylcarbamoyl)cyclobutyl]
  phenyl}benzamide,
3-methyl-N-{4-[1-(propylcarbamoyl)cyclobutyl]phe-
  nyl}-1,2-oxazole-5-carboxamide,
2-ethyl-N-{4-[1-(propylcarbamoyl)cyclobutyl]phenyl}-
  1,3-oxazole-4-carboxamide,
N-{4-[1-(propylcarbamoyl)cyclobutyl]phenyl}imidazo
  [1,2-b]pyridazine-2-carboxamide,
N-(3-chloro-2-fluorophenyl)-4-(1-((5-fluoropyridin-2-yl)
  carbamoyl)cyclobutyl)benzamide,
N-cyclohexyl-4-{1-[(5-fluoropyridin-2-yl)carbamoyl]
  cyclobutyl}benzamide,
N-(4,4-difluorocyclohexyl)-4-{1-[(5-fluoropyridin-2-yl)
  carbamoyl]cyclobutyl}benzamide,
3-chloro-N-(4-(3-fluoro-1-((4-fluorophenyl)carbamoyl)
  cyclobutyl)phenyl)benzamide,
3-chloro-N-(4-(3,3-difluoro-1-((4-fluorophenyl)carbam-
  oyl)cyclobutyl)phenyl)benzamide,
3-chloro-N-[4-(1-{[(1S,2R)-2-ethoxycyclopropyl]car-
  bamoyl}-3,3-difluorocyclobutyl)phenyl]benzamide,
3-chloro-N-(4-{1-[(2-ethoxycyclopropyl)carbamoyl]-3,
  3-difluorocyclobutyl}phenyl)benzamide,
3-chloro-N-[4-(1-{[(1R,2S)-2-ethoxycyclopropyl]car-
  bamoyl}-3,3-difluorocyclobutyl)phenyl]benzamide,
3-chloro-N-[4-(1-{[(1R,2R)-2-ethoxycyclopropyl]car-
  bamoyl}-3,3-difluorocyclobutyl)phenyl]benzamide,
3-chloro-N-(4-{3,3-difluoro-1-[(3,3,3-trifluoropropyl)
  carbamoyl]cyclobutyl}phenyl)benzamide,
3-chloro-N-(4-((cis)-1-((4-fluorophenyl)carbamoyl)-3-
  hydroxycyclobutyl)phenyl)benzamide,
3-chloro-N-(4-((1r,3r)-1-((4-fluorophenyl)carbamoyl)-3-
  hydroxy-3-methylcyclobutyl)phenyl)benzamide,
N-(4-(3,3-difluoro-1-((4-fluorophenyl)carbamoyl)cy-
  clobutyl)phenyl)-3-fluorobenzamide,
3-cyano-N-(4-{3,3-difluoro-1-[(4-fluorophenyl)carbam-
  oyl]cyclobutyl}phenyl)benzamide,
4-chloro-N-(4-{3,3-difluoro-1-[(4-fluorophenyl)carbam-
  oyl]cyclobutyl}phenyl)pyridine-2-carboxamide,
5-chloro-N-(4-{3,3-difluoro-1-[(4-fluorophenyl)carbam-
  oyl]cyclobutyl}phenyl)pyridine-3-carboxamide,
N-(4-{3,3-difluoro-1-[(4-fluorophenyl)carbamoyl]
  cyclobutyl}phenyl)-2-(trifluoromethyl)pyridine-4-car-
  boxamide,
4-fluoro-3-methyl-N-(4-(1-(propylcarbamoyl)cyclobutyl)
  phenyl)benzamide,
3-chloro-4-fluoro-N-{4-[1-(propylcarbamoyl)cyclobutyl]
  phenyl}benzamide,
3-chloro-5-fluoro-N-{4-[1-(propylcarbamoyl)cyclobutyl]
  phenyl}benzamide,
3,5-dichloro-N-{4-[1-(propylcarbamoyl)cyclobutyl]
  phenyl}benzamide,
3,4-dichloro-N-{4-[1-(propylcarbamoyl)cyclobutyl]
  phenyl}benzamide,
3-chloro-N-(2-fluoro-4-(1-((3,3,3-trifluoropropyl)car-
  bamoyl)cyclobutyl)phenyl)benzamide,
3-chloro-N-(2-(hydroxymethyl)-4-(1-((3,3,3-trifluoro-
  propyl)carbamoyl)cyclobutyl)phenyl)benzamide, N-(2-[(E)-(tert-butylimino)methyl]-4-{1-[(3,3,3-trifluoropropyl)carbamoyl]cyclobutyl}phenyl)-3-chlorobenzamide, 3-chloro-N-(4-(1-((4-fluorobicyclo[4.2.0]octa-1(6),2,4-trien-7-yl)carbamoyl)cyclobutyl)phenyl)benzamide, and N-{4-[1-(propylcarbamoyl)cyclobutyl]phenyl}bicyclo[4.2.0]octa-1,3,5-triene-7-carboxamide.

3. A composition which comprises an inert carrier and a compound of claim 1 or a pharmaceutically acceptable salt thereof.

4. A method for treating an IDO-associated disease or disorder in a mammalian subject which comprises administering to the subject an effective amount of a compound of claim 1 or a pharmaceutically acceptable salt thereof.

5. A method for treating an IDO-associated disease or disorder in a mammalian subject which comprises administering to the subject an effective amount of a compound of claim 1 or a pharmaceutically acceptable salt thereof in combination with another anti-cancer agent.

6. The method of any of claim 4, wherein the IDO-associated disease or disorder is a cancer, viral infection, HCV infection, depression, neurodegenerative disorders, trauma, age-related cataracts, organ transplantation, and autoimmune diseases.

7. The method of claim 6, wherein the cancer is selected from a cancer of the colon, pancreas, breast, prostate, lung, brain, ovary, cervix, testes, renal, head and neck, lymphoma, leukemia, and melanoma.

\* \* \* \* \*